(12) United States Patent
Yue et al.

(10) Patent No.: US 11,986,482 B2
(45) Date of Patent: May 21, 2024

(54) METHOD OF PROMOTING ANTITUMOR OR ANTI-CANCER IMMUNITY

(71) Applicants: City University of Hong Kong, Kowloon (HK); 6J Biotechnology (Hong Kong) Limited, Shatin (HK)

(72) Inventors: Jianbo Yue, Kowloon (HK); Qingru Zhang, Kowloon (HK); Zuodong Ye, Kowloon (HK); Wang Peng, Kowloon (HK)

(73) Assignees: City University of Hong Kong, Kowloon (HK); 6J Biotechnology (Hong Kong) Limited, Shatin (HK)

( * ) Notice: Subject to any disclaimer, the term of this patent is extended or adjusted under 35 U.S.C. 154(b) by 0 days.

(21) Appl. No.: 17/699,693

(22) Filed: Mar. 21, 2022

(65) Prior Publication Data
US 2022/0305022 A1    Sep. 29, 2022

Related U.S. Application Data

(60) Provisional application No. 63/163,221, filed on Mar. 19, 2021.

(51) Int. Cl.
*A61P 35/00* (2006.01)
*A61K 31/5377* (2006.01)
*A61K 39/395* (2006.01)

(52) U.S. Cl.
CPC ...... *A61K 31/5377* (2013.01); *A61K 39/3955* (2013.01); *A61P 35/00* (2018.01)

(58) Field of Classification Search
CPC .............................. A61K 31/5377; A61P 35/00
See application file for complete search history.

(56) References Cited

U.S. PATENT DOCUMENTS

2021/0139505 A1*  5/2021  Bram ................... C07D 401/14

OTHER PUBLICATIONS

Capping protein regulates endosomal trafficking by controlling F-actin density around endocytic vesicles and recruiting RAB5 effectors; Wang, Ye, et al. eLife 2021;10:e65910. DOI: https://doi.org/10.7554/eLife.65910.
Vacuolin-1 potently and reversibly inhibits autophagosome-lysosome fusion by activating RAB5AISSN: 1554-8627 (Print) 1554-8635 (Online) Journal homepage: http://www.tandfonline.com/loi/kaup20;Autophagy 10:11, 1895-1905; Nov. 2014; © Published with license by Taylor & Francis.
Identification of Novel Vacuolin-1 Analogues as Autophagy Inhibitors by Virtual Drug Screening and Chemical Synthesis Chen, Chang et al. Molecules 2017, 22, 891; doi:10.3390/molecules22060891 www.mdpi.com/journal/molecules.
Vacuolin-1 inhibits endosomal trafficking and metastasis via CapZß; Ye, Zuodong et al; Springer Nature; Published online: Feb. 9, 2021.

* cited by examiner

*Primary Examiner* — Paul V Ward
(74) *Attorney, Agent, or Firm* — Renner, Kenner, Greive, Bobak, Taylor & Weber

(57) ABSTRACT

Methods of inhibiting endosomal trafficking of PD-L1, inducing PD-L1 secretion via exosomes, decreasing PD-L1 level at a surface of a cancer or tumor cell, and treating a cancer or tumor through promoting T cell immune response in a subject suffering from a cancer or tumor, includes the step of administering a compound of Formula I to various cells. Also, a composition to treat a cancer or a tumor, includes a compound of Formula I and an anti-PD-1 antibody.

25 Claims, 58 Drawing Sheets
(47 of 58 Drawing Sheet(s) Filed in Color)

METHOD OF PROMOTING ANTITUMOR OR ANTI-CANCER IMMUNITY

FIELD OF THE INVENTION

This invention relates to a method of regulating PD-L1 to treat a cancer or tumor. Particularly, this invention relates to a method of inhibiting endosomal trafficking of PD-L1 to treat a cancer or tumor through promoting T cell immune response.

BACKGROUND

Cancer immunotherapy utilizing the host immune system to fight against cancer has become an established pillar of cancer treatment. Its success mainly depends on the discovery of immune checkpoint proteins and immune checkpoint blockade therapy (ICBT). Blockade of negative feedback signaling to immune cells results in an enhanced immune response against tumors. One ligand-receptor interaction under investigation is the interaction between the transmembrane programmed cell death 1 protein (PD-1) and its ligand, PD-1 ligand 1 (PD-L1). PD-1 is a protein on the surface of T and B cells that regulates the immune system's response to the cells of the human body by down-regulating the immune system and promoting self-tolerance by suppressing T cell inflammatory activity. PD-L1, one of the critical immune checkpoint proteins, has been found to be overexpressed in various solid malignancies. PD-L1 expressed on cancer cells interacts with PD1 on T cells to inhibit the activation and expansion of cytotoxicity T cells and thus enable cancer cells to escape immune surveillance. Disruption of the PD-L1/PD1 axis using a blocking antibody has shown momentous clinical benefits and durable responses in different cancer types.

The development of antibodies targeting PD-L1 or PD1 is significantly increasing, and several PD-L1 or PD1 antibodies have been approved by FDA and EMA, such as Nivolumab (Opdivo) and Durvalumab (Imfinzi). However, only a subset of the total treated patients benefits from these agents, and drug resistance has been developed during or after ICBT. To date, the mechanism of how PD-L1 is dysregulated in cancer cells to evade immune surveillance remains unclear. Recent studies find that mutations in JAKI/2 compromised PD-L1 expression on cancer cells, resulting in resistance to PD1 blockade therapy. Oncogenic pathways, such as PI3K, STAT3, have also been found to upregulate PD-L1 expression on cancer cells. This may partially restore PD-L1/PD-1 function by providing more PD-L1 binding sites to impair the neutralization efficiency of antibodies.

Moreover, many patients initially display a positive response to ICBT treatment but acquire resistance and show significant relapse in the long term. However, the mechanism of primary or acquired resistance of ICBT remains unclear. The relatively weak penetration ability of antibody drugs into the complex tumor microenvironment due to their relatively large size may also limit their therapeutic efficacy. Therefore, understanding the mechanisms of PD-L1 regulation in cancer cells and developing more effective and specific approaches to target PD-L1 are essential not only for improving ICBT efficiency but also for overcoming drug resistance. The success of anti-CTLA-4, anti-PD-L1 and anti-PD1 antibodies against a variety of cancers has revolutionized cancer immunotherapy. However, only a small portion of the patients respond to these antibody therapies, and some patients develop primary or secondary resistance to antibody therapy.

Accordingly, there is a need for new methods and compositions to overcome drug resistance during ICBT, and improve ICBT therapeutic efficiency.

SUMMARY OF THE INVENTION

An embodiment of the present invention relates to a method of inhibiting endosomal trafficking of PD-L1, including the step of administering a compound of Formula I below to a cancer or tumor cell,

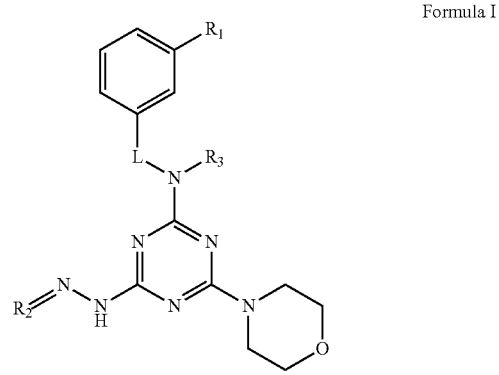

Formula I where R1 is selected from the group of a hydrogen atom, a halogen atom and a halogenated group;
where R2 is selected from the group of

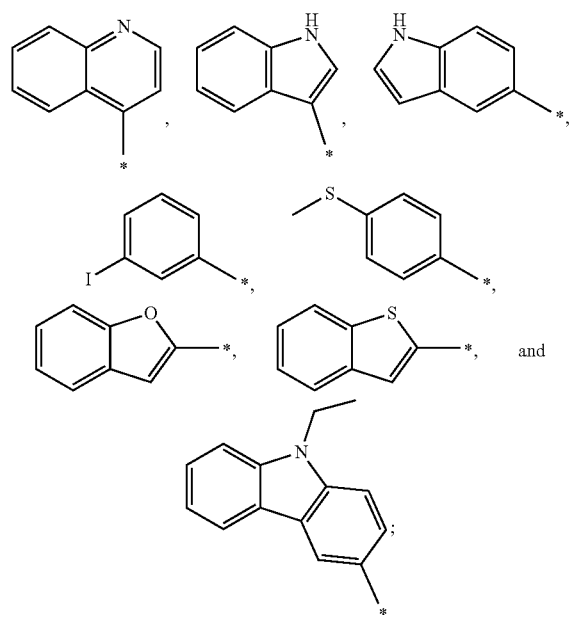

and where R3 is a hydrogen atom or

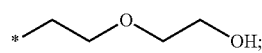 [SMILES: *CCOCCO]

and where L is a linker group —(CH$_2$)n- where n is an integer from 0-5.

An embodiment of the present invention also relates to a method of inducing PD-L1 secretion via exosomes, including the step of administering a compound of Formula I to a cancer or tumor cell:

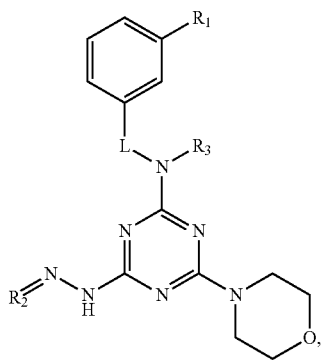

Formula I where R1 is selected from the group of a hydrogen atom, a halogen atom and a halogenated group;

where R2 is selected from the group of

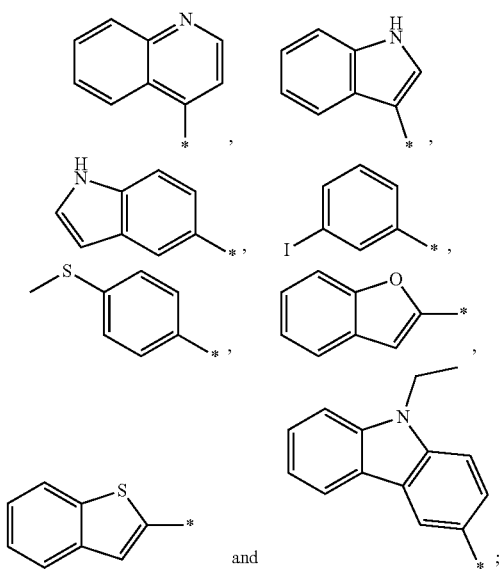

and

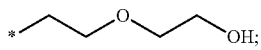

where R3 is a hydrogen atom or

*—CH$_2$CH$_2$—O—CH$_2$CH$_2$—OH;

and where L is a linker group —(CH$_2$)n- where n is an integer from 0-5.

An embodiment of the present invention also relates to a method of decreasing PD-L1 level at a surface of a cancer or tumor cell, including the step of administering a compound of Formula I to a cancer or tumor cell:

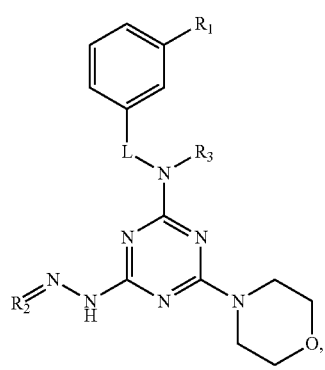

Formula I where R1 is selected from the group of a hydrogen atom, a halogen atom and a halogenated group;

where R2 is selected from the group of

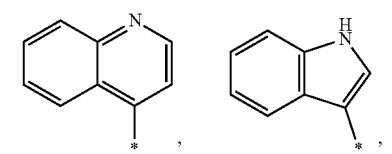

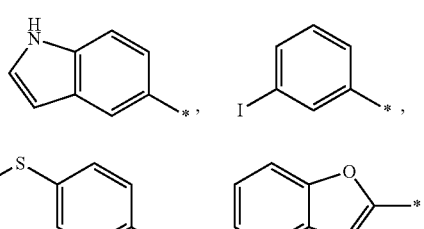

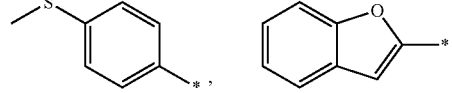

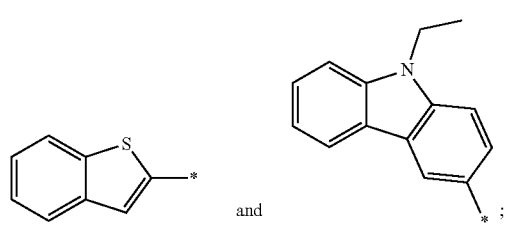

and where R3 is a hydrogen atom or

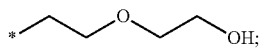 [SMILES: *CCOCCO]

and where L is a linker group —(CH$_2$)n- where n is an integer from 0-5.

An embodiment of the present invention also relates to a method of treating a cancer or tumor through promoting T cell immune response in a subject suffering from a cancer or tumor, including the step of administering an effective amount of a compound of Formula I below,

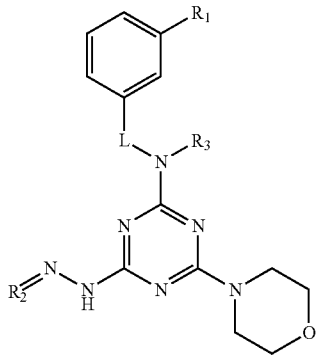

Formula I where R1 is selected from the group of a hydrogen atom, a halogen atom and a halogenated group;

where R2 is selected from the group of

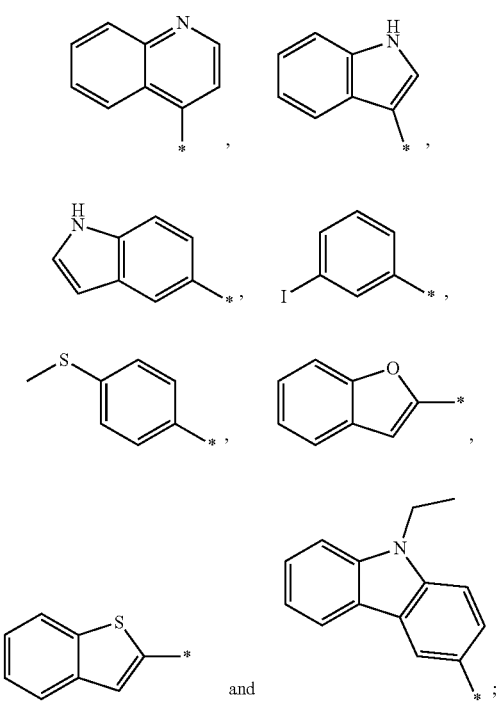

where R3 is a hydrogen atom or

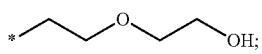

and where L is a linker group —(CH$_2$)n- where n is an integer from 0-5.

An embodiment of the present invention also relates to a composition to treat a cancer or a tumor, including a compound of Formula I and an anti-PD-1 antibody,

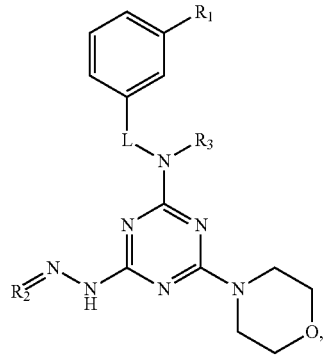

Formula I where R1 is selected from the group of a hydrogen atom, a halogen atom and a halogenated group;

where R2 is selected from the group of

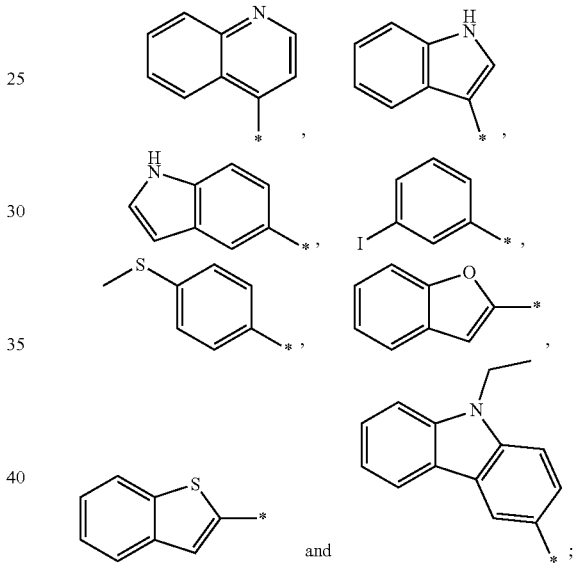

where R3 is a hydrogen atom or

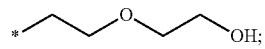 [SMILES: *CCOCCO]

and where L is a linker group —(CH$_2$)n- where n is an integer from 0-5.

Without intending to be limited by theory it is believed that the present invention may provide a method of inhibiting endosomal trafficking, endocytic trafficking and recycling endosomal trafficking of PD-L1 by the synthesized 6-morpholine-1,3,5-triazine derivatives. The present invention may provide a method of inducing PD-L1 secretion via exosomes by activation of Rab27 by the synthesized 6-morpholine-1,3,5-triazine derivatives. The present invention may provide a method of decreasing PD-L1 level at a surface of a cancer or tumor cell by the synthesized 6-morpholine-1,3,5-triazine derivatives. The present invention may further provide a method of treating breast cancer, melanoma, and lung cancer through promoting T cell immune response through chemokine secretion induced by administrating the synthesized 6-morpholine-1,3,5-triazine derivatives. The present invention may further provide a method of treating breast cancer, melanoma, and lung cancer through promoting T cell immune response by administrating the combination of the synthesized 6-morpholine-1,3,5-triazine derivatives, an exosome secretion inhibitor and/or an anti-PD-1 antibody. The present invention may further provide a composition to treat a cancer or a tumor of the synthesized 6-morpholine-1,3,5-triazine derivatives, an exosome secretion inhibitor and/or an anti-PD-1 antibody.

PD-L1 is one of the critical immune checkpoint proteins in various solid malignancies and can inhibit T cells. The present invention demonstrates that manipulation of PD-L1 endosomal trafficking is a promising means to promote anti-cancer immunity in addition to immune checkpoint antibody therapy. Also, the invention shows that the inhibition of PD-L1 endocytic trafficking by the synthesized 6-morpholine-1,3,5-triazine derivatives reduces the level of PD-L1 at the cell surface of tumor cells. Moreover, these inhibitors also increase the number of tumor-infiltrating cytotoxic T cells and promote the secretion of chemokines (e.g., CCL2, CCL3, and CCL4) in the tumor microenvironment in a syngeneic tumor mouse model. Therefore, the invention provides a novel approach for developing PD-L1 inhibitors that can be used parallel to existing antibody drugs.

It is believed that PD-L1 is internalized via the endocytosis pathway, colocalized with Rab5-positive endosomes and multivesicular bodies, and then directed sequentially to the lysosomes, recycling compartments, and/or secretory vesicles. Thus, inventors synthesize a series of compounds of 6-morpholine-1,3,5-triazine derivatives. The in vitro result shows that these compounds can inhibit the endosomal trafficking of PD-L1 and induce PD-L1 accumulated at endosomes. They also promote PD-L1 secretion via exosomes, ultimately leading to the decrease of the level of PD-L1 at the plasma membrane. Moreover, inhibiting PD-L1 secretion significantly enhances the anti-cancer efficiency of these derivatives in vivo. Therefore, the present invention shows that the inhibition of PD-L1 endocytic trafficking by the synthesized 6-morpholine-1,3,5-triazine derivatives reduces the level of PD-L1 at the cell surface of tumor cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 17A:
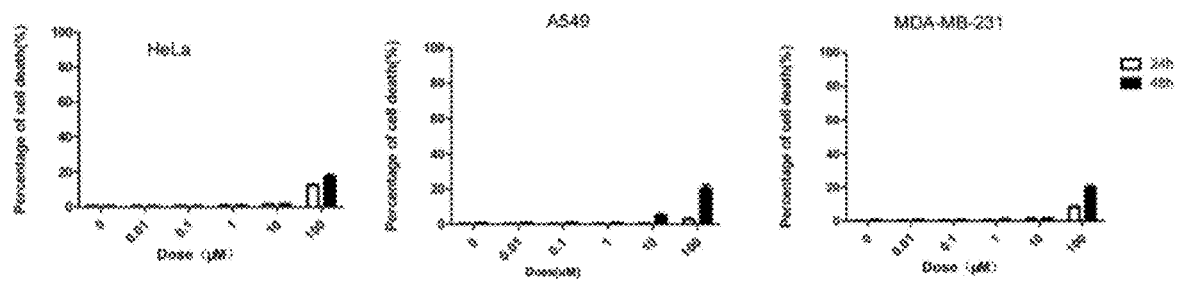
FIG. 17a is graphs showing percentages of cell deaths of propidium iodide-stained HeLa, A549, and MDA-MB-231 cells treated with or without 6J1 at the concentrations of 0, 0.01, 0.1, 1, 10 and 100 μM indicated for 24 h or 48 h.
Figure 17B:
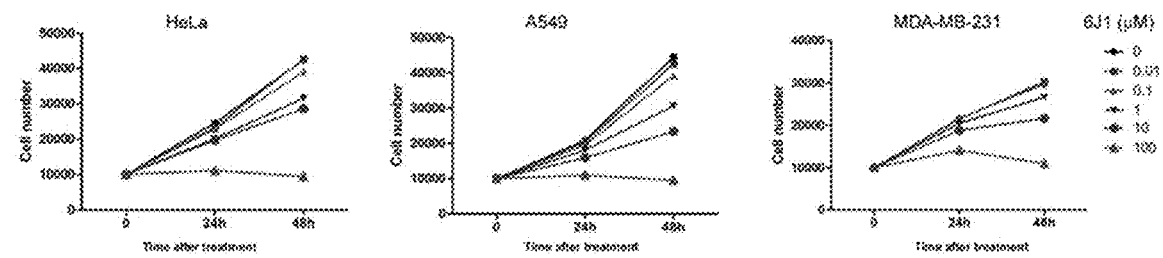

FIG. 17b is graphs showing cell numbers of Hochest 33342-stained HeLa, A549, and MDA-MB-231 cells treated with or without 6J1 at the concentrations of 0, 0.01, 0.1, 1, 10 and 100 μM indicated for 24 h or 48 h.

Figure 17C:
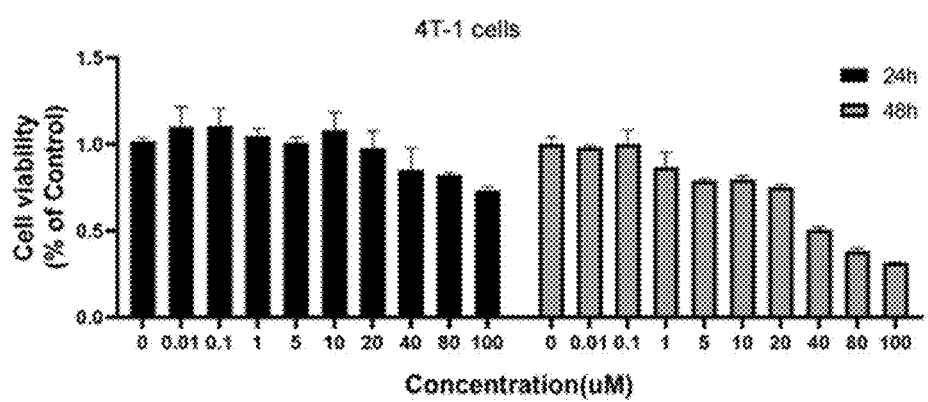

FIG. 17c is a graph showing cell viability of 4T1 cells treated with or without 6J1 at the concentrations of 0, 0.01, 0.1, 1, 5, 10, 20, 40, 80 and 100 μM indicated for 24 h or 48 h.

Figure 18A:
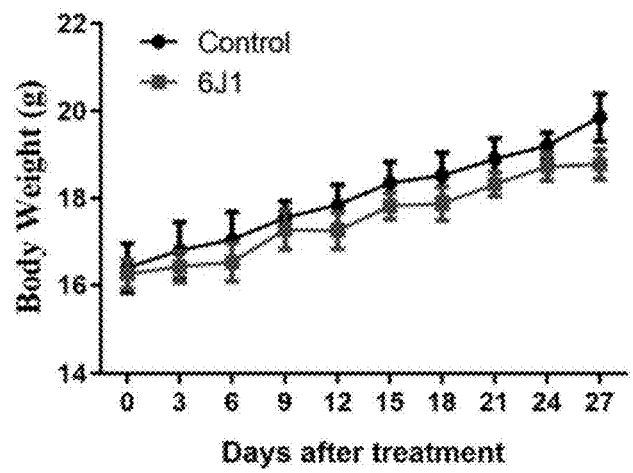

FIG. 18a is a graph showing body weights during the treatment of 6-week-old Balb/C mice treated with vesicle control (PEG400/Ethanol/tween80, 1:1:1) or 6J1 (30 mg/kg, per day) via oral route for 4 weeks.

Figure 18B:
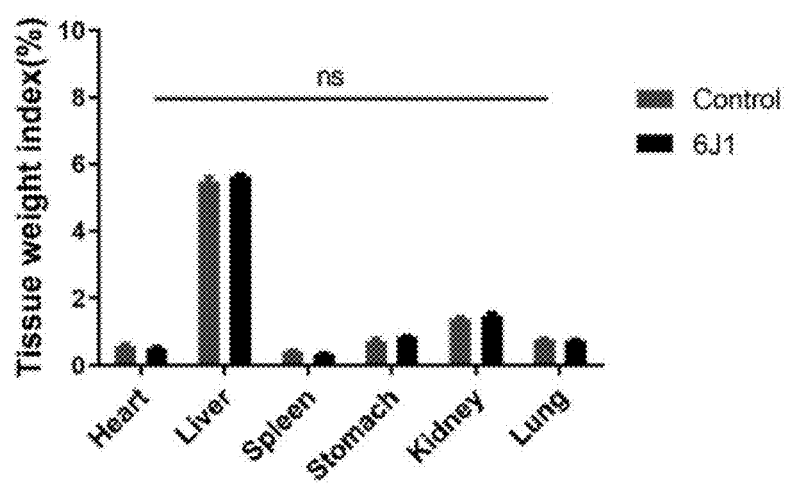

FIG. 18b is a graph showing tissue weight index (tissue weight/body weight×100%) of 6-week-old Balb/C mice treated with vesicle control (PEG400/Ethanol/tween80, 1:1:1) or 6J1 (30 mg/kg, per day) via oral route for 4 weeks.

Figure 18C:
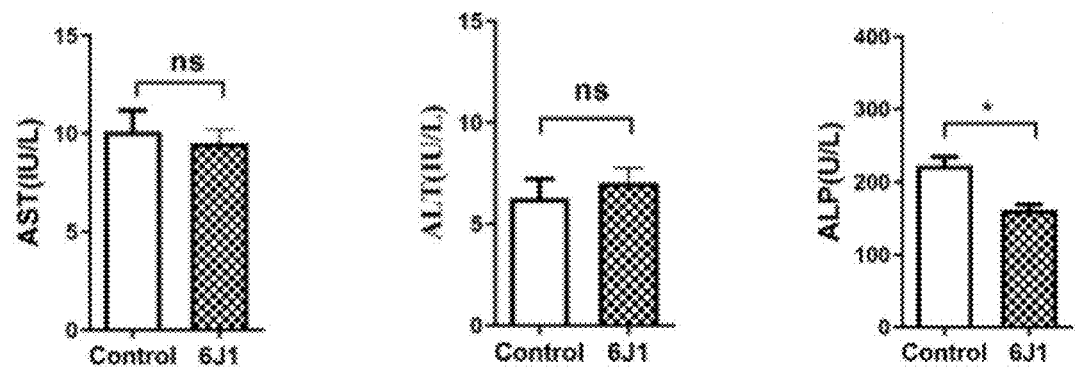

FIG. 18c is graphs showing levels of AST, ALT, and ALP in blood at the end of the experiment of 6-week-old Balb/C mice treated with vesicle control (PEG400/Ethanol/tween80, 1:1:1) or 6J1 (30 mg/kg, per day) via oral route for 4 weeks.

Figure 18D:
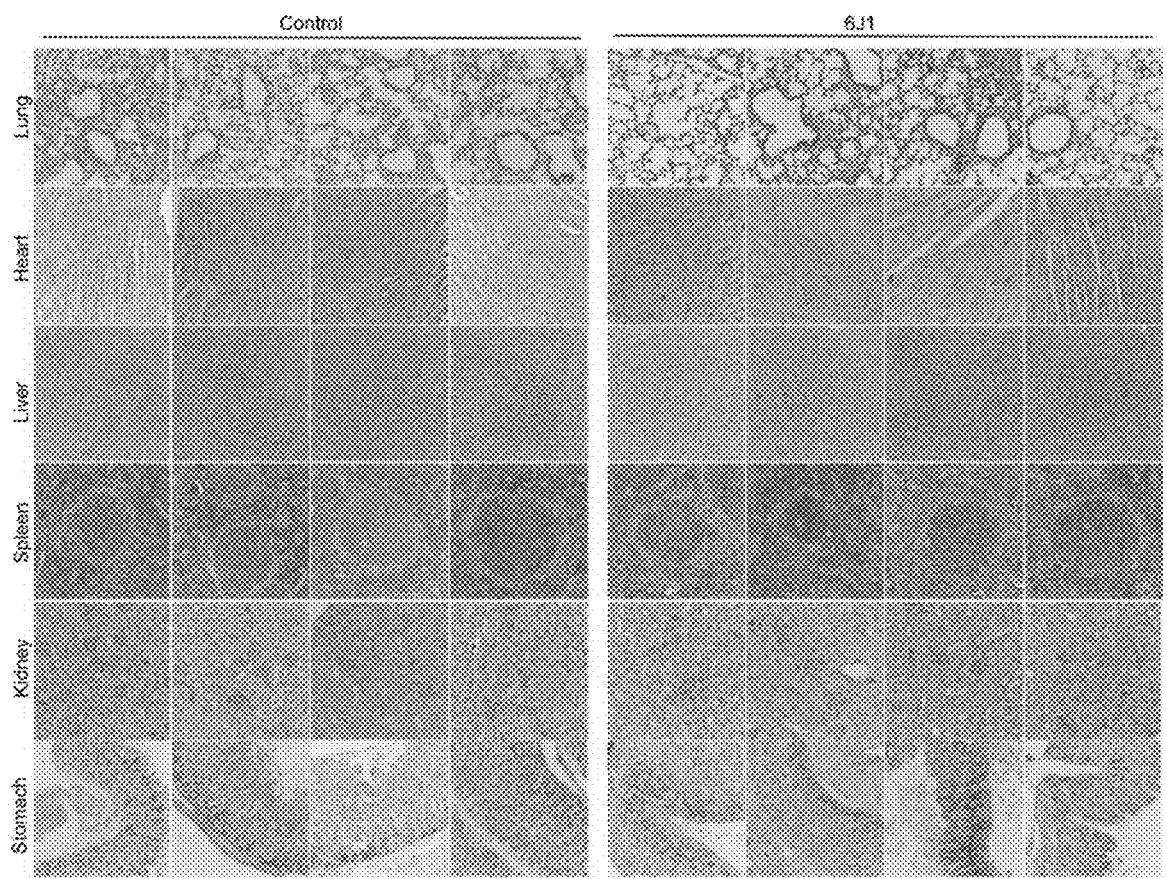

FIG. 18d is cell images of H&D-stained major organs at the end of the experiment of 6-week-old Balb/C mice treated with vesicle control (PEG400/Ethanol/tween80, 1:1:1) or 6J1 (30 mg/kg, per day) via oral route for 4 weeks.

Figure 18E:
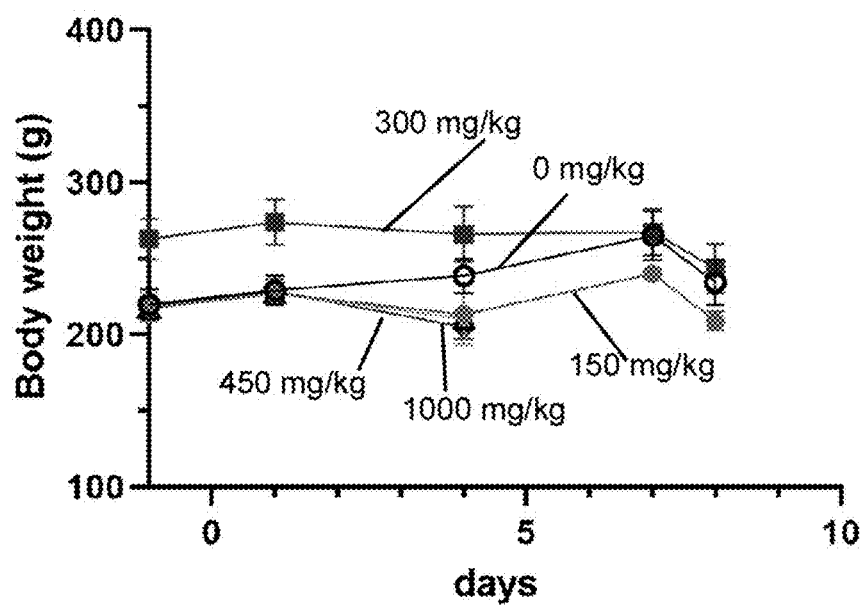

FIG. 18e is a graph showing bodyweight changes of rats following oral gavage administration of 6J1 at dose levels of 0 (vehicle), 150, 450, and 1000 mg/kg once daily for up to 7 consecutive days.

Figure 19:
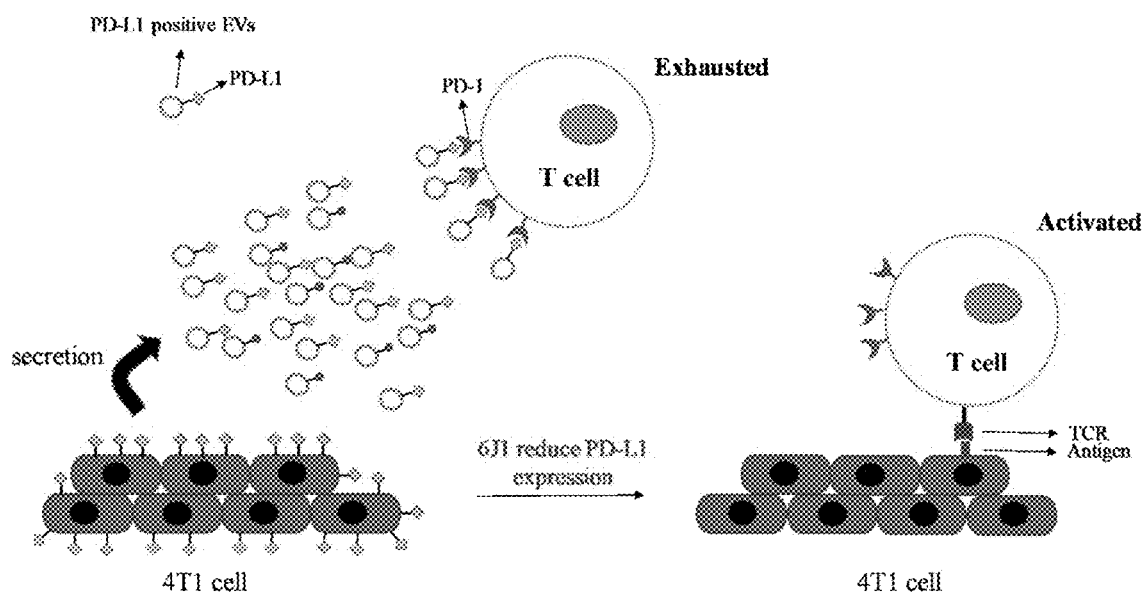

FIG. 19 is a model of the anti-cancer effect of 6J1.

The figures herein are for illustrative purposes only and are not necessarily drawn to scale.

DESCRIPTION OF THE PREFERRED EMBODIMENTS

Unless otherwise specifically provided, all tests herein are conducted at standard conditions which include a room and testing temperature of 25° C., sea level (1 atm.) pressure, pH 7, and all measurements are made in metric units. Furthermore, all percentages, ratios, etc. herein are by weight, unless specifically indicated otherwise. All the results and graphs represented data from three independent experiments, and data quantifications are expressed as mean±s.e.m. The asterisks indicate significant differences at *P<0.05,  P<0.01, *P<0.001.

It is understood that unless otherwise specifically noted, the materials compounds, chemicals, etc. described herein are typically commodity items and/or industry-standard items available from a variety of suppliers worldwide.

An embodiment of the present invention relates to a method of inhibiting endosomal trafficking, including the step of administering a compound of Formula I below to a cancer or tumor cell,

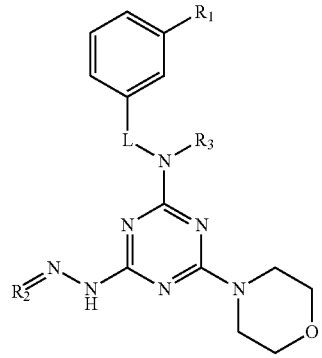

Formula I where R1 is selected from the group of a hydrogen atom, a halogen atom and a halogenated group;
where R2 is selected from the group of

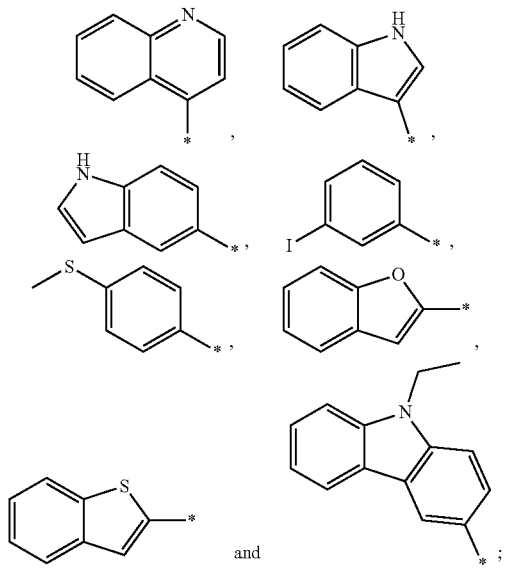

where R3 is a hydrogen atom or

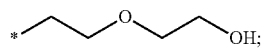 [SMILES: *CCOCCO]

and
where L is a linker group —(CH$_2$)n- where n is an integer from 0-5.

Without intending to be limited by theory it is believed that 6-morpholine-1,3,5-triazine derivatives synthesized in the present invention inhibit endosomal trafficking and induce exosome secretion of PD-L1. PD-L1 is one of the critical immune checkpoint proteins in various solid malignancies and can inhibit T cells. Manipulation of PD-L1 endosomal trafficking is a promising means to promote anti-cancer immunity in addition to immune checkpoint antibody therapy. The triazine compound, 6J1, inhibits the endosomal trafficking of PD-L1 and induces its exosomal secretion. This ultimately leads to a decrease of PD-L1 at the plasma membrane. In addition, a combination of 6J1 with the inhibition of exosomal PD-L1 secretion or with a PD-1 monoclonal antibody, both significantly promotes the anticancer immune response. These important results indicate that compromising the endosomal trafficking of PD-L1 is an effective approach to improve the efficacy of immune checkpoint inhibitors.

In an embodiment herein, the inhibition of endosomal trafficking of PD-L1 includes an inhibition of endocytic trafficking of PD-L1.

In an embodiment herein, the inhibition of endosomal trafficking of PD-L1 includes an inhibition of recycling endosomal trafficking of PD-L1.

Another embodiment herein, A method of inducing PD-L1 secretion via exosomes, including the step of administering a compound of Formula I below to a cancer or tumor cell, Formula I

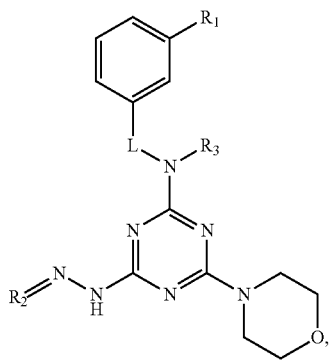

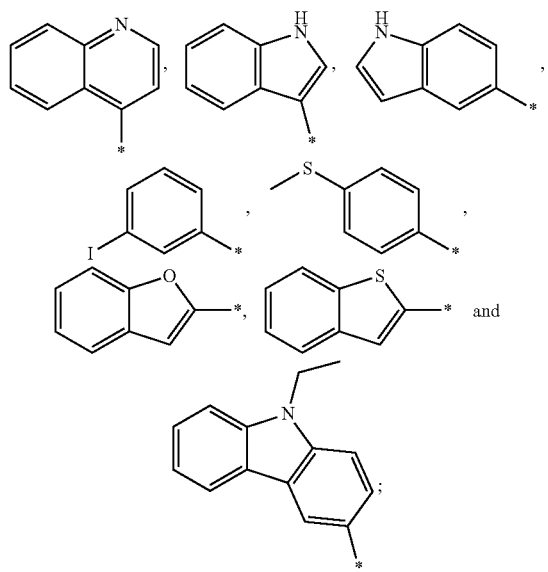

where R1 is selected from the group of a hydrogen atom, a halogen atom and a halogenated
where R2 is selected from the group of where R3 is a hydrogen atom or

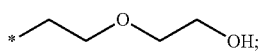

where L is a linker group —(CH$_2$)n- where n is an integer from 0-5.

In an embodiment herein, the compound activates Rab27a to induce PD-L1 secretion via exosomes.

Another embodiment herein, a method of decreasing PD-L1 level at a surface of a cancer or tumor cell, including the step of administering a compound of Formula I below to a cancer or tumor cell:

Formula I

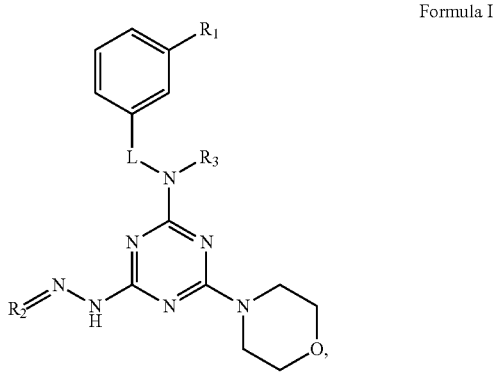

where R1 is selected from the group of a hydrogen atom, a halogen atom and a halogenated group;
where R2 is selected from the group of

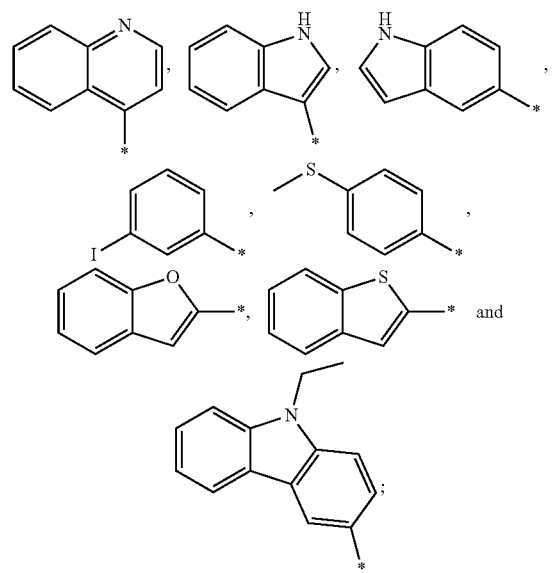

and
where R3 is a hydrogen atom or

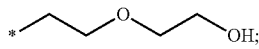

where L is a linker group —(CH$_2$)n- where n is an integer from 0-5.

Another embodiment herein, a method of treating a cancer or tumor through promoting T cell immune response in a subject suffering from a cancer or tumor, including the step of administering an effective amount of a compound of Formula I below,

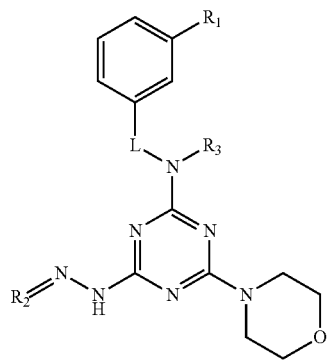

Formula I where R1 is selected from the group of a hydrogen atom, a halogen atom and a halogenated group;
where R2 is selected from the group of

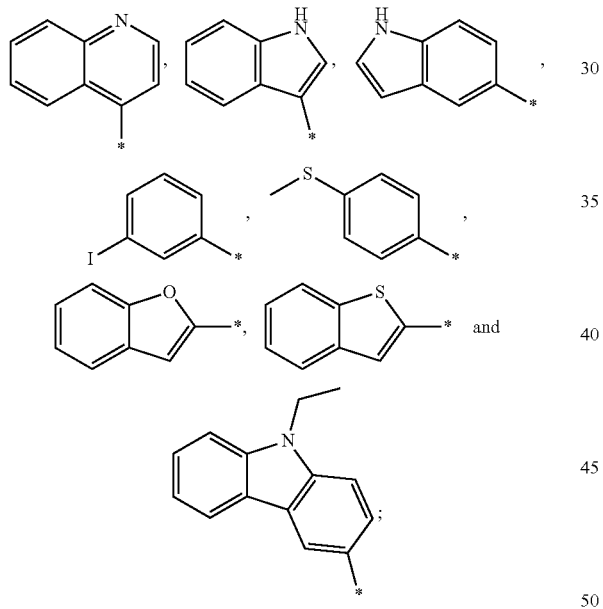

where R3 is a hydrogen atom or

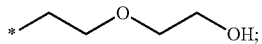 [SMILES: *CCOCCO]

and
where L is a linker group —(CH$_2$)n- where n is an integer from 0-5.

In an embodiment herein, the compound induces chemokine secretion in the tumor microenvironment to promote T cell immune response.

In an embodiment herein, R1 is selected from the group of a hydrogen atom, a fluorine atom and —CF3.

In an embodiment herein, the compound is selected from the group of

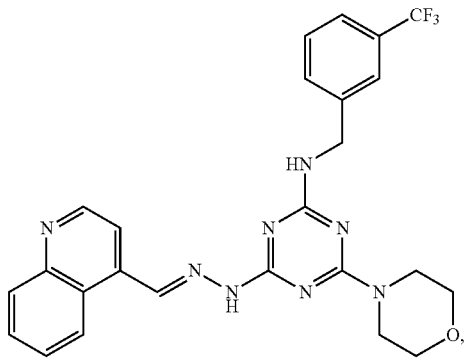

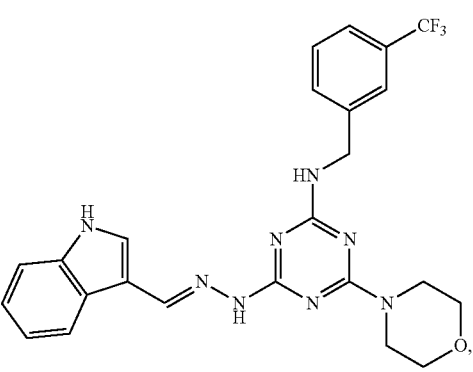

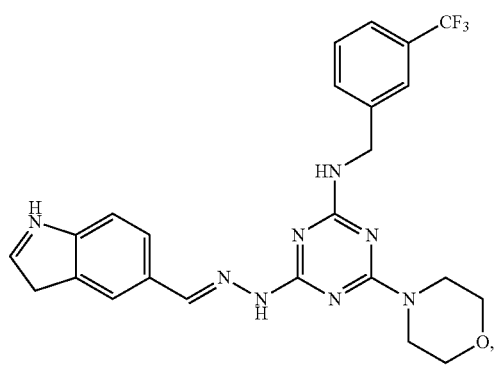

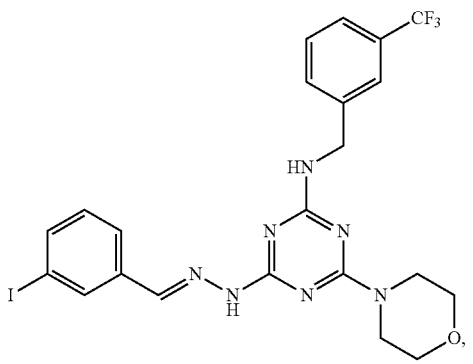

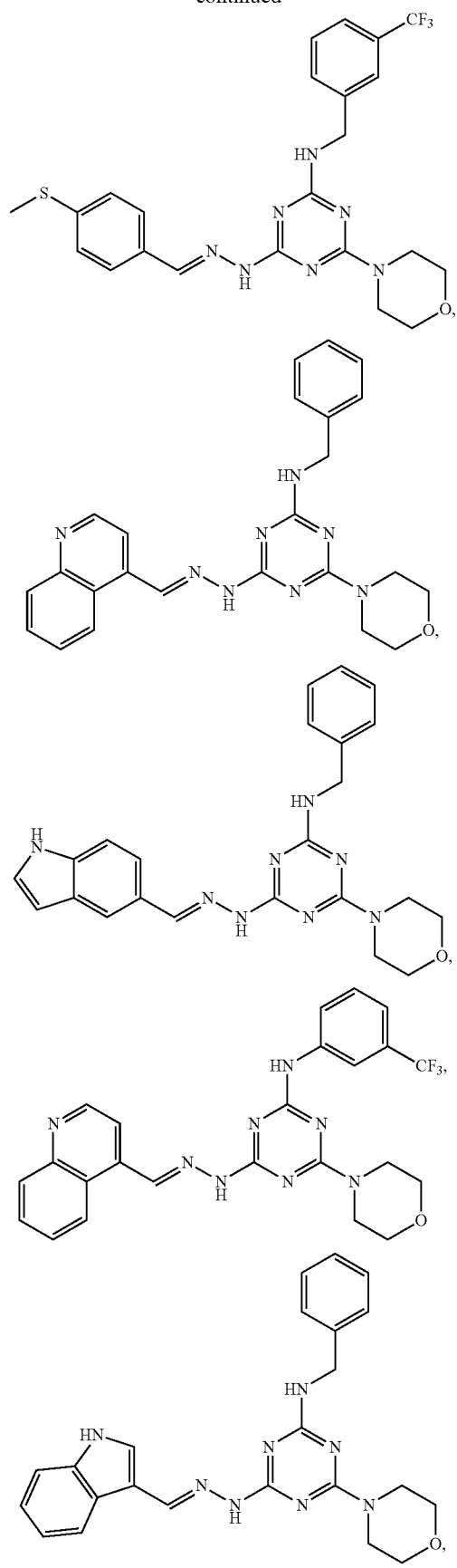
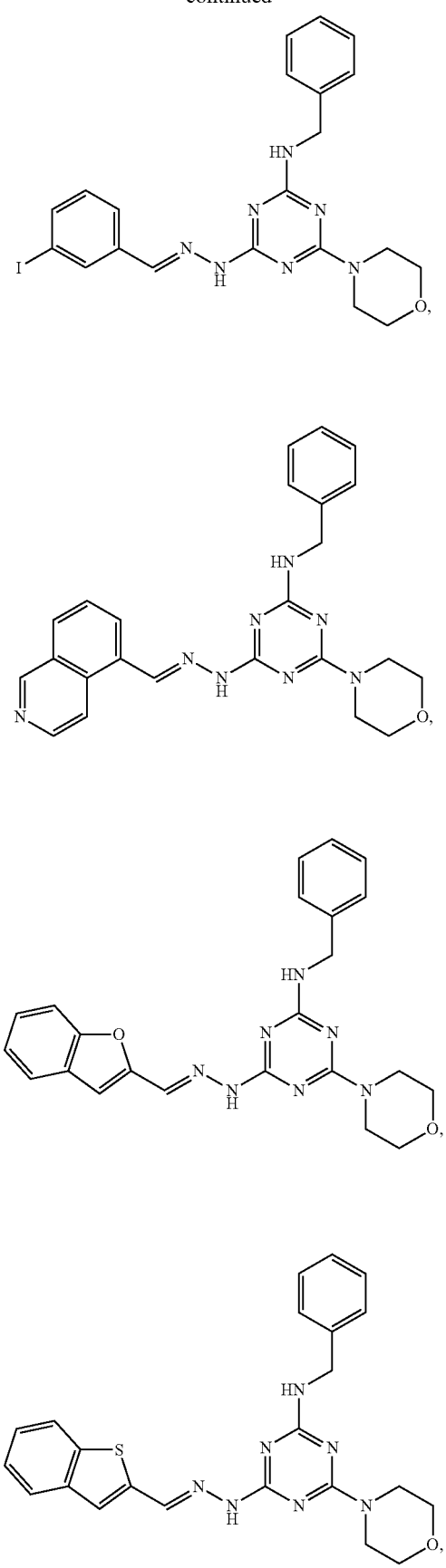

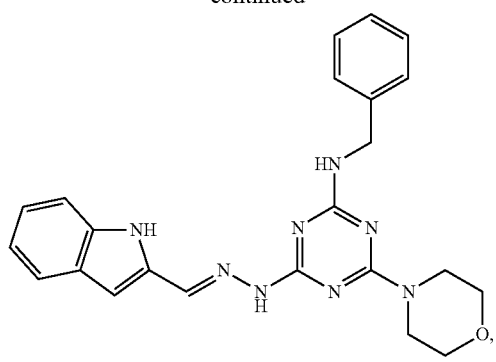
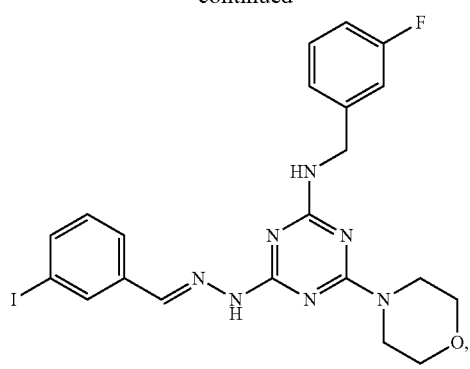
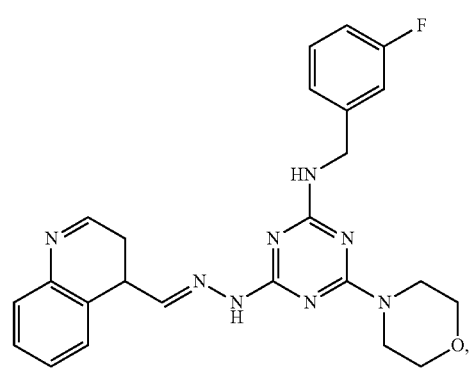
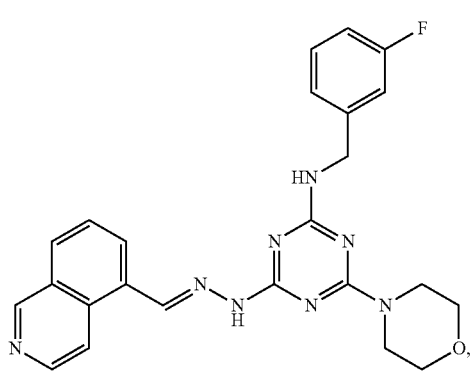
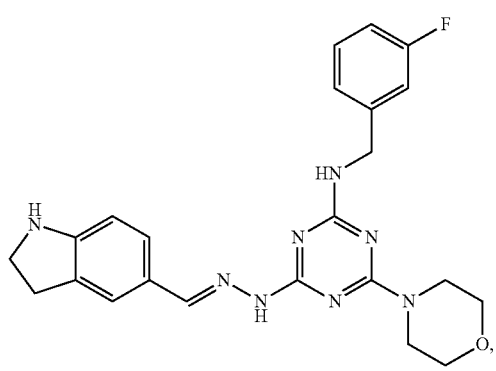
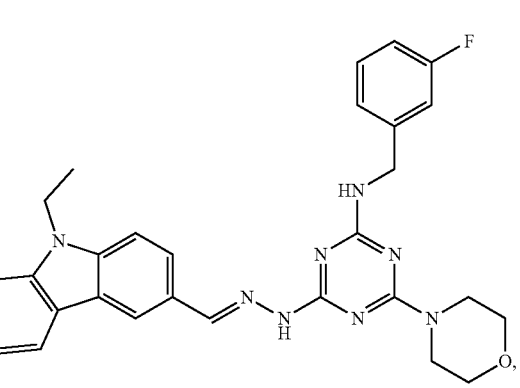
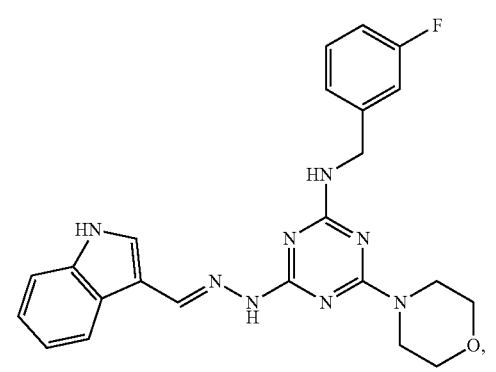
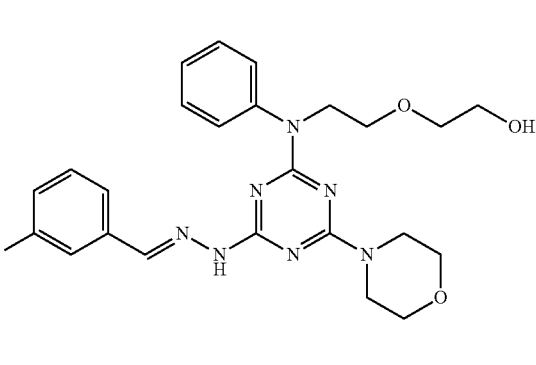
and a combination thereof.

In an embodiment herein the compound is the structure of Formula II (also referred to herein as "6J1") below.

Formula II

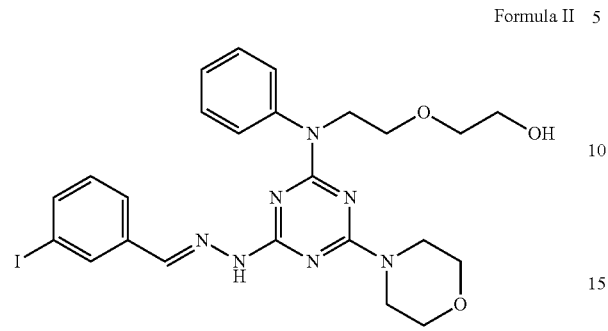

In an embodiment herein, the administering step further includes an exosome secretion inhibitor administered in combination with the compound.

In an embodiment herein, the exosome secretion inhibitor includes GW4869 having the structure of Formula III below.

Formula III

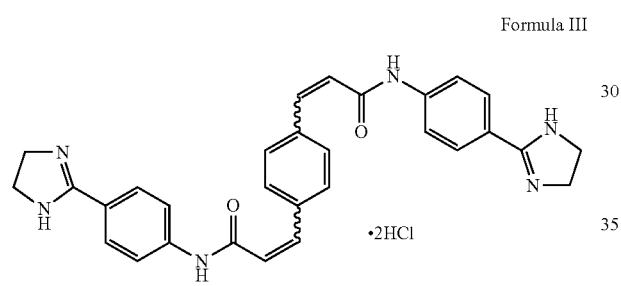

GW4869 can inhibit 6J1-induced PD-L1 exosomal secretion without changing its ability to lock PD-L1 at endocytic vesicles and decrease PD-L1 at the plasma membrane.

In an embodiment herein, the administering step further includes an anti-PD-1 antibody administered in combination with the compound.

In an embodiment herein, the anti PD-1 antibody includes the 29F.1A12 monoclonal antibody.

In an embodiment herein, the cancer is selected from the group of lung cancer, pancreatic cancer, breast cancer, colon cancer, colorectal cancer, melanoma, gastrointestinal cancer, gastric cancer, renal cancer, ovarian cancer, liver cancer, endometrial cancer, kidney cancer, prostate cancer, thyroid cancer, neuroblastoma, glioma, glioblastoma, cervical cancer, stomach cancer, bladder cancer, head and neck cancer, hepatoma, and a combination thereof.

In an embodiment herein, the cancer is selected from the group of cervical cancer, lung cancer, breast cancer, melanoma and a combination thereof.

In an embodiment herein, the cancer is selected from the group of cervical cancer, lung cancer, breast cancer, melanoma and a combination thereof.

Another embodiment herein, a composition to treat a cancer or a tumor, including a compound of Formula I and an anti-PD-1 antibody, Formula I

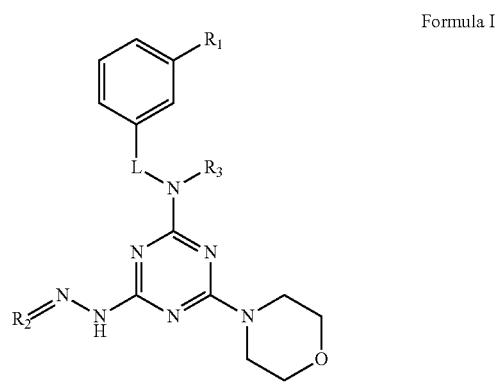

where R1 is selected from the group of a hydrogen atom, a halogen atom and a halogenated group;

where R2 is selected from the group of

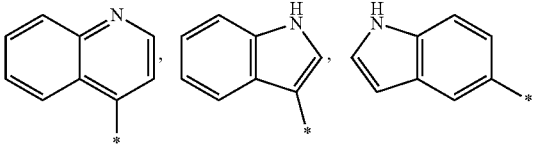

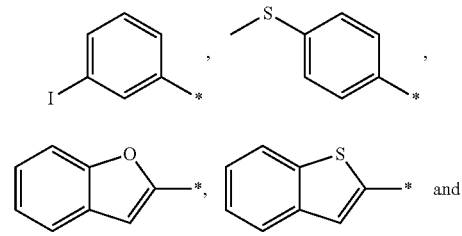

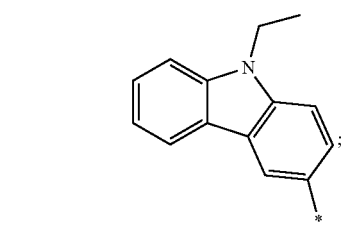

where R3 is a hydrogen atom or

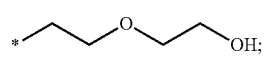

and where L is a linker group —$(CH_2)n$- where n is an integer from 0-5.

In an embodiment herein, the compound is selected from the group of
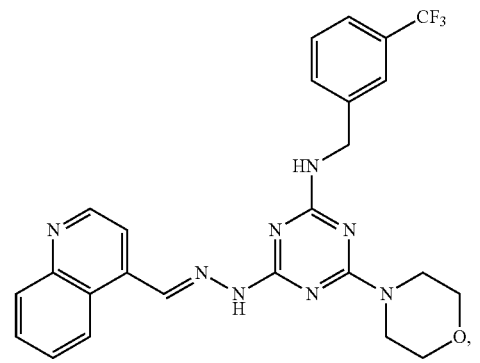
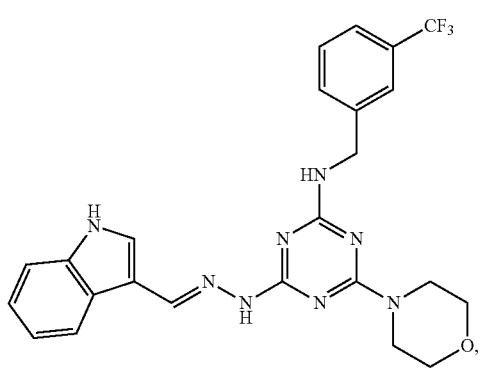
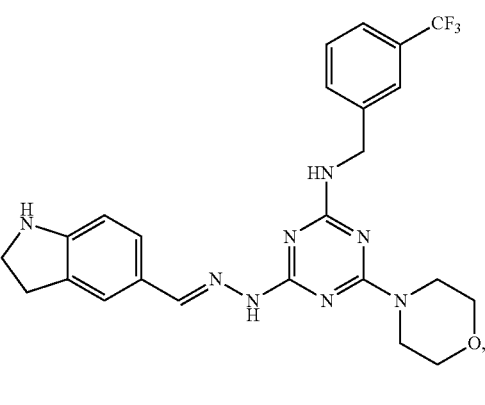
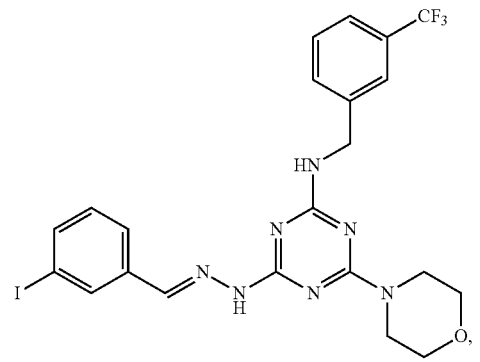
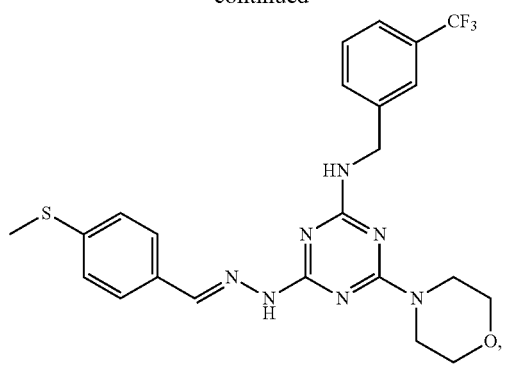
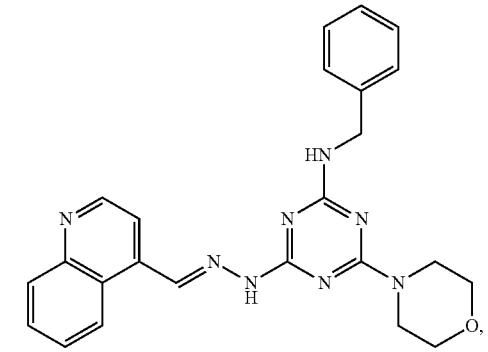
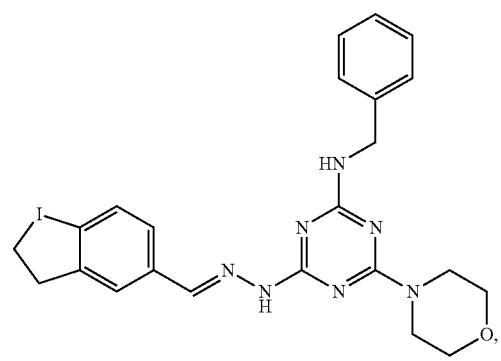
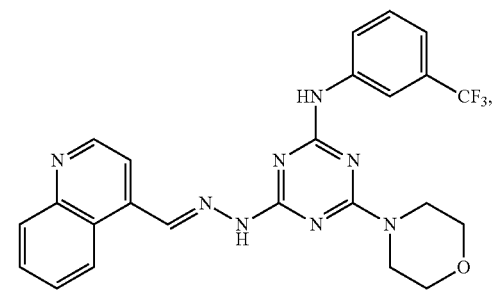
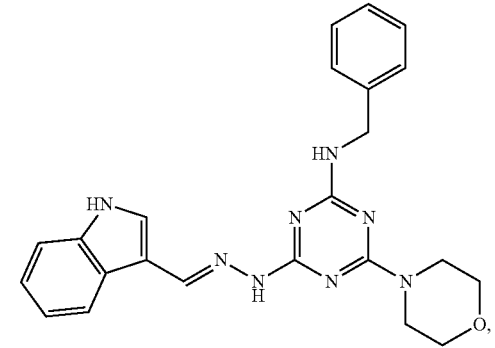

27
-continued
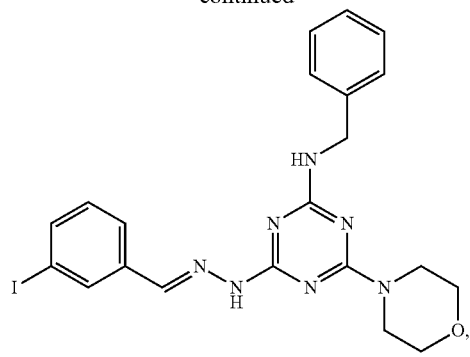
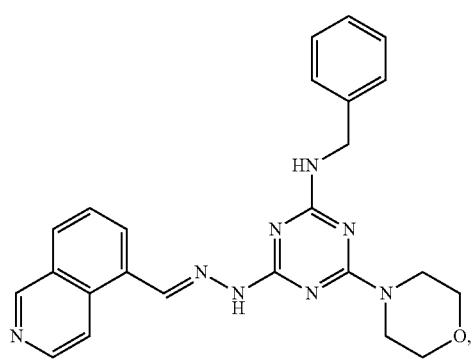
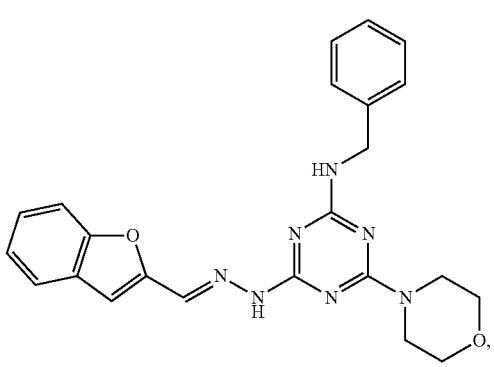
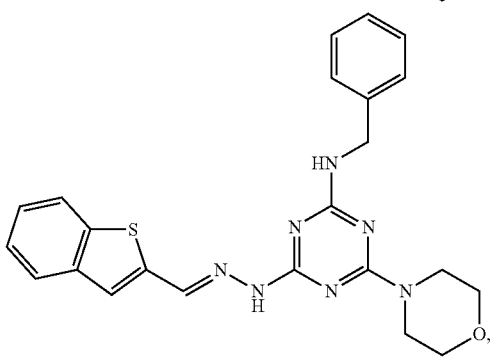
28
-continued
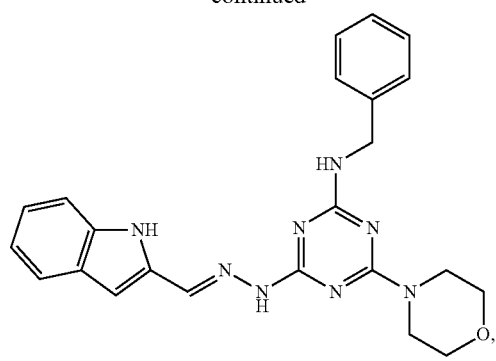
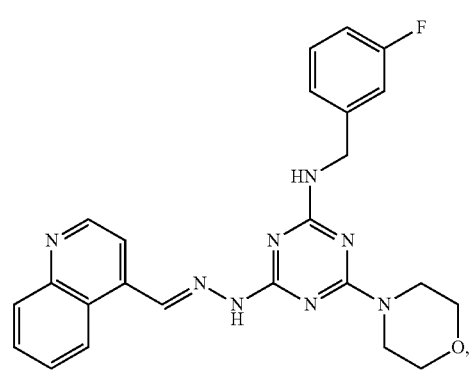
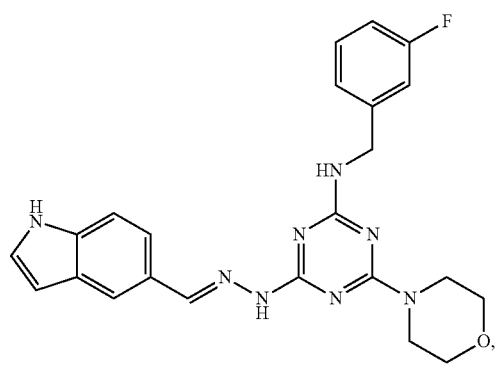
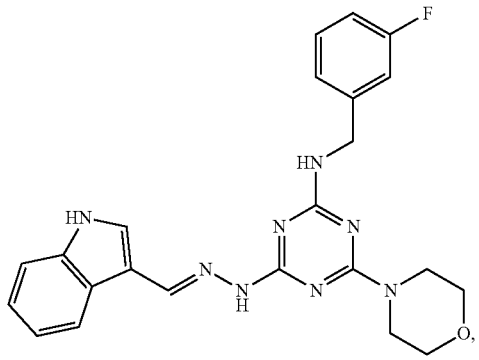

-continued

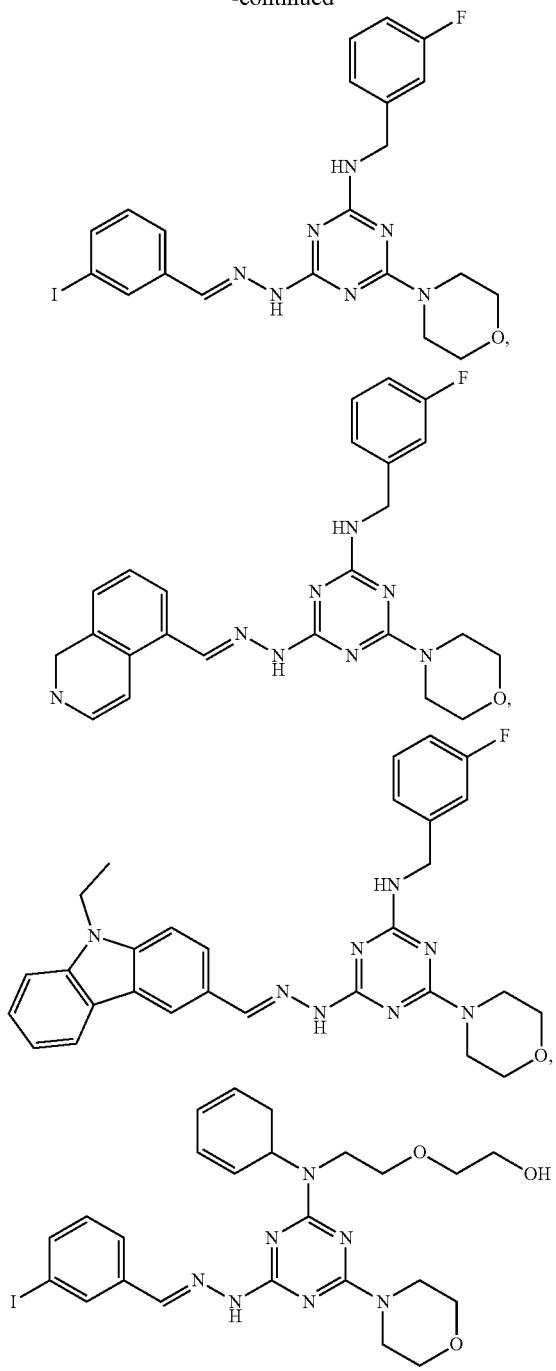

an a combination thereof.

In an embodiment herein, the composition further includes an exosome secretion inhibitor. Exosome secretion inhibitors decrease PD-L1 at the plasma membrane without changing its ability to lock PD-L1 at endocytic vesicles. The combination of the synthesized compounds with GW4869 will significantly promote anti-cancer immunity. (6J1 induced the exosomal secretion of any PD-L1 trapped in the endocytic vesicles, and this increased level of exosomal PD-L1 could still interact with PD-1 in T cells and inhibit their activity. Therefore, the inhibition of exosome secretion by either pharmacological inhibitors or a genetic approach enhances the antitumor efficacy of 6J1) In an embodiment herein, the composition promotes T cell immune response to treat a cancer or a tumor.

Figure 1A:
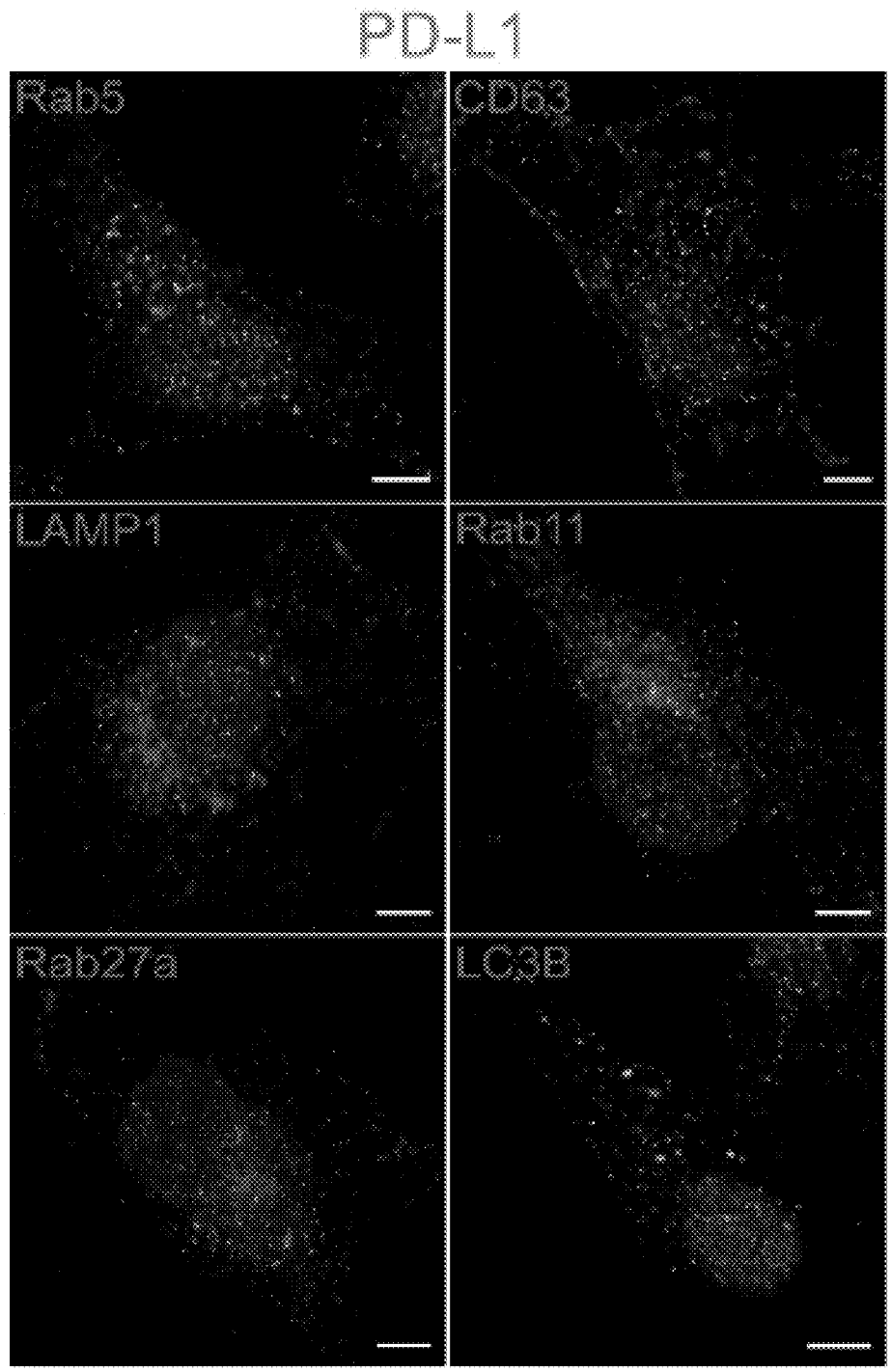
FIG. 1a is a series of fluorescent photographs of cytosol PD-L1 puncta, Rab5, CD63, LAMP1, Rab11, Rab27a, and LC3B colocalization.

Turning to the figures, FIGS. 1a-1e show that the endosomal trafficking of cell surface PD-L1 is clathrin- and RAB5-dependent. FIG. 1a shows that PD-L1 is expressed at both plasma membrane and cytoplasm, and the cytosol PD-L1 puncta exhibited colocalization with Rab5, CD63, LAMP1, Rab11, Rab27a, and LC3B. FIG. 1a suggests that PD-L1 can colocalize with early endosomes, recycling endosomes, MVBs, lysosomes, or/and autophagosomes.

Figure 1B:
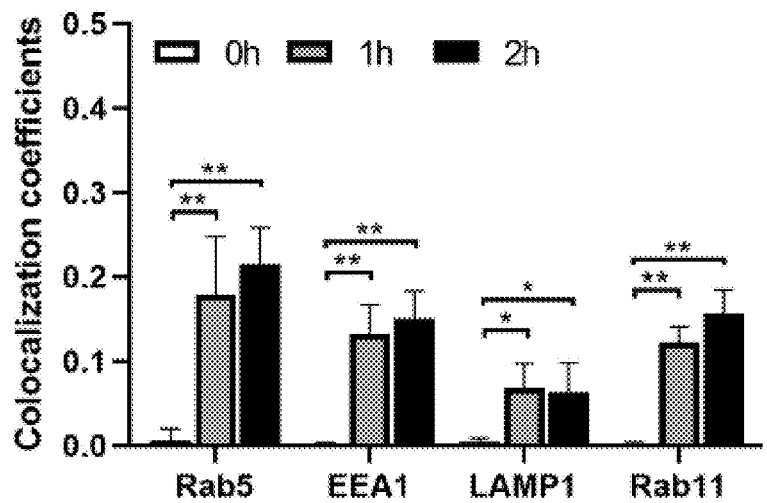
FIG. 1b is a graph showing the quantification of the colocalization of the internalized membrane PD-L1 with RAB5, EEA1, LAMP1, or RAB11.
Figure 1C:
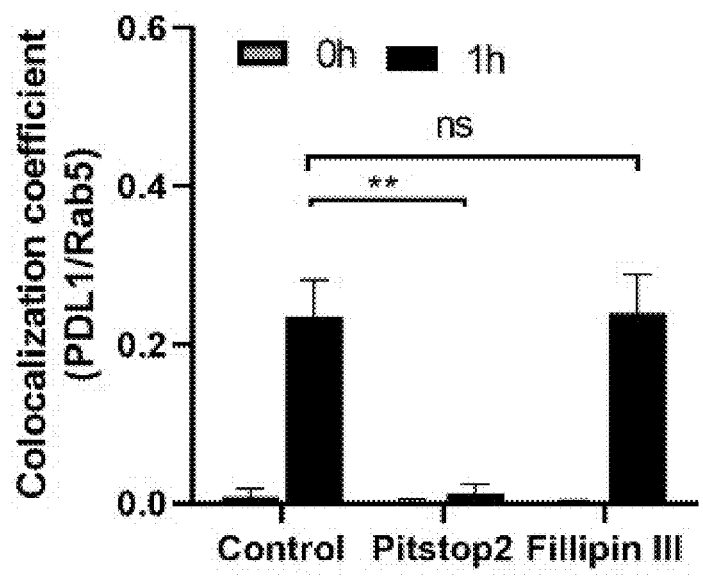
FIG. 1c is a graph showing the quantification of the colocalization of the internalized PD-L1 with Rab5 in cells treated with Pitstop2 or Filipin III.

FIG. 1c shows that the treatment of cells with Pitstop2, an inhibitor of clathrin-dependent endocytosis, blocks the internalization of PD-L1. However, Filipin III, an inhibitor of caveolae-mediated endocytosis, does not affect the internalization of PD-L1.

Figure 1D:
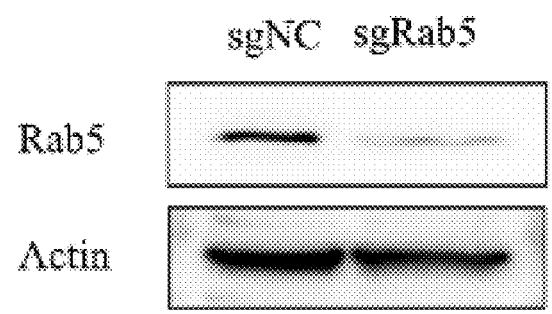
FIG. 1d is a western blot of Rab5 expression in control or Rab5-knockout Hela cells.
Figure 1E:
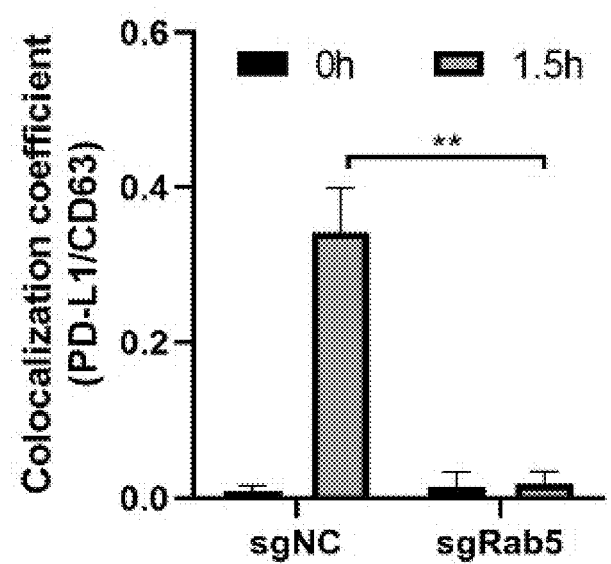
FIG. 1e is a graph showing the quantification of the colocalization of the internalized PD-L1 with CD63 in control or Rab5-knockout Hela cells.

FIGS. 1d and 1e show that RAB5 knockout significantly inhibits the internalization of PD-L1 and blocks its colocalization with CD63.

Figure 2A:
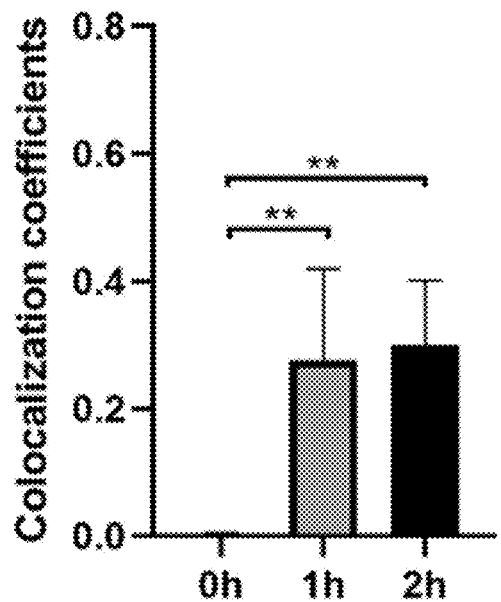
FIG. 2a is a graph showing the quantification of the colocalization between PD-L1 and LC3Bin HeLa cells transfected with LC3B-RFP and stained with the anti-PD-L1 antibody.
Figure 2B:
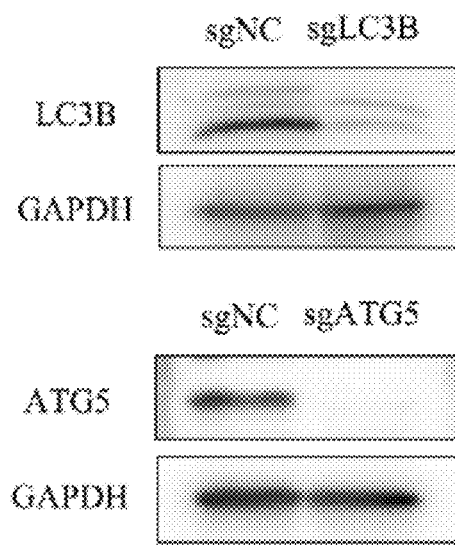
FIG. 2b is a western blot analysis of LC3B or ATG5 in control, LC3B-knockout, or ATG5-knockout HeLa cells.
Figure 2C:
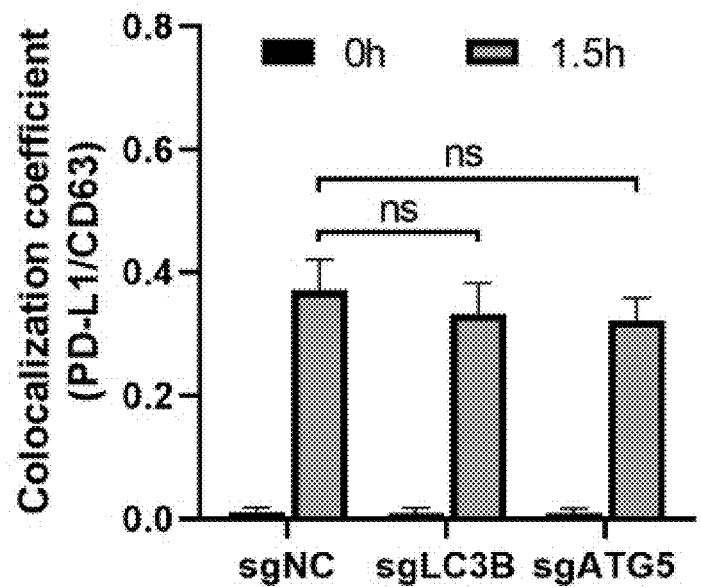
FIG. 2c is a graph showing the quantification of the colocalization of internalized PD-L1 with CD63 in control, LC3B-knockout, or ATG5-knockout HeLa cells transfected with CD63-mcherry and stained with the anti-PD-L1 antibody.
Figure 2D:
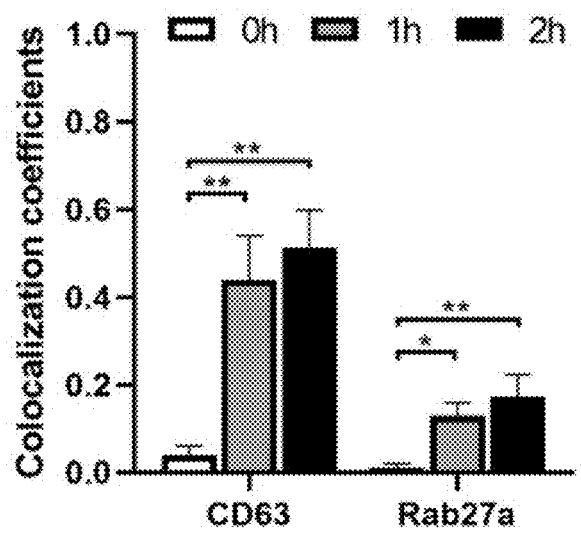
FIG. 2d is a graph showing the quantification of the colocalization of internalized PD-L1 with CD63 or RAB27 of Hela cells stained with PD-L1 antibody and its quantification graph.
Figure 2E:
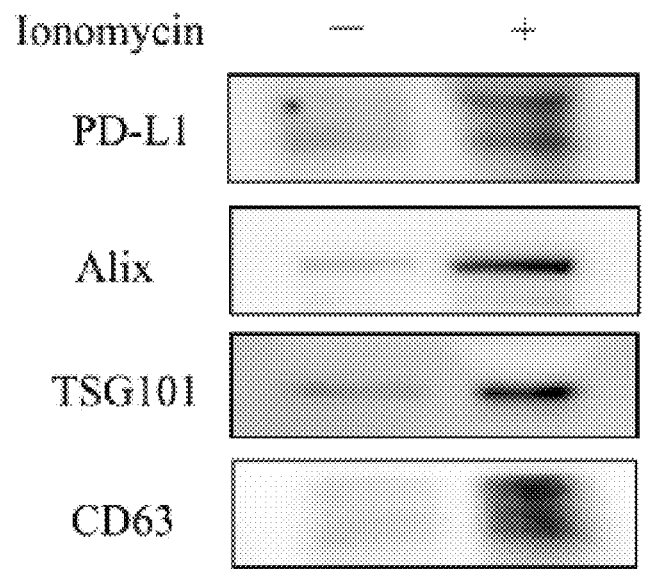
FIG. 2e is a western blot analysis of PD-L1, Alix, TSG101, and CD63 in exosomes isolated from cells treated with or without ionomycin (1 µM) for 48 h.
Figure 2F:
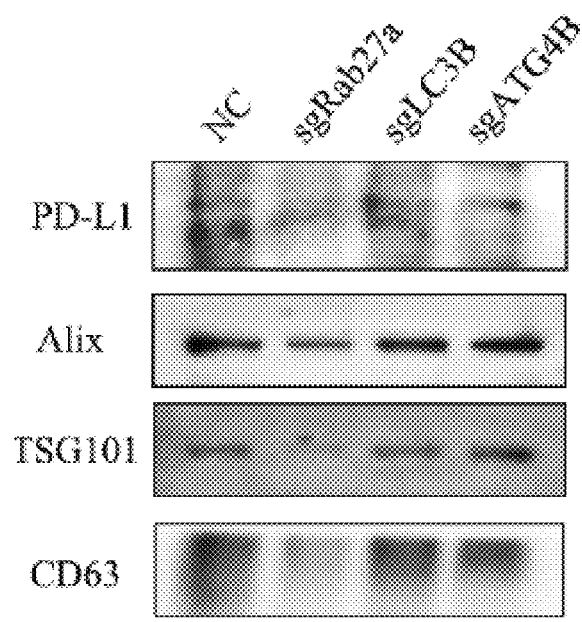
FIG. 2f is a western blot analysis of PD-L1, Alix, TSG101, and CD63 in exosomes isolated from control, Rab27A-, LC3B-, or ATG4B-knockout cells.
Figure 2G:
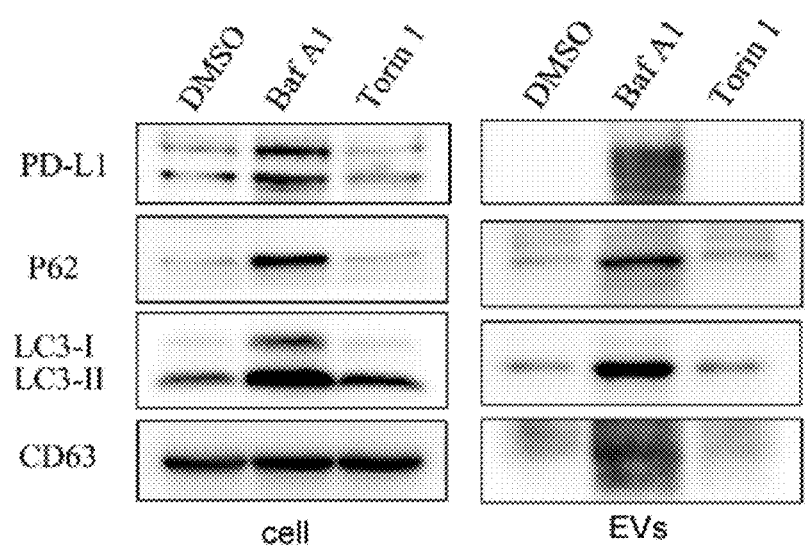
FIG. 2g is a western blot analysis of PD-L1, p62, and LC3 in total cell lysates or exosomes isolated from HeLa cells treated with or without Bafilomycin A1 (10 nM) or Torin 1 (100 nM) for 48 h.

FIGS. 2a-2g show autophagy is not essential for PD-L1 endosomal trafficking and exosomal secretion. On the other hand, blockage on the fusion between lysosomes and late endosomes or autophagosomes may induce PD-L1 secretion via exosomes. FIG. 2a shows internalized PD-L1 also exhibits strong colocalization with LC3B. FIGS. 2b and 2c show LC3B knockout or ATG5-knockout do not affect the PD-L1's internalization and its association with CD63. It suggests that PD-L1's endosomal trafficking is independent of autophagy. FIG. 2d shows that the internalized PD-L1 exhibits strong colocalization with CD63 and RAB27. FIG. 2e shows that PD-L1 is detected in the exosomes, and ionomycin, a calcium ionophore, induces exosome secretion and markedly increases the exosomal PD-L1 level. FIG. 2f shows that LC3B or ATG4B knockout does not affect exosomal PD-L1 levels. However, RAB27A knockout markedly reduces the exosomal PD-L1 level. FIG. 2g shows that bafilomycin A1 (BafA1) markedly increases the total PD-L1 level in cells and the exosomal PD-L1 level. However, Torin1, an autophagy activator, has little effect on total and exosomal PD-L1 levels.

Figure 3A:
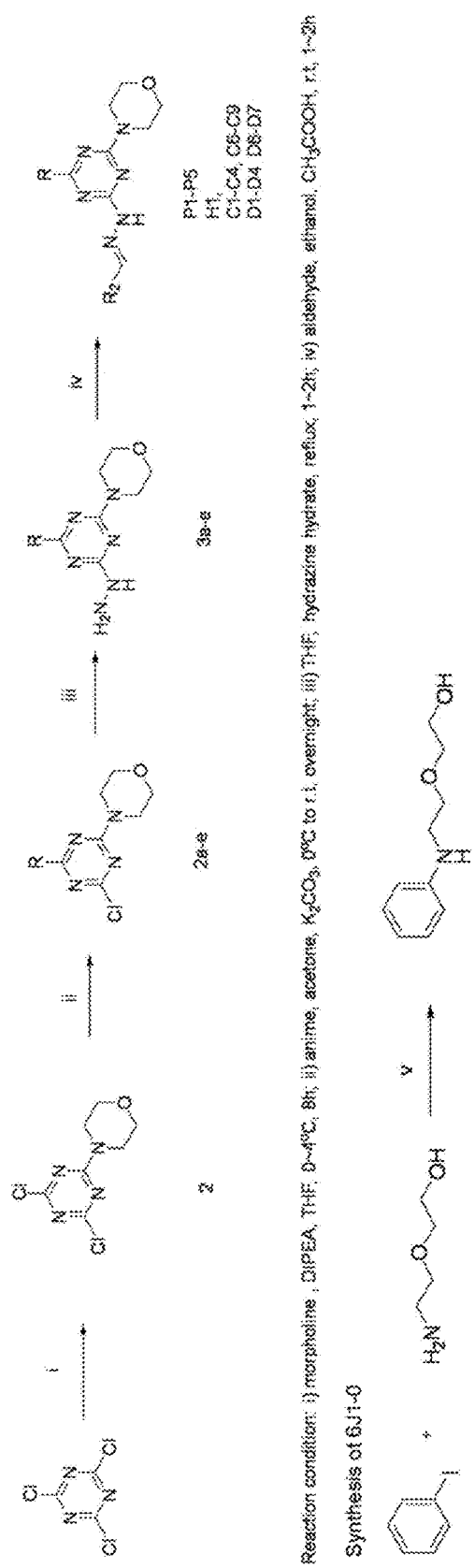
FIG. 3a is a synthesis route of 6-morpholine-1,3,5-triazine derivatives.

FIG. 3a shows the synthetic scheme of 6-morpholine-1,3,5-triazine derivatives. The starting material is 2,4,6-trichloro-1,3,5-triazine. After reacting with morpholine in the presence of DIPEA in THF at 0-4° C. for 8 h, compound 2 is obtained. Different amines are introduced into compound 2 by $K_2CO_3$ in acetone at from 0° C. to room temperature overnight to give compounds 2a-2e. Among them, 6J1-0, the amine of 6J1, is prepared in water by iodobenzene and 2-(2-aminoethoxy)ethan-1-ol catalyzed by CuI (10% mol) and $K_2COc_3$ at 80° C. overnight. Then, compounds 2a-2e are refluxed with hydrazine hydrate in THF for 1-2 h, to give compounds 3a-3e. Compounds P1-P5, H1, 6J1, C1-C4, C6-C9, DI-D4 and D6-D7 are prepared by reaction with different aldehydes and acetic acid in ethanol at room temperature for 1-2 h.

Figure 3B:
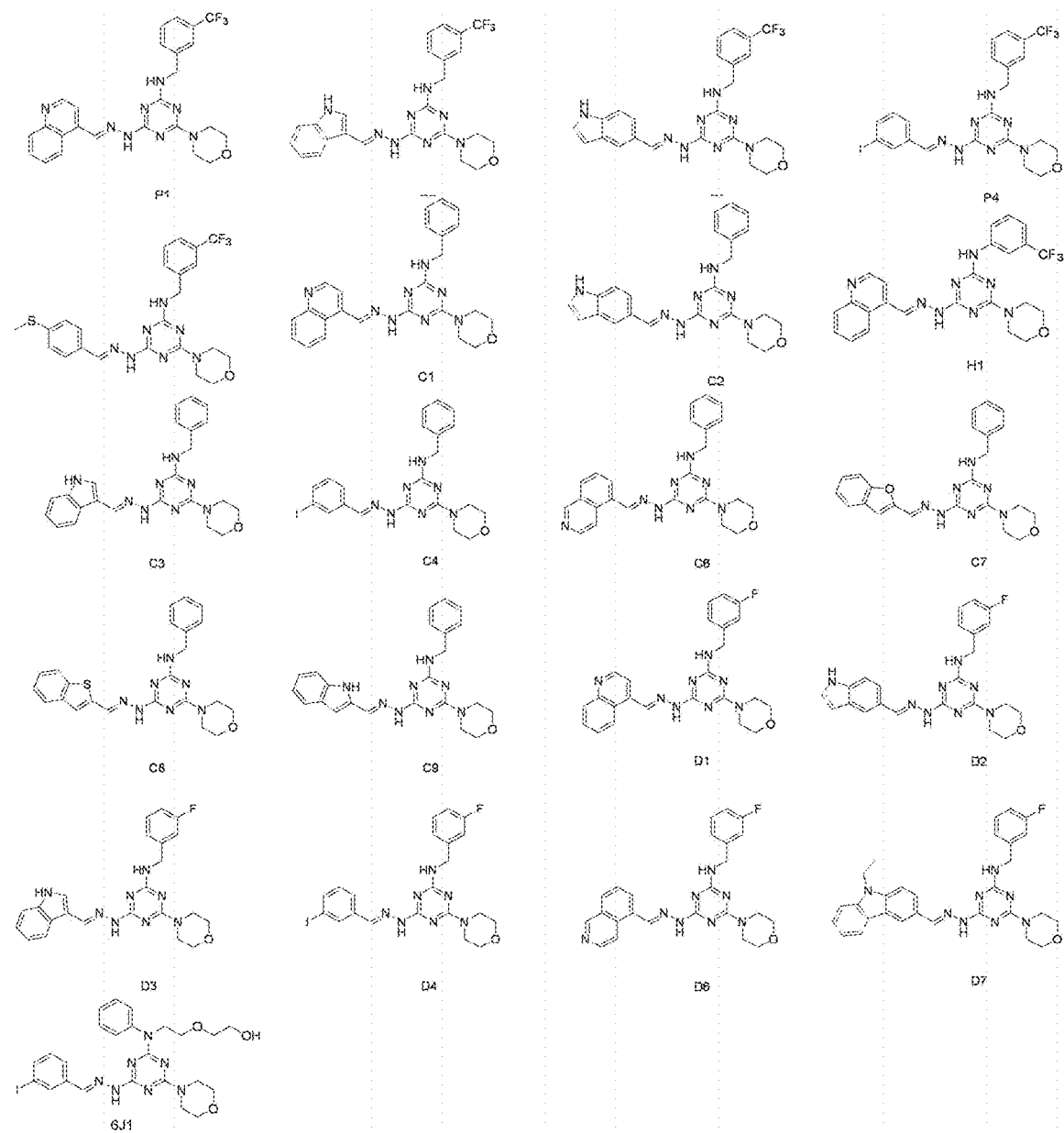
FIG. 3b is a variety of chemical structures of synthesized 6-morpholine-1,3,5-triazine derivatives.

FIG. 3b shows chemical structures of 21 synthesized 6-morpholine-1,3,5-triazine derivatives according to FIG. 3a.

Figure 4A:
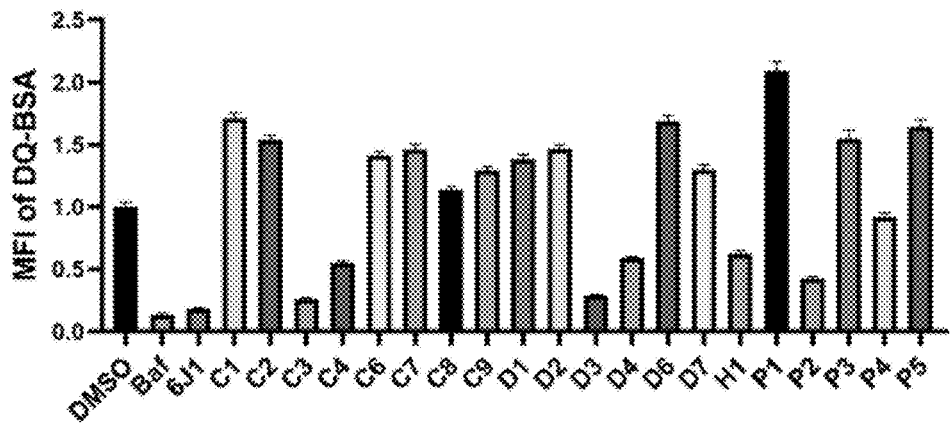
FIG. 4a is a graph showing the mean fluorescence intensities of DQ-BSA of cells treated with all synthesized derivatives.

FIG. 4a shows that compounds 6J1, C3, C4, D3, D4, H1, and P2 dramatically inhibit endocytic trafficking, manifested by their ability to inhibit the fluorescence intensity of DQ-BSA-labeled cells.

Figure 4B:
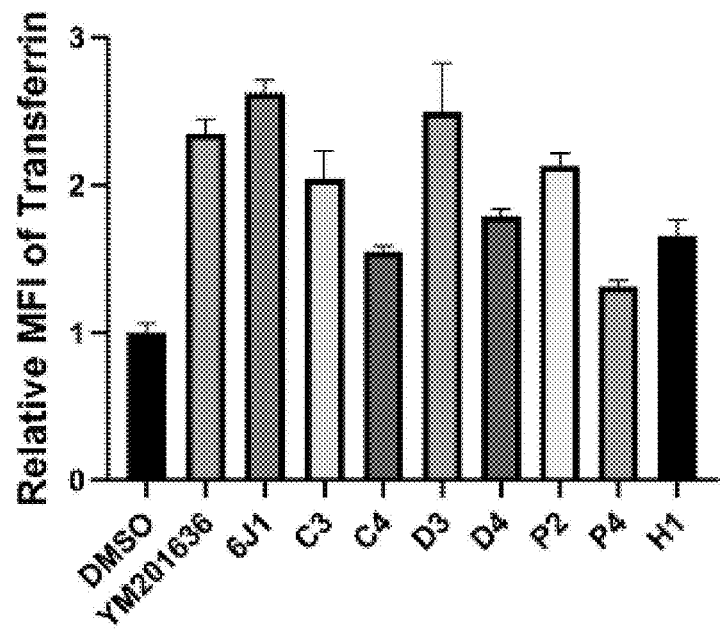
FIG. 4b is a graph showing the mean fluorescence intensities of transferrin of cells treated with compound 6J1, C3, C4, D3, D4, P2, P4, and H1 in flow cytometry analysis.

FIG. 4b shows that compounds 6J1, C3, C4, D3, D4, P2, P4, and H1 effectively inhibit the recycling endosomal trafficking of transferrin. Among them, 6J1 performs best.

Figure 4C:
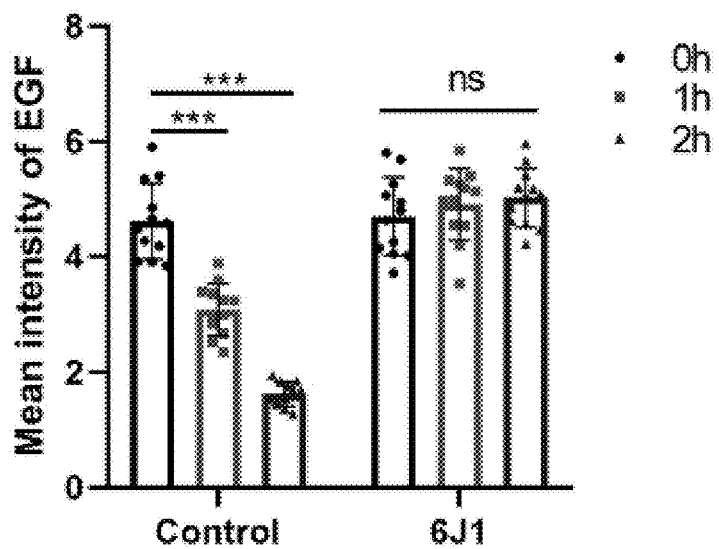
FIG. 4c is a graph showing the mean of intensity of EGFR of 6J1-treated cells and the control after 1 h and 2 h of EGF treatment.

FIG. 4c shows that 6J1 blocks the EGFR degradation, manifested by locking the EGFR complex on the endosomes in 6J1-treated cells after 2 h of EGF treatment compared to the control cells in which the EGFR has wholly degraded after 2 h of EGF treatment.

Figure 4D:
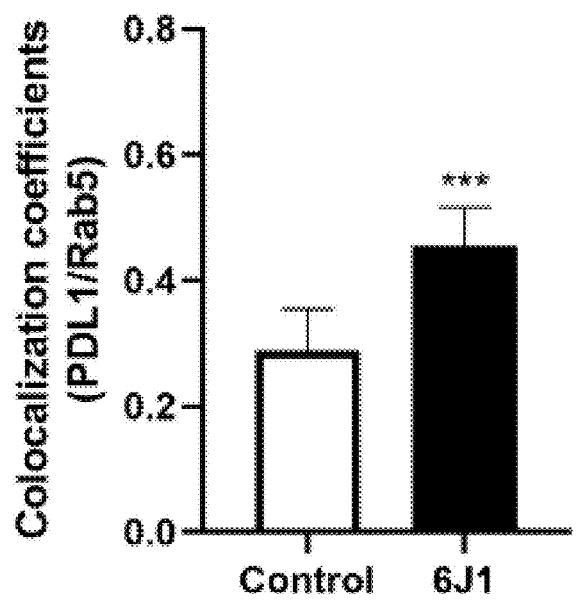
FIG. 4d is a graph showing the quantification of the PD-L1/Rab5 colocalization in the PD-L1-GFP stable expressing HeLa cells treated with or without 6J1 (1 µM).
Figure 4E:
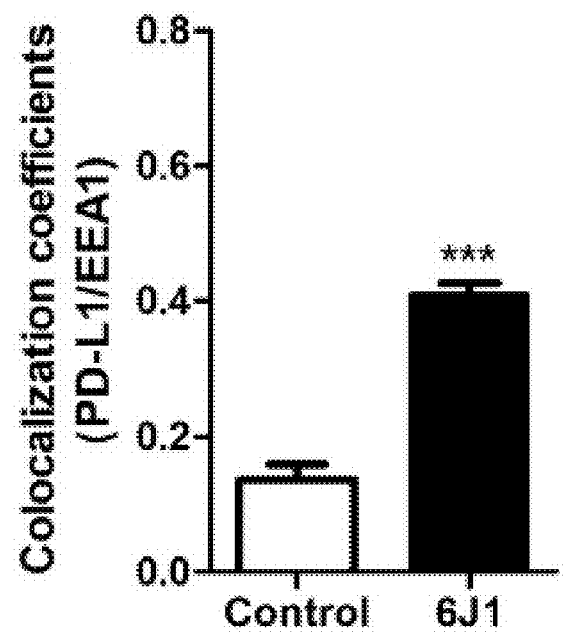
FIG. 4e is a graph showing the quantification of the PD-L1/EEA1 colocalization in the PD-L1-GFP stable expressing HeLa cells treated with or without 6J1 (1 µM).

FIGS. 4d and 4e show that 6J1 treatment clearly induces the accumulation of PD-L1 within vesicle-like structures in the cytoplasm, and these vesicles colocalized with the early endosome markers, EEA1 and RAB5.

Figure 4F:
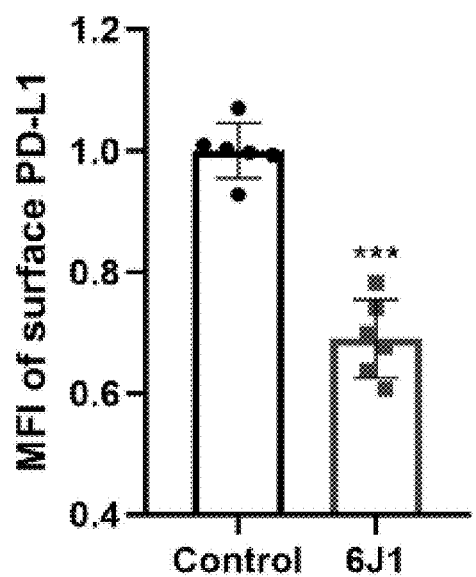
FIG. 4f is a graph showing the flow cytometry-based quantification of plasma membrane levels of PD-L1 in HeLa cells treated with or without 6J1 (1 µM) for 24 h.
Figure 4G:
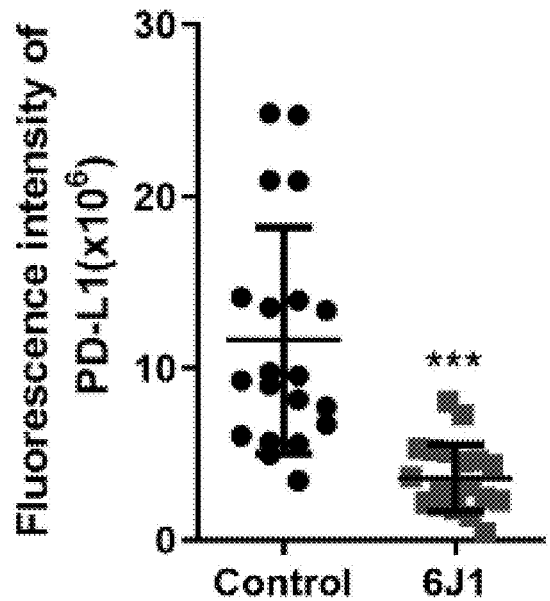
FIG. 4g is a graph showing the fluorescence intensities of PD-L1-GFP-expressing HeLa cells treated with or without 6J1 (1 µM) for 24 h, and the membrane PD-L1-GFP is quantified

FIGS. 4f and 4g show that 6J1 significantly reduces the expression of PD-L1 on the surface of cells.

Figure 5A:
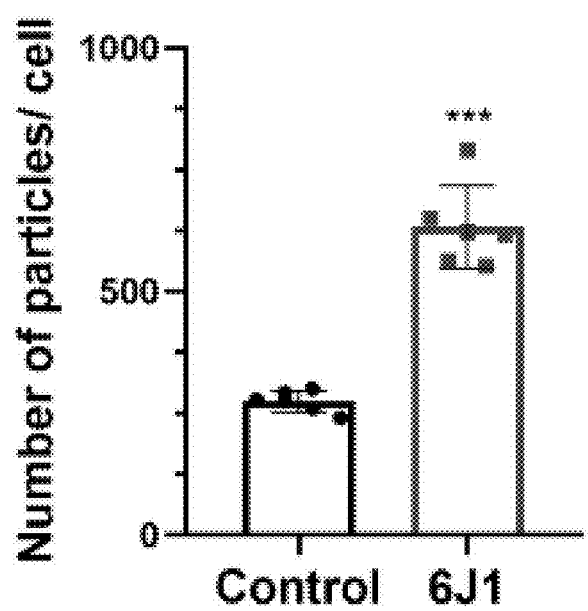
FIG. 5a is a graph showing the concentrations of extracellular vesicles of Hela cells treated with or without 6J1 using a Nanosight nanoparticle analyzer.
Figure 5B:
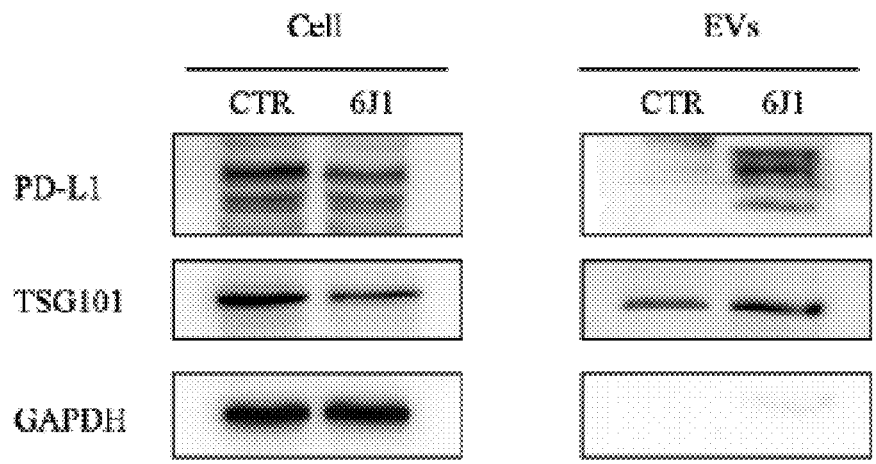
FIG. 5b is a western blot analysis of PD-L1 and TSG101 in total cell lysates or exosomes isolated from the HeLa cells treated with or without 6J1 (1 µM) for 48 h.
Figure 5C:
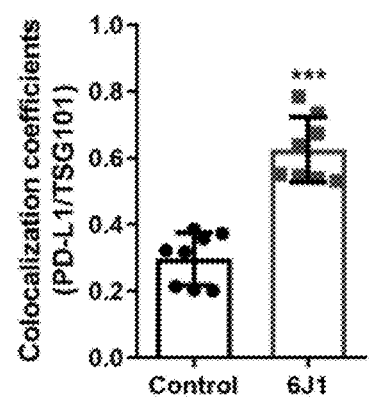
FIG. 5c is a graph showing the quantification of the colocalization of PD-L1 with TSG101 in PD-L1-GFP-expressing HeLa cells transfected with TSG101-mcherry treated with or without 6J1 (1 µM) for 24 h.
Figure 5D:
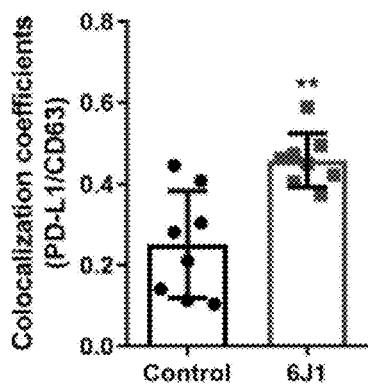
FIG. 5d is a graph showing the quantification of the colocalization of PD-L1 with CD63 in PD-L1-GFP-expressing HeLa cells transfected with CD63-mcherry treated with or without 6J1 (1 µM) for 24 h.
Figure 5E:
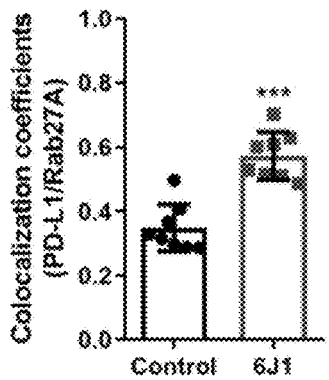
FIG. 5e is a graph showing the quantification of the colocalization of PD-L1 with Rab27a in PD-L1-GFP-expressing HeLa cells transfected with RAB27A-mcherry treated with or without 6J1 (1 µM) for 24 h.
Figure 5F:
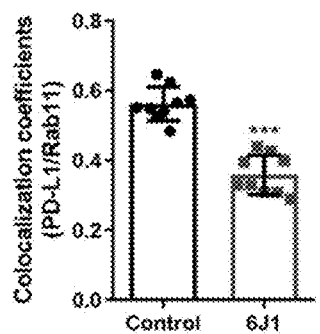
FIG. 5f is a graph showing the quantification of the colocalization of PD-L1 with Rab11 in PD-L1-GFP-expressing HeLa cells transfected with RAB11-mcherry treated with or without 6J1 (1 µM) for 24 h.
Figure 5G:
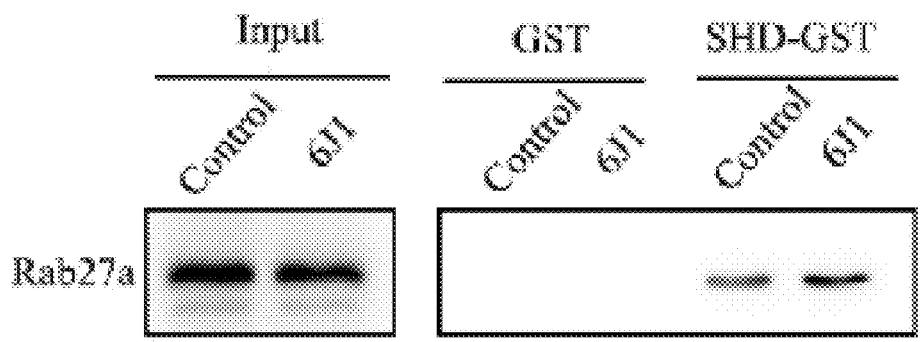
FIG. 5g is a western blot analysis of Rab27a in HeLa cells treated with or without 6J1 (1 µM) through a GST-SHD pulldown assay.
Figure 5H:
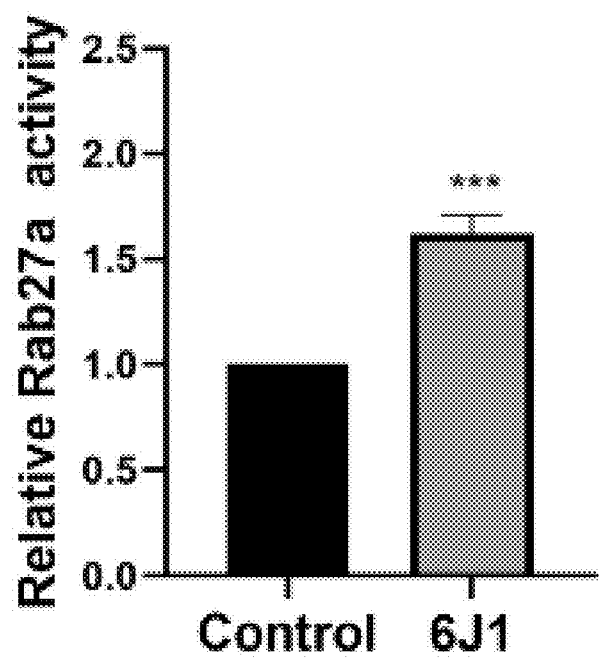
FIG. 5h is a graph showing the relative activities of Rab27a in HeLa cells treated with or without 6J1 (1 µM) through a GST-SHD pulldown assay.
Figure 6A:
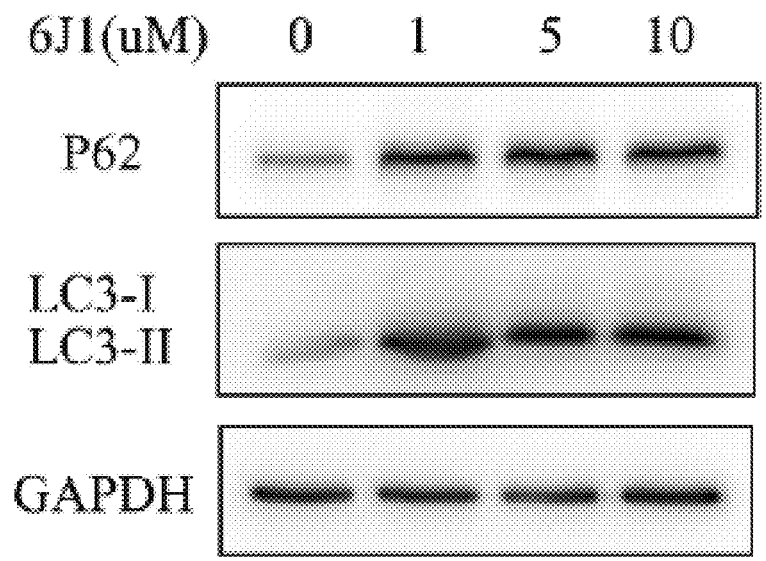
FIG. 6a is a western blot analysis of LC3 and p62 in HeLa cells treated with or without 6J1.
Figure 6B:
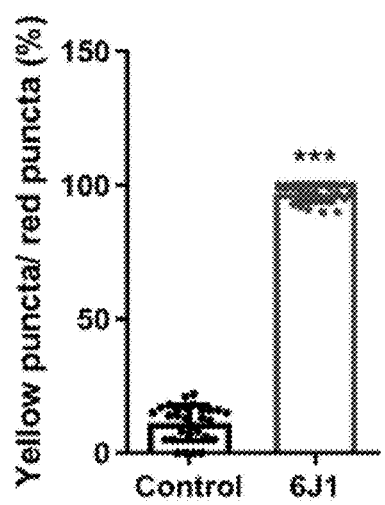
FIG. 6b is the quantification of LC3 yellow puncta in GFP-RFP-LC3-expressing HeLa cells treated with or without 6J1 (1 µM) for 6 h.

FIGS. 5a and 5b show 6J1 dramatically induces exosome secretion and increased PD-L1 level in exosomes by Nanosight nanoparticle analysis and western blot analysis. FIGS. 5c-5e show that 6J1 significantly induces the colocalization of PD-L1 with the exosomal markers, e.g., TSG101, CD63, and Rab27A. FIG. 5f shows that 6J1 markedly decreases the colocalization between PD-L1 and RAB11 (the recycling endosome marker). FIGS. 5g-5h show that compound 6J1 significantly increases the activity of Rab27a-GTPase, which may contribute to the increased exosome secretion in 6J1-treated cells. These results indicate that 6J1 can increase Rab27a-GTPase activity to promote exosomal PD-L1 secretion FIG. 6a shows 6J1 also markedly induces an increase in the level of LC3B-II and P62. 5 FIG. 6b shows 6J1 significantly induced the formation of yellow LC3B puncta in GFP-RFP-LC3-expressing HeLa cells, and no red-only LC3B puncta are observed in 6J1-treated cells. These results suggest that 6J1 inhibits the autophagosome and lysosome fusion.

Figure 6C:
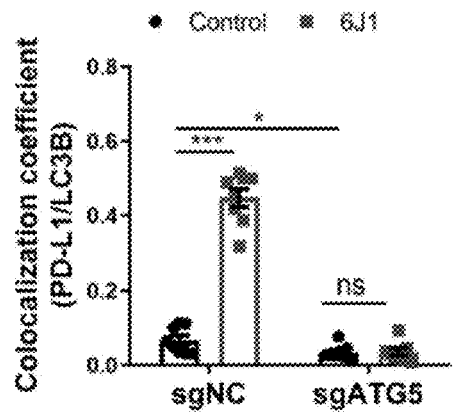
FIG. 6c is a graph showing PD-L1/LC3B colocalization quantification in control or ATG5-knockout HeLa cells transfected with PD-L1-GFP and LC3-RFP and treated with or without 6J1 (1 µM) for 24 h.
Figure 6D:
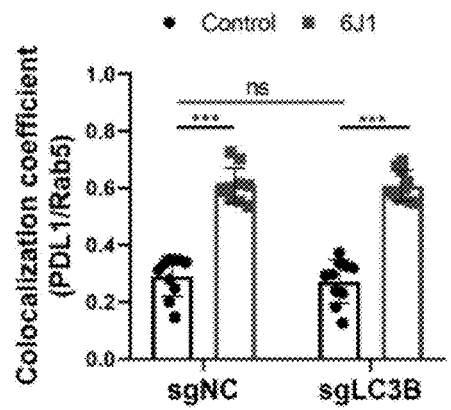
FIG. 6d is a graph showing PD-L1/Rab5 colocalization quantification in control or LC3B-knockout HeLa cells transfected with PD-L1-GFP and treated with or without 6J1 (1 µM) for 24 h.
Figure 6E:
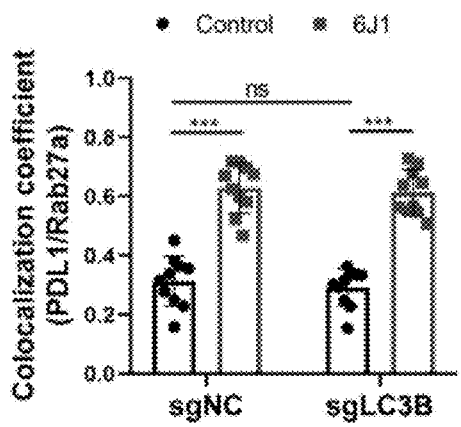
FIG. 6e is a graph showing PD-L1/Rab27 colocalization quantification in control or LC3B-knockout HeLa cells transfected with PD-L1-GFP and treated with or without 6J1 (1 µM) for 24 h.

FIG. 6c shows that PD-L1-containing vesicles strongly colocalize with LC3B puncta in 6J1-treated cells. ATG5 knockout significantly reduces LC3B punta and abolishes this colocalization between PD-L1 and LC3B on the cells treated with 6J1 yet has no effect on 6J1-induced PD-L1 puncta. FIGS. 6d and 6e show that LC3B knockout does not affect the 6J1-induced PD-L1 puncta and the colocalization between PD-L1 and RAB5 or RAB27A. These results indicate that autophagy is not required for 6J1-mediated PD-L1 trafficking.

Figure 7A:
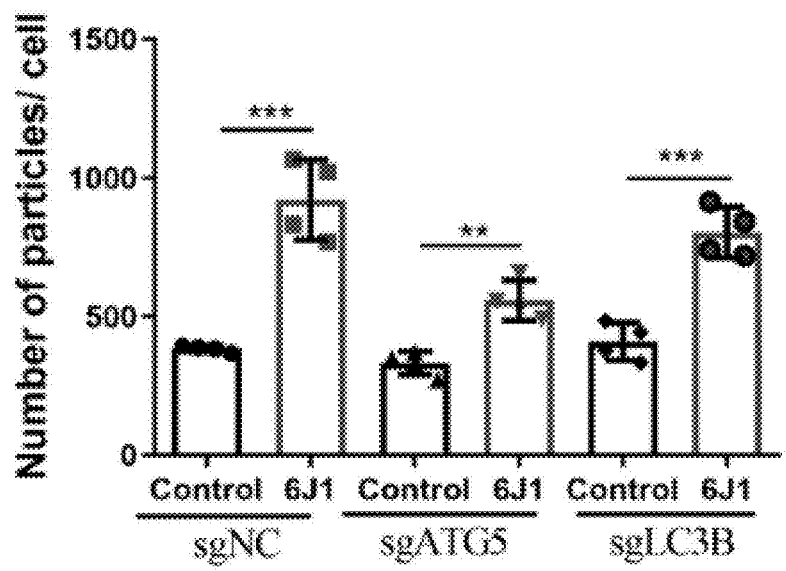
FIG. 7a is a graph showing the numbers of extracellular vesicles collected from ATG5- or LC3-knockout HeLa cells treated with or without 6J1 (1 µM) for 24 h.
Figure 7B:
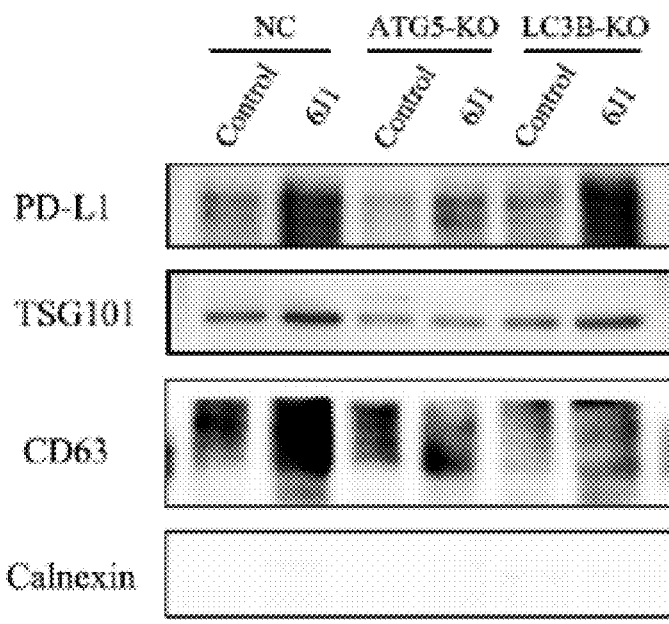
FIG. 7b is a western blot analysis of PD-L1, TSG101, CD63 and Calnexin in the exosomes collected from control, ATG5- or LC3-knockout HeLa cells treated with or without 6J1 (1 µM) for 24 h.
Figure 7C:
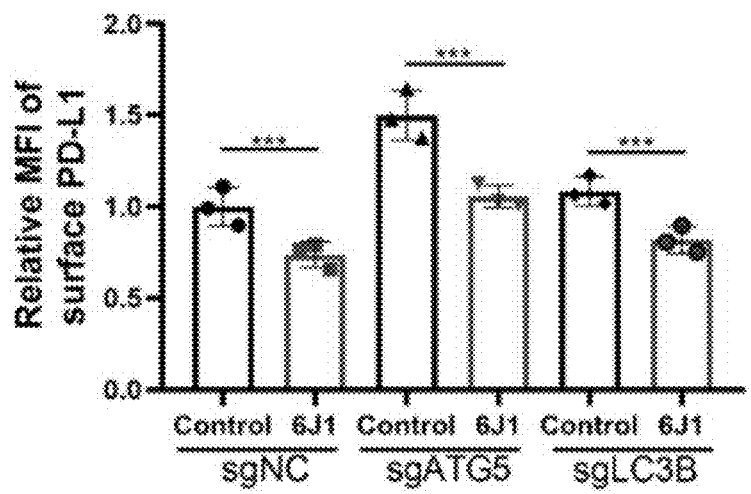
FIG. 7c is a graph showing the relative mean fluorescence intensities based on flow cytometry analysis of PD-L1 at the surface of control, ATG5-knockout or LC3-knockout HeLa cells treated with or without 6J1 (1 µM) for 24 h.

FIGS. 7a-7c show that neither ATG5 nor LC3B knockout impairs the 6J1-induced EVs secretion, exosomal PD-L1 secretion, and the decrease in the level of PD-L1 at the cell surface respectively.

Figure 7D:
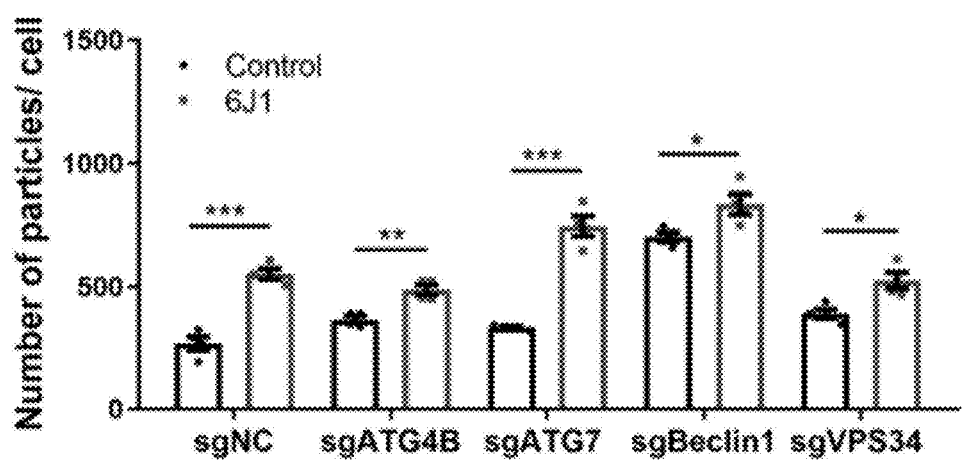
FIG. 7d is a graph showing the numbers of extracellular vesicles of the exosomes of the EVs marker and PD-L1 collected from control, ATG4B-knockout, ATG7-knockout, Beclin1-knockout, or VPS34-knockout HeLa cells treated with or without 6J1 (I µM) for 24 h.
Figure 7E:
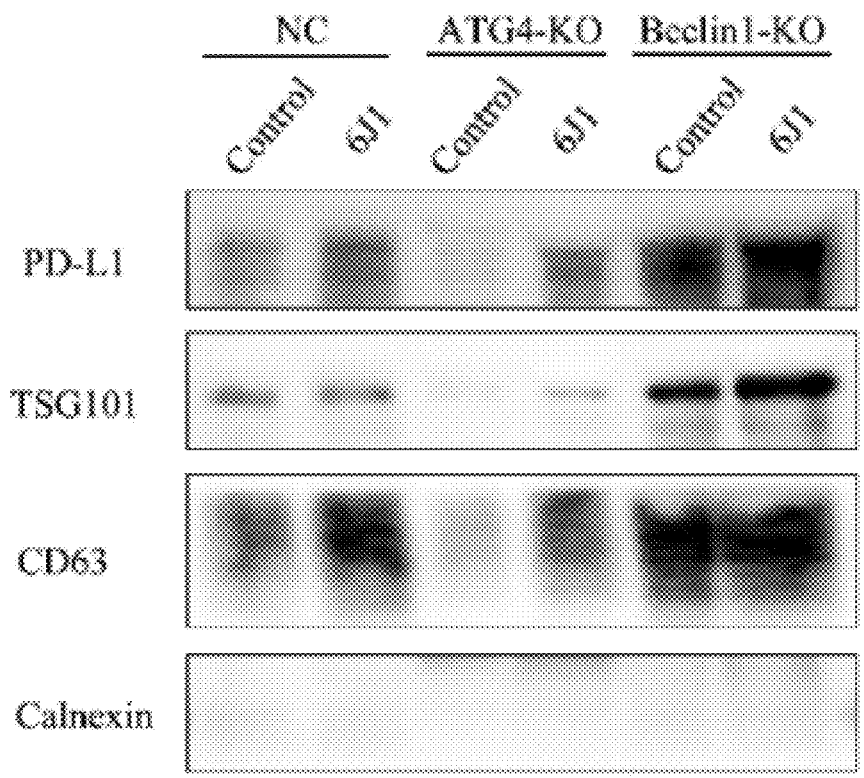
FIG. 7e is a western blot analysis of PD-L1 and the EVs markers in the exosomes collected from control, ATG4B-knockout, or Beclin1-knockout HeLa cells treated with or without 6J1 (1 µM) for 24 h.
Figure 7F:
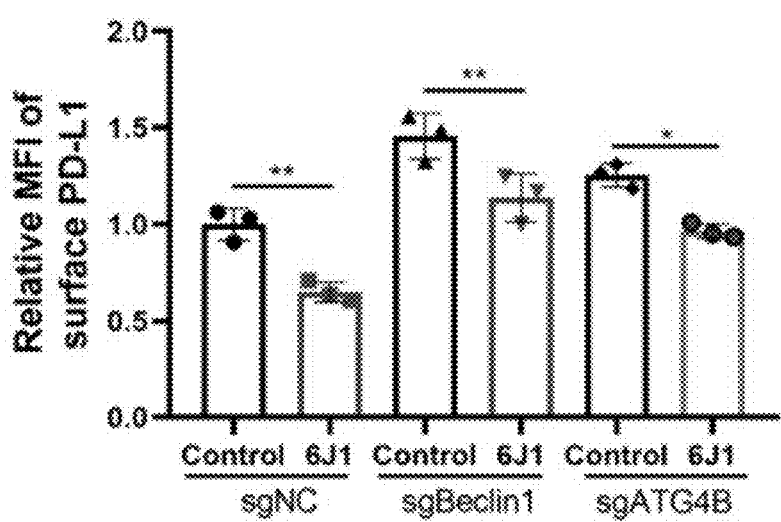
FIG. 7f is a graph showing the relative mean fluorescence intensities based on flow cytometry analysis of PD-L1 at the surface of control, ATG4B-knockout, or Beclin1-knockout, HeLa cells treated with or without 6J1 (1 µM) for 24 h.

FIG. 7d-7e shows that knockout of ATG4B, ATG7, Beclin1, or VPS34 genes fails to abolish 6J1-induced EVs secretion and exosomal PD-L1 secretion. FIG. 7f also confirms that knockout of these autophagy genes does not affect the 6J1-mediated decrease in the level PD-L1 at the cell surface. These results indicate that 6J1-induced exosomal PD-L1 secretion and a reduction in the amount of cell surface PD-L1 is dispensable of canonical autophagy.

Figure 8A:
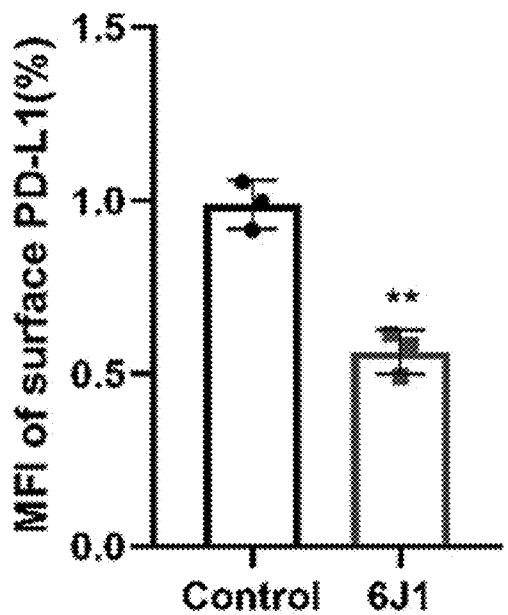
FIG. 8a is a graph showing the flow cytometry-based quantification of plasma membrane levels of PD-L1 in 4T1 cells treated with or without 6J1 (1 µM) for 24 h.
Figure 8B:
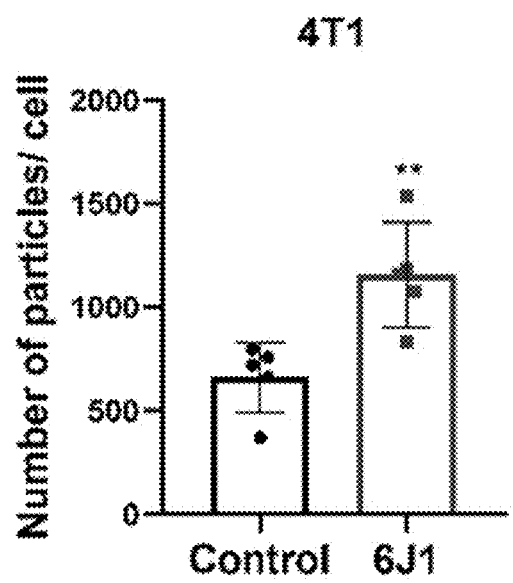
FIG. 8b is a graph showing the concentrations of extracellular vesicle collected from the 4T1 cells treated with or without 6J1 (1 µM) for 24 h using a Nanosight nanoparticle analyzer.
Figure 8C:
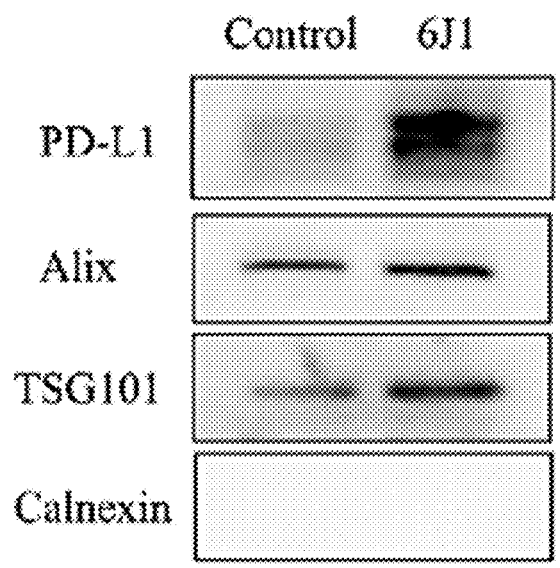
FIG. 8c is a western blot analysis of PD-L1, Alix, TSG101, and Calnexin in the exosomes collected from the 4T1 cells treated with or without 6J1 (1 µM) for 24 h using a Nanosight nanoparticle analyzer.
Figure 8D:
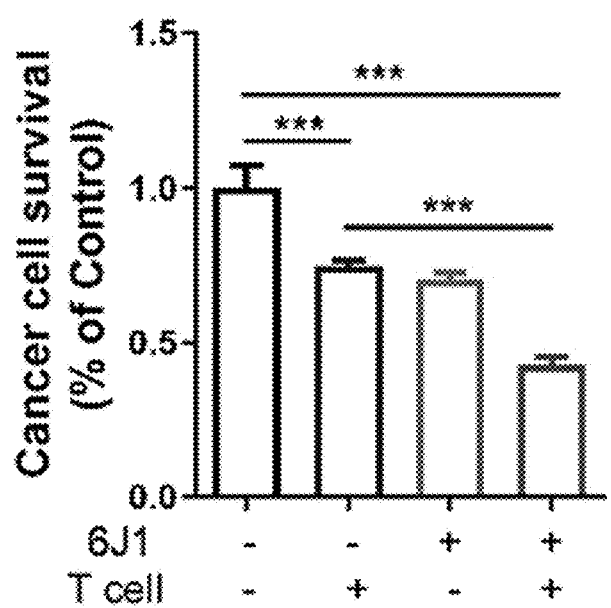
FIG. 8d is a T-cell-meditated tumor cell-killing assay in 4T1 cells treated with or without 6J1 (1 M), and cell viability by the CCK8 assay.
Figure 8E:
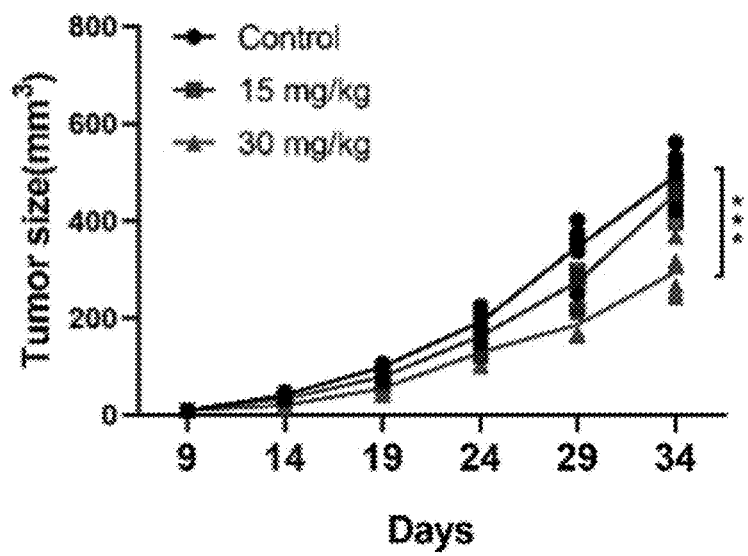
FIG. 8e is a graph showing tumor volumes of three groups of 4T1-implanted female mice treated with buffer, 15 mg/kg 6J1 and 30 mg/kg 6J1.
Figure 8F:
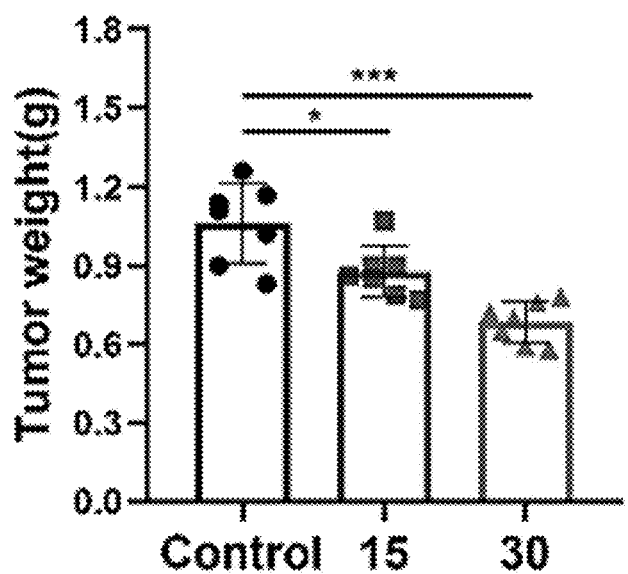
FIG. 8f is a graph showing tumor weights of three groups of 4T1-implanted female mice treated with buffer, 15 mg/kg 6J1 and 30 mg/kg 6J1.
Figure 8G:
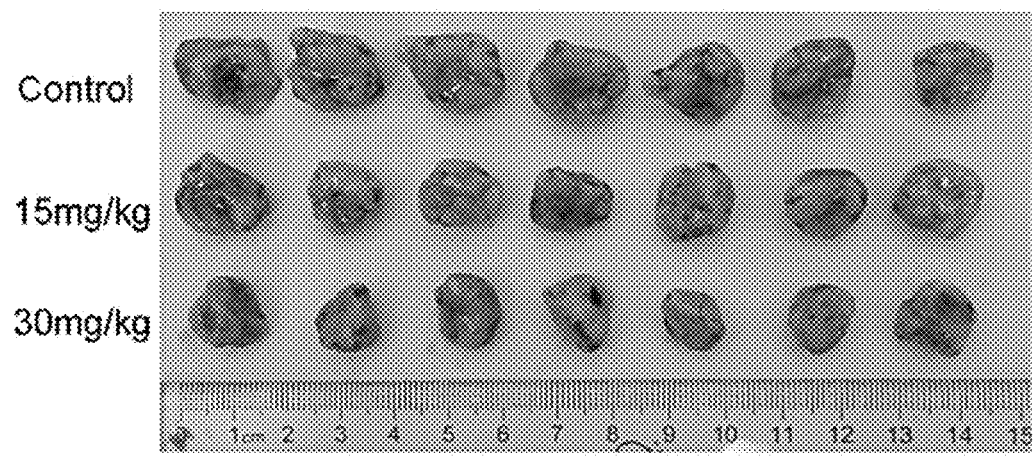
FIG. 8g is the representative images of mouse tumors of three groups of 4T1-implanted female mice treated with buffer, 15 mg/kg 6J1 and 30 mg/kg 6J1.
Figure 8H:
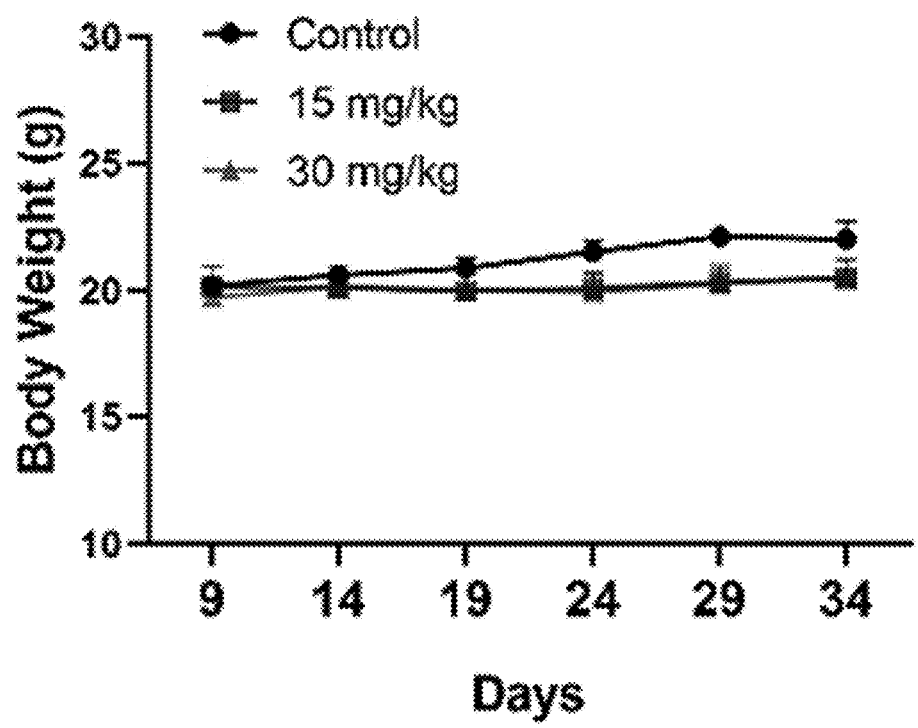
FIG. 8h is a graph showing bodyweights of three groups of 4T1-implanted female mice treated with buffer, 15 mg/kg 6J1 and 30 mg/kg 6J1.

FIGS. 8a-8c confirm that 6J1 decreases the level of cell surface PD-L1 and induces the secretion of PD-L1 in exosomes in 4T1 mouse mammary carcinoma cells FIG. 8d shows 4T1 cells treated with 6J1 are more sensitive to pre-activated T cell-mediated cytolysis when compared to the control cells.

Figure 8I:
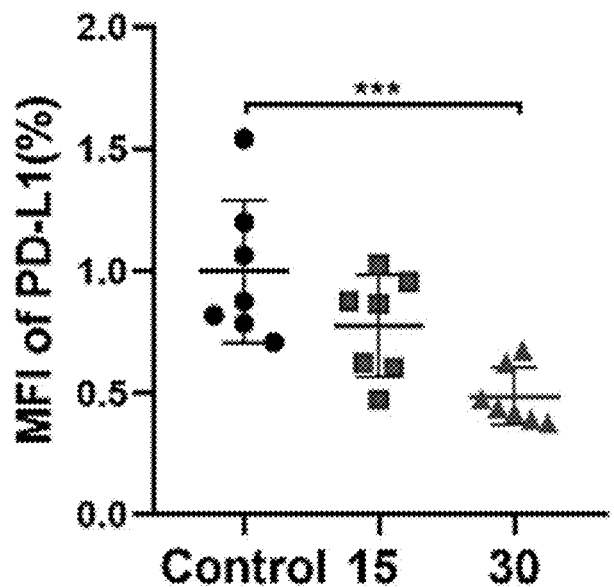
FIG. 8i is a graph showing a flow cytometry-based quantification of plasma membrane levels of PD-L1 in 4T-1 primary tumors.
Figure 8J:
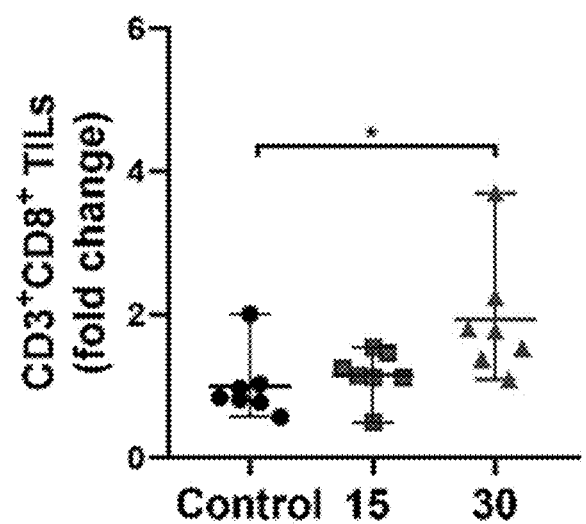
FIG. 8j is a graph showing CD3+CD8+ T-cell populations from the isolated tumor-infiltrating lymphocytes.

FIGS. 8e-8h show that 6J1 significantly decreases the tumor growth at the dose of 30 mg/kg, but does not change the body weight of mice. FIG. 8i shows the cell surface expression of PD-L1 is down-regulated in the primary tumors in mice treated with 6J1 (30 mg/kg). FIG. 8j shows that 6J1 also significantly increases the tumor infiltrating CD8+ T cell populations. However, FIG. 8k indicates that 6J1 has little effect on the expression of IFN-γ in CD8+ T cells. These results show that 6J1 suppresses breast cancer growth in vivo.

Figure 9A:
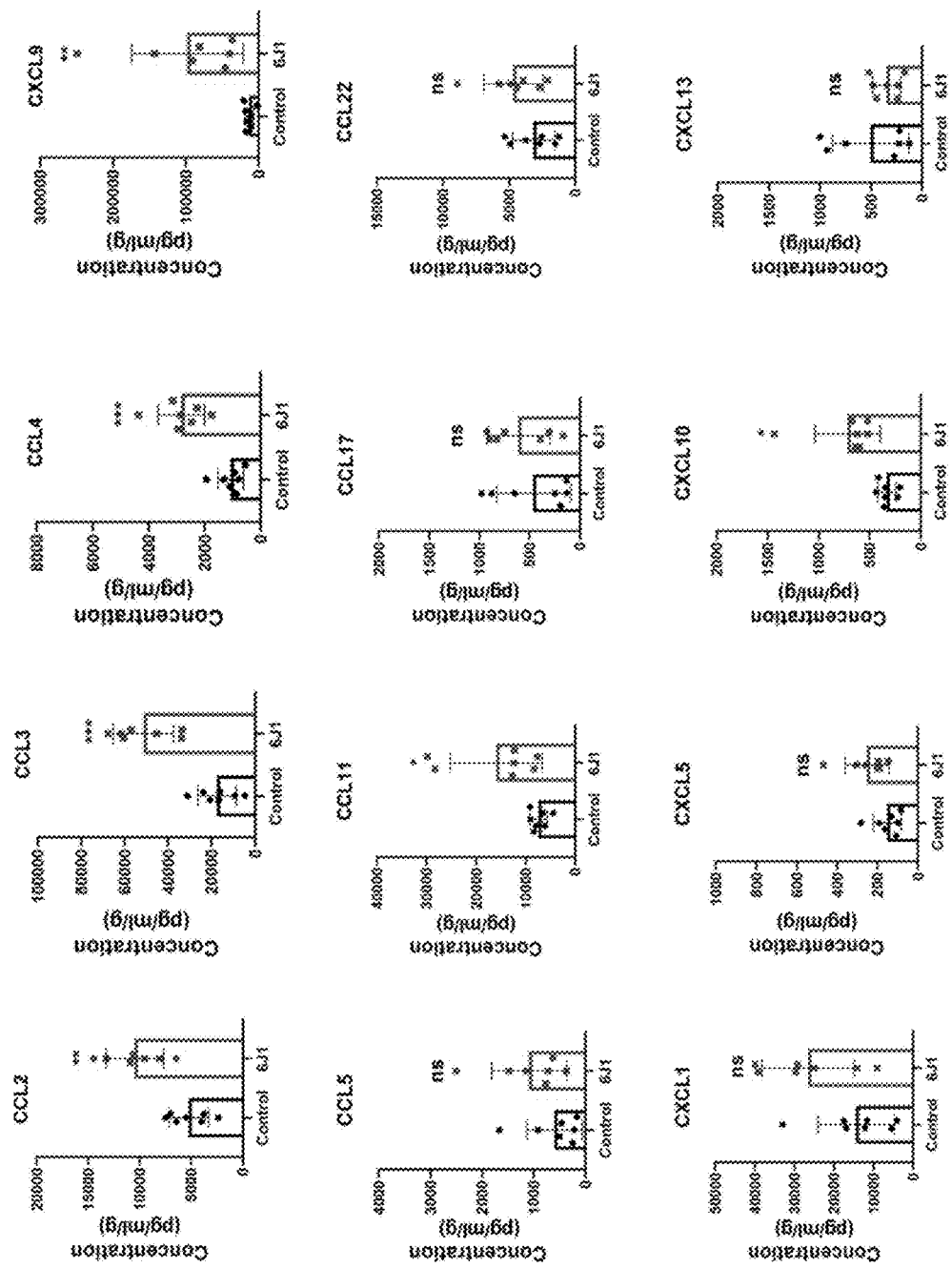
FIG. 9a is graphs showing levels of different chemokine in the microenvironment of 4T1 primary tumors treated with the vehicle or 6J1 by flow cytometry-based quantification.
Figure 9B:
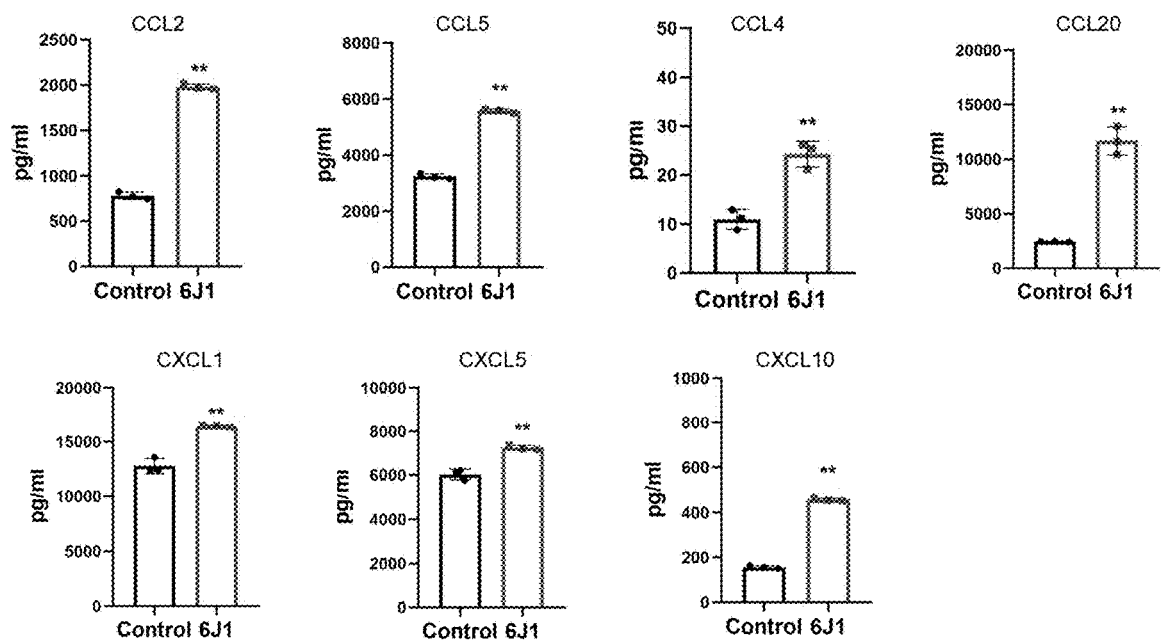
FIG. 9b is graphs showing flow cytometry-based quantifications of the chemokine level in the supernatant of 4T1 treated with or without 6J1 (1 µM).
Figure 9C:
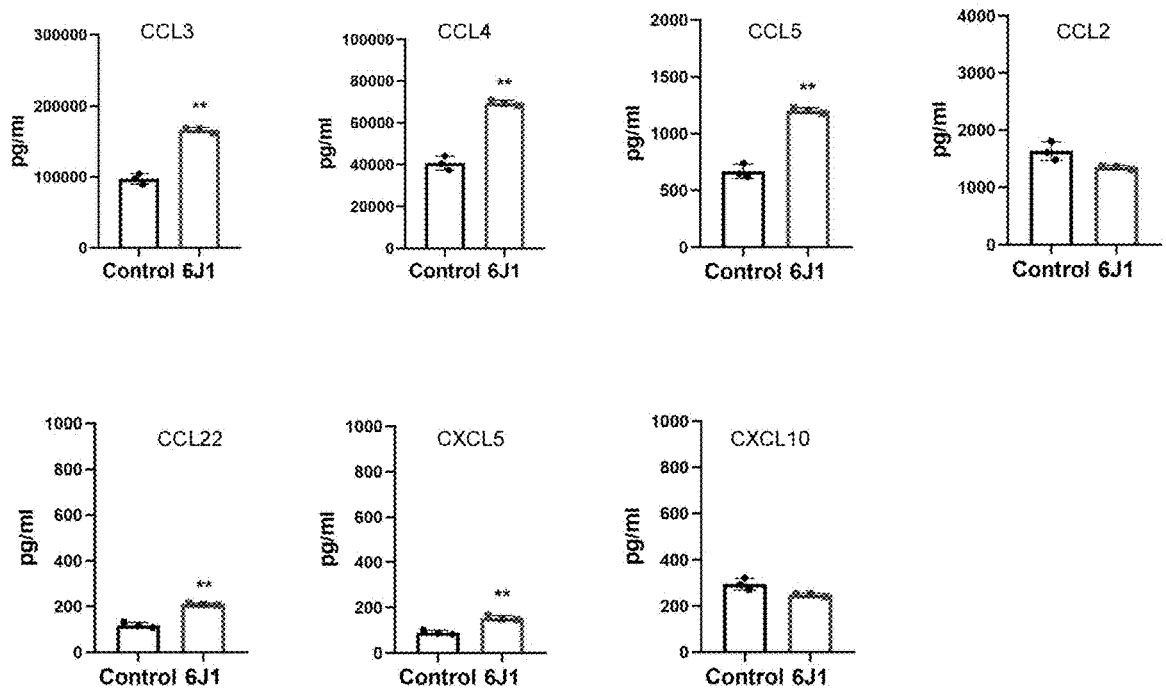
FIG. 9c is graphs showing flow cytometry-based quantifications of the chemokine level in the supernatant of Raw246.7 cells treated with or without 6J1 (1 µM).

FIG. 9a shows that 6J1 significantly increases the secretion of some chemokines (e.g., CCL2, CCL3, CCL4, and CXCL9), but it has little or only subtle effects on others (e.g., CCL5, CCL11, CCL17, CCL22, CXCL1, CXCL5, CXCL10, and CXCL13) in the tumor microenvironment of 4T1 tumors. FIGS. 9b and 9c show that 6J1 also markedly induces the secretion of various chemokines from 4T1 cells and Raw246.7 cells in vitro. These results indicate that 6J1 markedly increases cytokine secretion of chemokines into the tumor microenvironment. The ability of 6J1 to induce the secretion of inflammatory cytokines may turn the immune-cold microenvironment of 4T1 tumors into immune-hot, thereby recruiting more cytotoxic T cells to it, but these T cells appear to be exhausted.

Figure 10A:
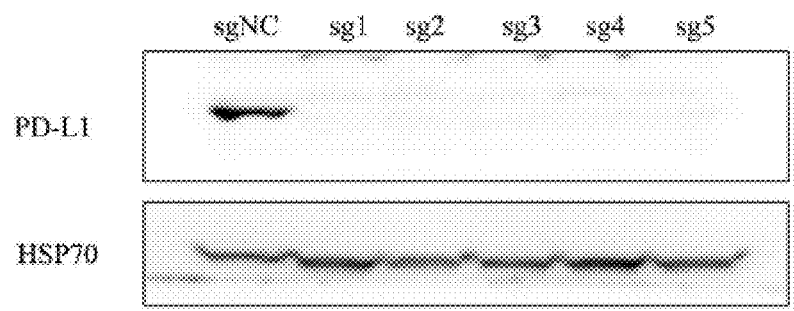
FIG. 10a is a western blot analysis of PD-L1 in control or PD-L1 knockout 4T1 cells.
Figure 10B:
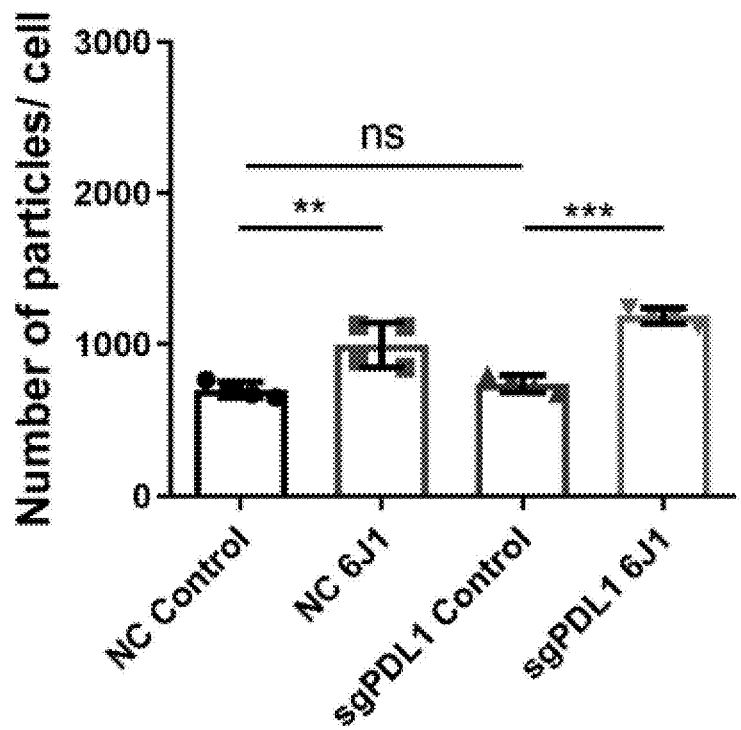
FIG. 10b is a graph showing the concentrations of extracellular vesicle collected from control or PD-L1-knockout 4T1 cells treated with or without 6J1 (1 µM) for 24 h.
Figure 10C:
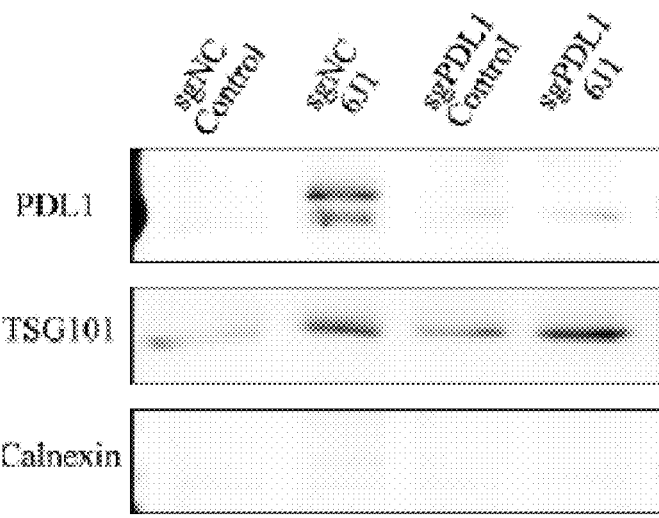
FIG. 10c is a western blot analysis of PD-L1 and TSG101 in exosomes collected from 4T1-NC or 4T1-PD-L1 knockout cells treated with or without 6J1 (1 µM) for 24 h.

FIG. 10a shows the western blot analysis of PD-L1 in 4T1-PD-L1 knockout 4T1 cells. FIG. 10b illustrates that PD-L1 knockout in 4T1 cells does not affect 6J1-induced EVs secretion in 4T1 cells. However, FIG. 10c shows that PD-L1 knockout in 4T1 cells dramatically decreases the expression of PD-L1 in exosomes isolated from cells treated with or without 6J1.

Figure 10D:
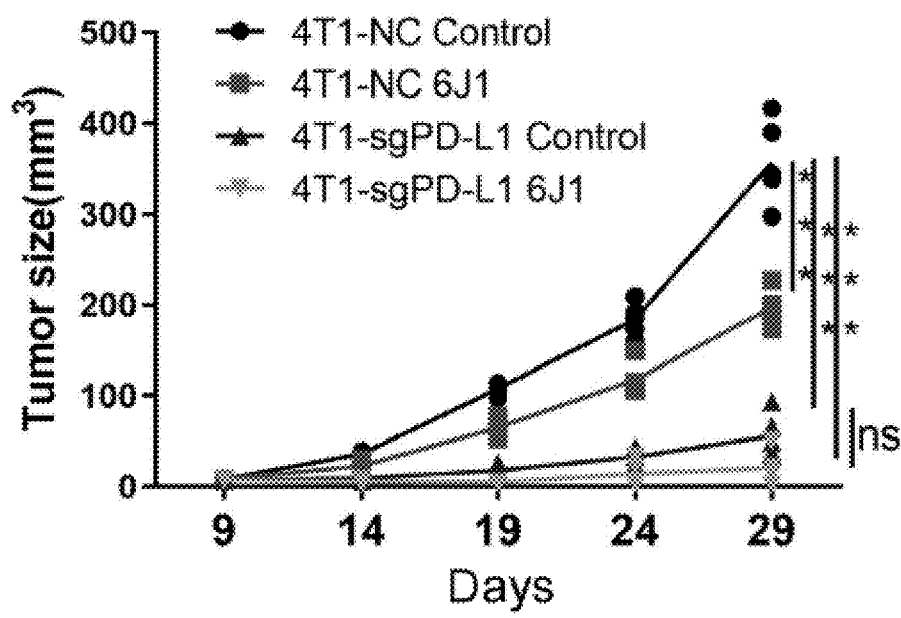
FIG. 10d is a graph showing tumor volumes of 4 groups of 4T1-NC or 4T1-PD-L1 knockout-cell-implanted female Balb/c mice treated with buffer or 6J1 (30 mg/kg, daily).
Figure 10E:
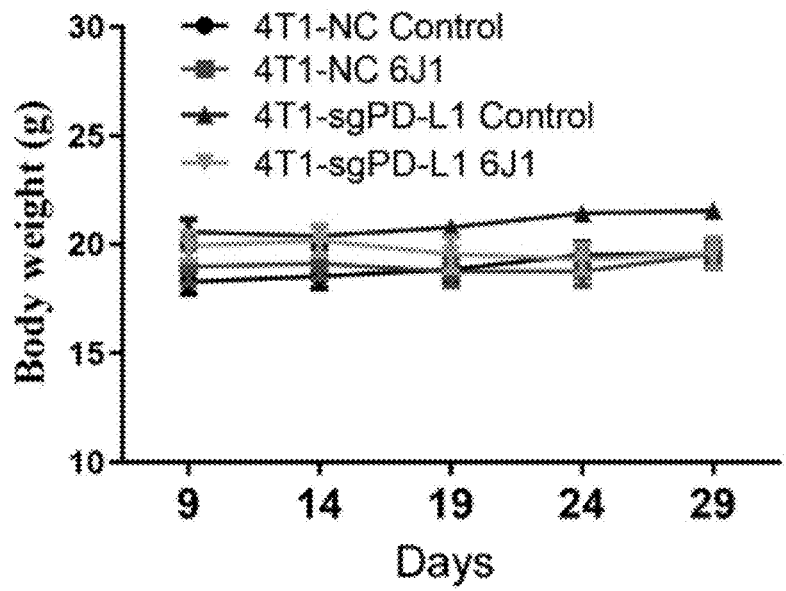
FIG. 10e is a graph showing bodyweights of 4 groups of 4T1-NC or 4T1-PD-L1 knockout-cell-implanted female Balb/c mice treated with buffer or 6J1 (30 mg/kg, daily).
Figure 10F:
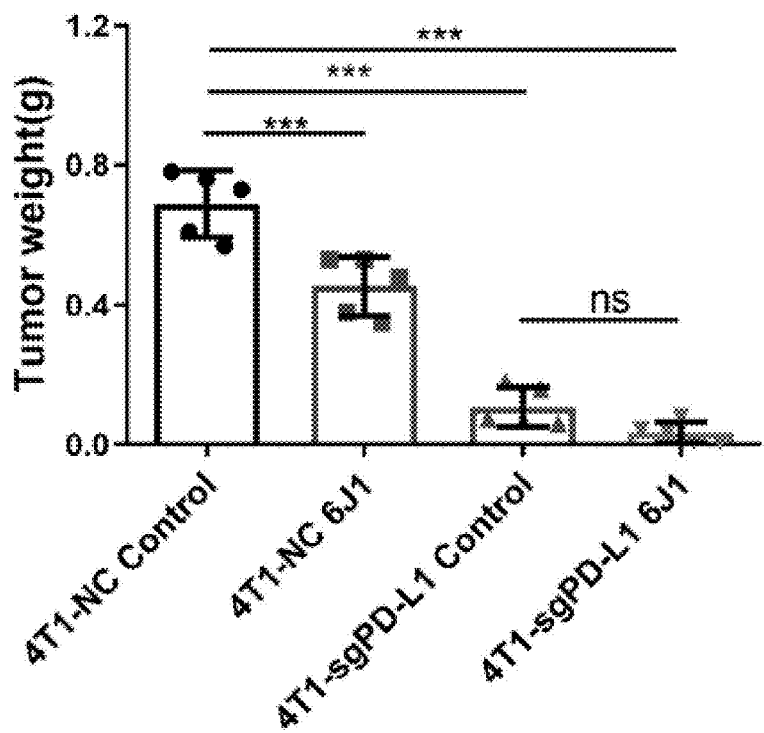
FIG. 10f is a graph showing tumor weights at the endpoint of 4 groups of 4T1-NC or 4T1-PD-L1 knockout-cell-implanted female Balb/c mice treated with buffer or 6J1 (30 mg/kg, daily).
Figure 10G:
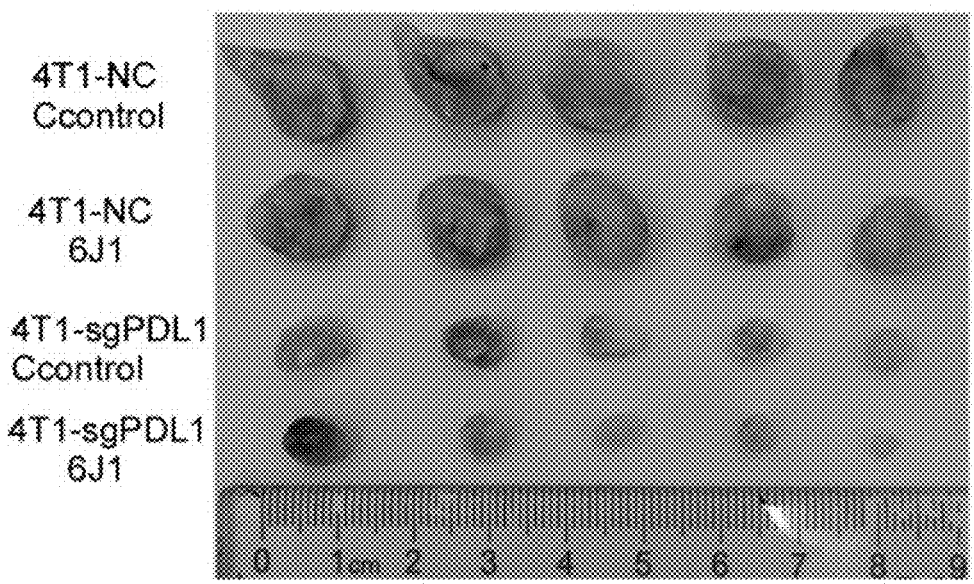
FIG. 10g is a graph showing the representative images of mouse tumors of 4 groups of 4T1-NC or 4T1-PD-L1 knockout-cell-implanted female Balb/c mice treated with buffer or 6J1 (30 mg/kg, daily).

FIG. 10d shows that PD-L1 knockout significantly suppresses tumor growth compared with the control in fat pads of female Balb/c implanted with 4T1-NC or 4T1-PD-L1 knockout cells. FIG. 10e illustrates that the body weights of the tested mice remain stable during the 29 days. FIG. 10f shows the final tumor weight of 4 groups of mice. FIG. 10g illustrates the representative images of mouse tumors of 4 groups. 6J1 treatment fails to decrease further tumor growth of mice implanted with PD-L1-knockout 4T1 cells. These results indicate that the level of PD-L1 expression is an essential factor for tumor growth of 4T1 cells in vivo, and is, at least partially, involved in the anti-cancer effects of 6J1.

Figure 11A:
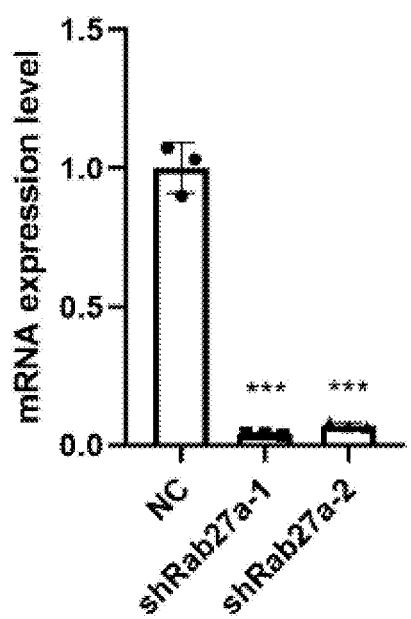
FIG. 11a is a graph showing a qRT-PCR analysis of Rab27A expression in control or 4T1-shRab27A cells.
Figure 11B:
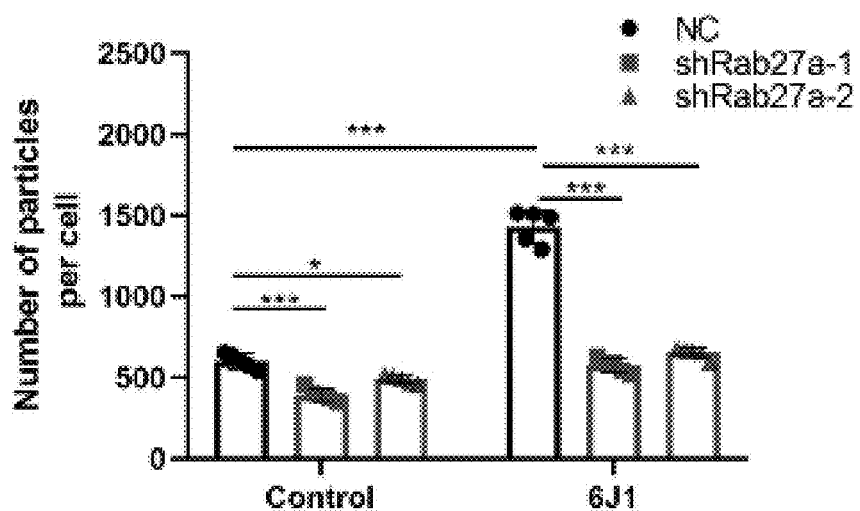
FIG. 11b is a graph showing the concentrations of extracellular vesicle collected from 4T1-shNC or 4T1-shRab27A cells treated with or without 6J1 (1 µM) using a Nanosight nanoparticle analyzer.
Figure 11C:
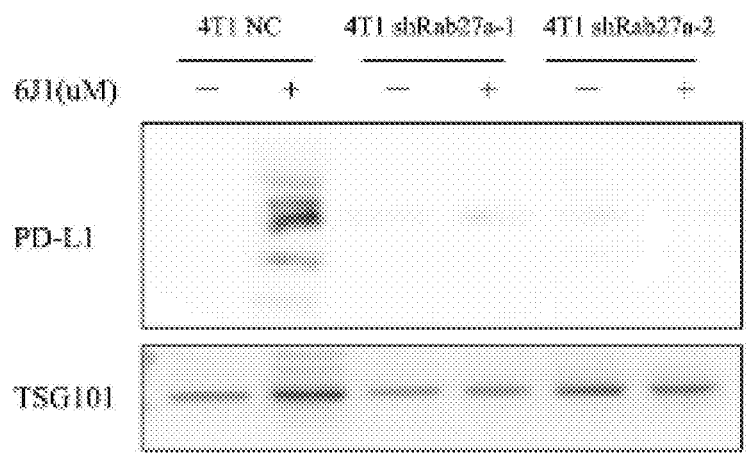
FIG. 11c is a western blot analysis of PD-L1 and TSG101 in exosomes collected from 4T1-shNC or 4T1-shRab27A cells treated with or without 6J1 (1 µM).

FIG. 11a shows qRT-PCR analysis of Rab27A expression in 4T1-shRab27A cells. It indicates the knockout is achieved. FIGS. 11b and 11c respectively show the concentration of extracellular vesicle and western blot analysis of the EVs marker and PD-L1 in exosomes collected from 4T1-shNC or 4T1-shRab27A cells are treated with or without 6J1 (1 µM). They show the knockout of Rab27a significantly inhibits 6J1-induced EVs secretion and exosomal PD-L1 levels.

Figure 11D:
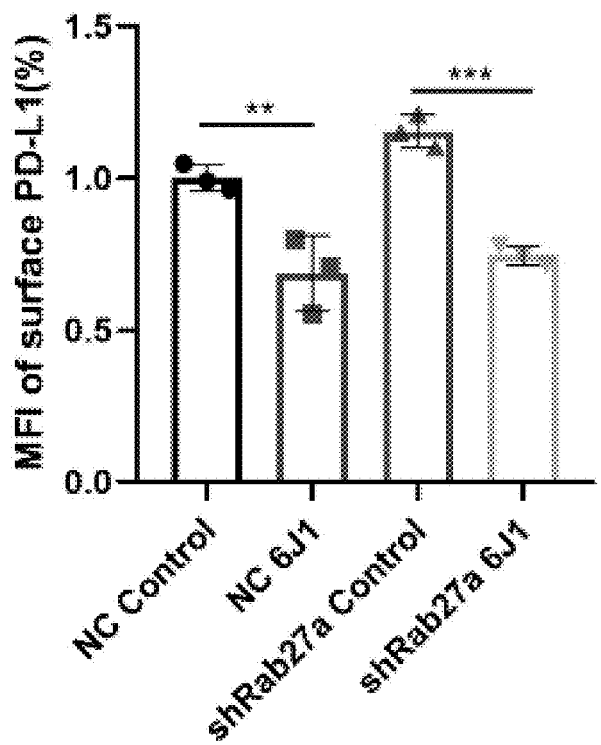
FIG. 11d is a graph showing the mean fluorescence intensities of plasma membrane levels of PD-L1 in 4T1-shNC or 4T1-shRab27A cells treated with or without 6J1 (1 µM).
Figure 11E:
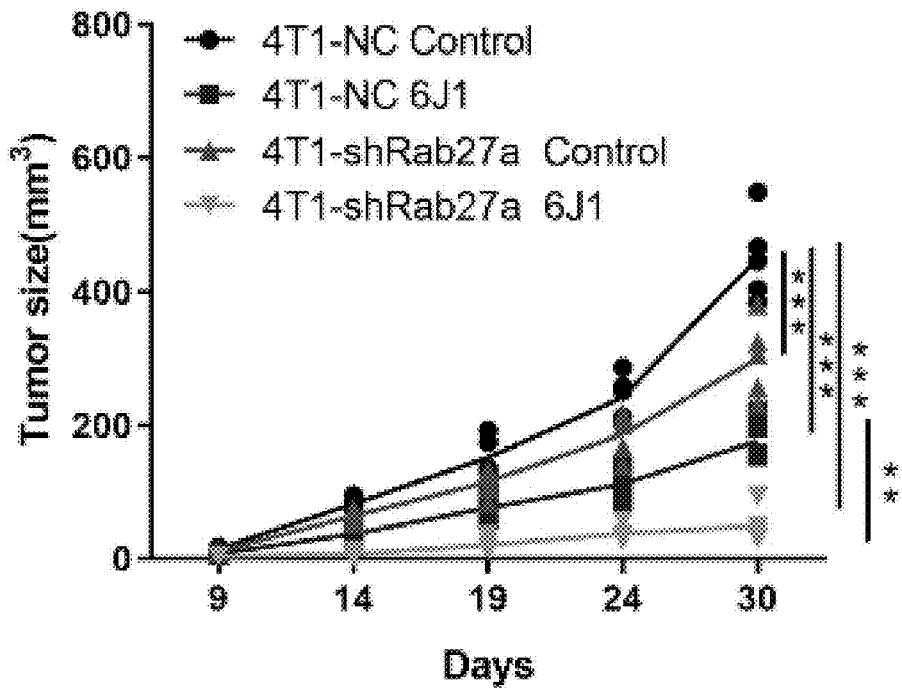
FIG. 11e is a graph showing tumor sizes in 4 groups of 4T1-shNC or 4T1-shRab27A-cell-implanted female Balb/c mice treated with either buffer or 6J1 (30 mg/kg, daily) via oral gavage.
Figure 11F:
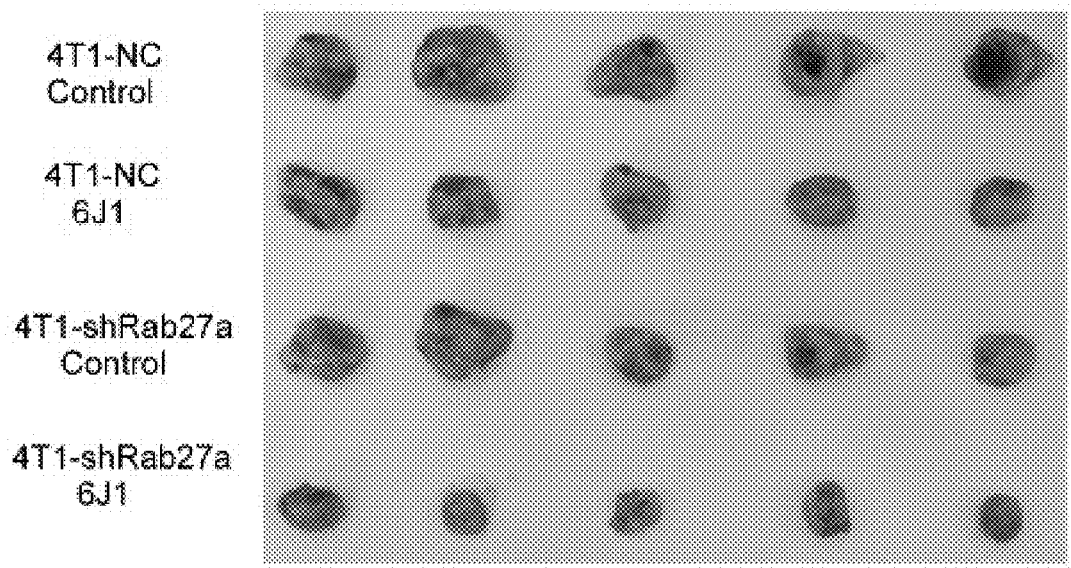
FIG. 11f is the representative images of mouse tumors in 4 groups of 4T1-shNC or 4T1-shRab27A-cell-implanted female Balb/c mice treated with either buffer or 6J1 (30 mg/kg, daily) via oral gavage.
Figure 11G:
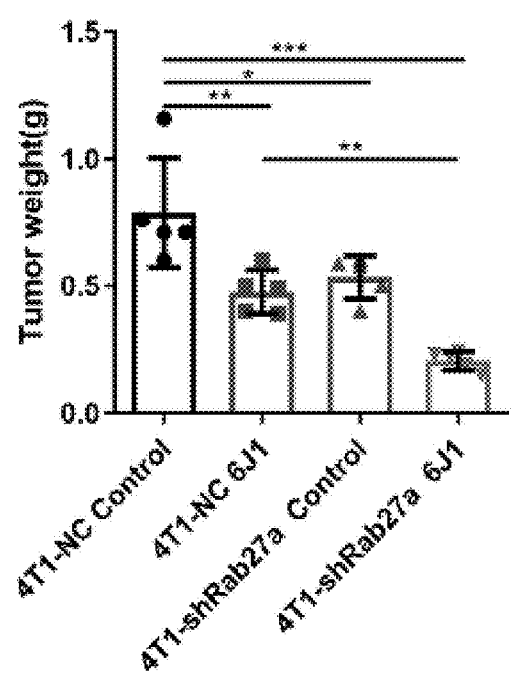
FIG. 11g is a graph showing the tumor weights at the endpoint of 4 groups of 4T1-shNC or 4T1-shRab27A-cell-implanted female Balb/c mice treated with either buffer or 6J1 (30 mg/kg, daily) via oral gavage.
Figure 11H:
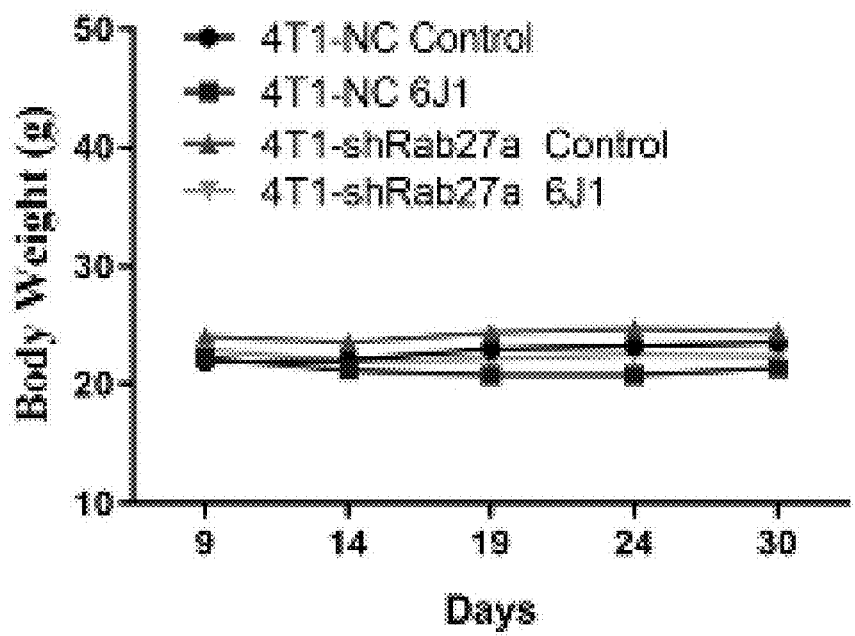
FIG. 11h is a graph showing the body weights of mice of 4 groups of 4T1-shNC or 4T1-shRab27A-cell-implanted female Balb/c mice treated with either buffer or 6J1 (30 mg/kg, daily) via oral gavage.

FIG. 11d shows the flow cytometry-based quantification of plasma membrane levels of PD-L1 in 4T1-shNC or 4T1-shRab27A cells treated with or without 6J1 (1 µM). However, the knockout of Rab27a does not influence the 6J1-induced decrease of cell surface PD-L1 levels.

FIGS. 11e-11h show the tumor size, representative images of mouse tumors, tumor weight at the end time point, and the body weight of 4 groups of 4T1-shNC or 4T1-shRab27A-cell-implanted female Balb/c mice treated with either buffer or 6J1 (30 mg/kg, daily) via oral gavage. The tumor growth and burden in mice implanted with Rab27a-knockout 4T1 cells and treated with 6J1 are significantly smaller than those injected either with control 4T1 cells 5 treated with or without 6J1, or with Rab27a-knockout 4T1 cells without 6J1 treatment.

Figure 11I:
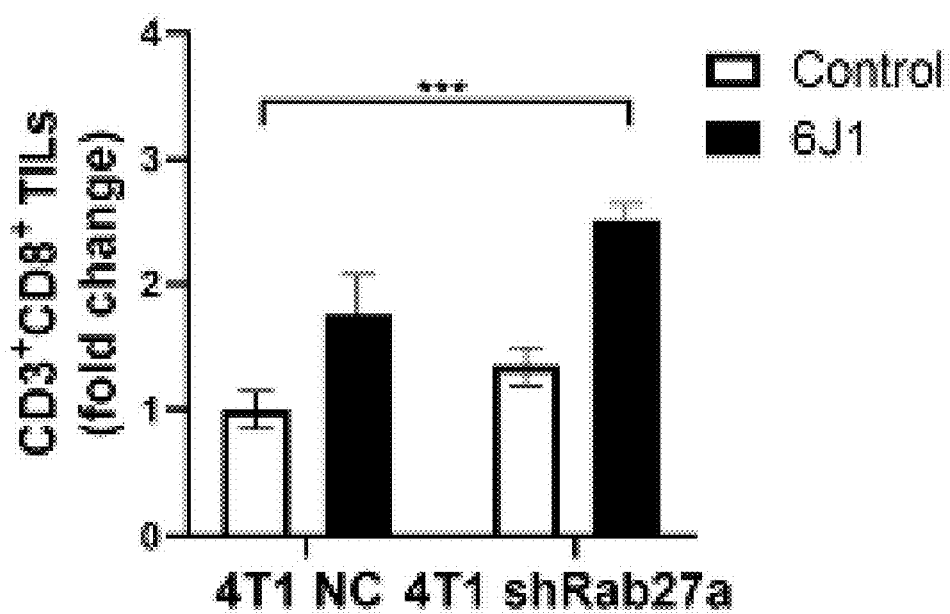
FIG. 11i is a graph showing the populations of CD3+ CD8+ T-cells from the isolated 4T1 tumors.
Figure 11J:
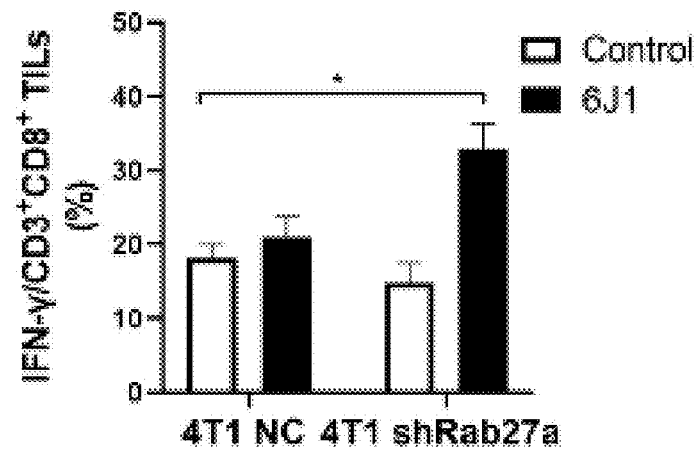
FIG. 11j is a graph showing the intracellular cytokine stains of IFN-γ from the isolated tumor-infiltrating lymphocytes (top), and a graph showing the cytotoxic T cells from isolated 4T1 tumors (bottom).
Figure 11J:
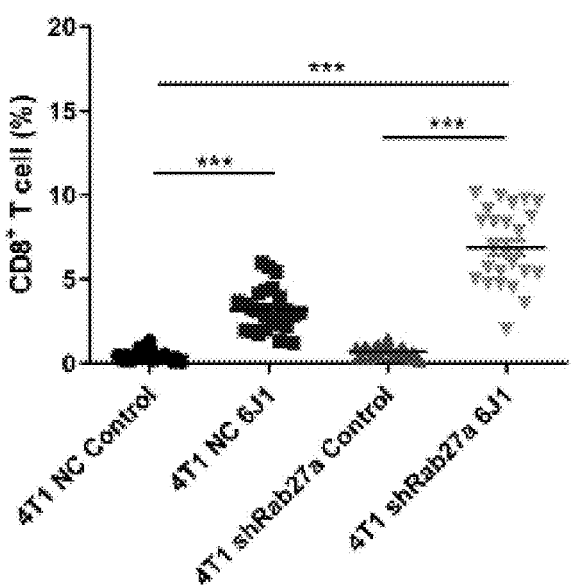

FIGS. 11i-11j show CD3+CD8+ T-cell populations and intracellular cytokine stain of IFN-γ from the isolated tumor-infiltrating lymphocytes. The activated tumor-infiltrating CD8+ T cell population and expression of IFN-γ are significantly increased in the primary tumor isolated from mice implanted with Rab27a-knockout 4T1 cells and treated with 6J1, when compared to those in other groups.

Figure 11K:
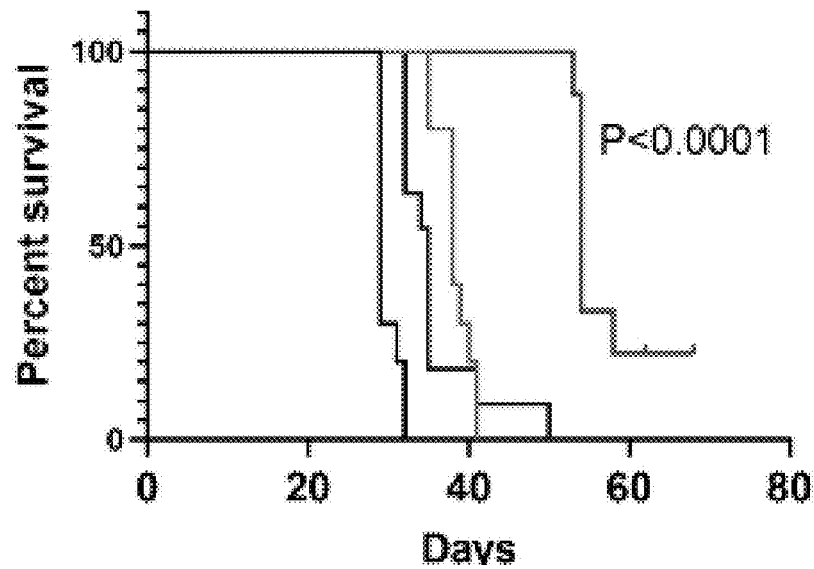
FIG. 11k is a graph showing the survivals of mice bearing 4T1-shNC or 4T1-shRab27A tumors with or without 6J1 intervention.

FIG. 11k shows the survival of mice bearing 4T1-shNC or 4T1-shRab27A tumors with or without 6J1 intervention. The combination of Rab27a knockout and 6J1 treatment substantially prolongs the overall survival of mice bearing orthotopic 4T1 tumors compared with other groups.

Figure 11L:
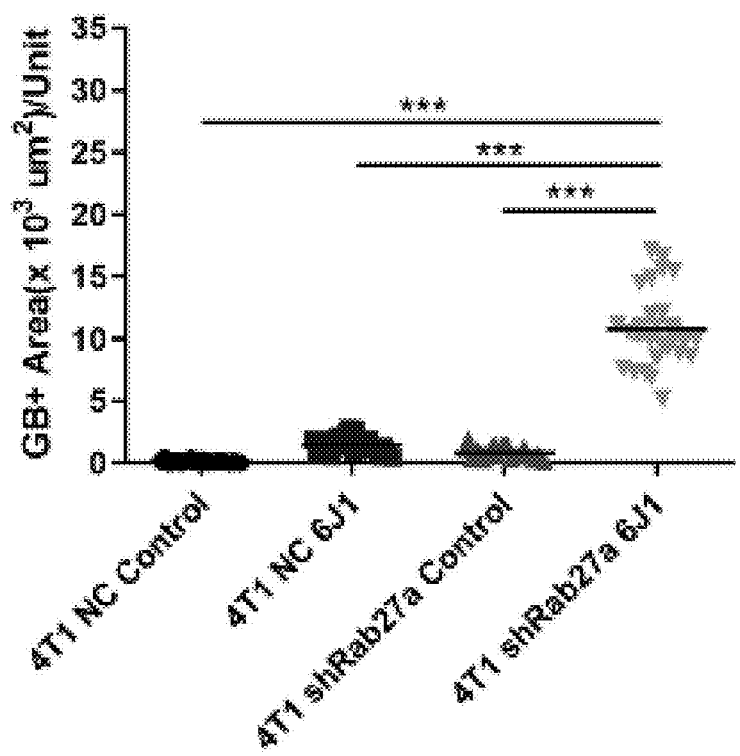
FIG. 11l is a graph showing the immunofluorescent staining of CD8 and granzyme B protein expression patterns in the 4T1 tumors.

FIG. 11*l* shows the immunofluorescent staining of CD8 and granzyme B protein expression patterns in the 4T-1 tumors. More infiltrated CD8+ T cells are detected in tumors isolated from mice implanted with RAB27a-knockout 4T1 cells and treated with 6J1 compared to samples from other groups.

Figure 11M:
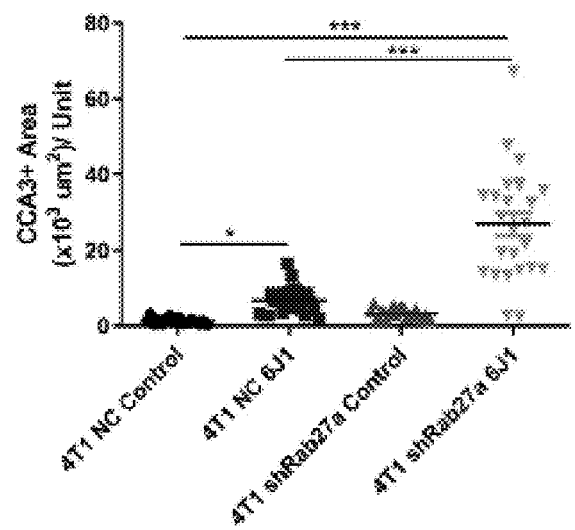
FIG. 11m is a graph showing the immunofluorescent staining of cleaved Caspase3 protein expression patterns in the 4T1 tumors.

FIG. 11*m* shows the immunofluorescent staining of cleaved Caspase3 protein expression patterns in the 4T-1 tumors. The stronger clustered apoptotic signals are observed in the tumors from mice implanted with Rab27a-knockout 4T1 cells and treated with 6J1 compared to other groups.

FIGS. 11*a*-11*m* indicate that inhibiting exosome secretion by Rab27 knockdown significantly enhances the antitumor activity of 6J1 in the Balb/c orthotopic mouse model. Inhibiting exosomal PD-L1 secretion increases the antitumor immunity of 6J1.

Figure 12A:
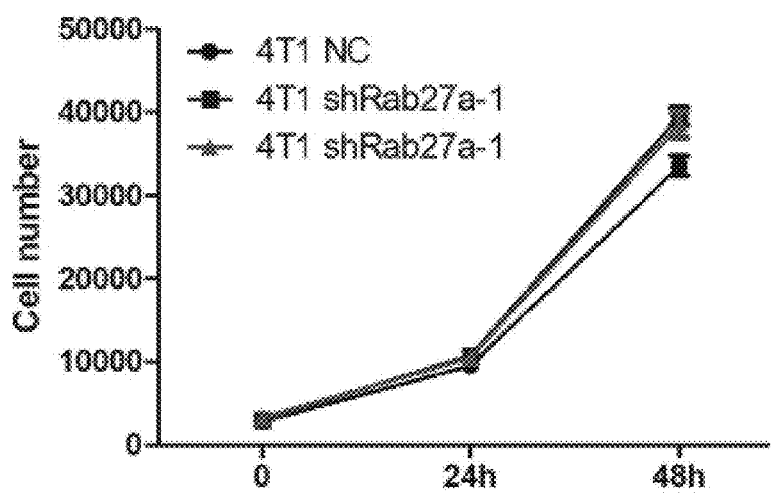
FIG. 12a is a graph showing the cell proliferation of 4T1-shNC or 4T1-shRab27A cells.
Figure 12B:
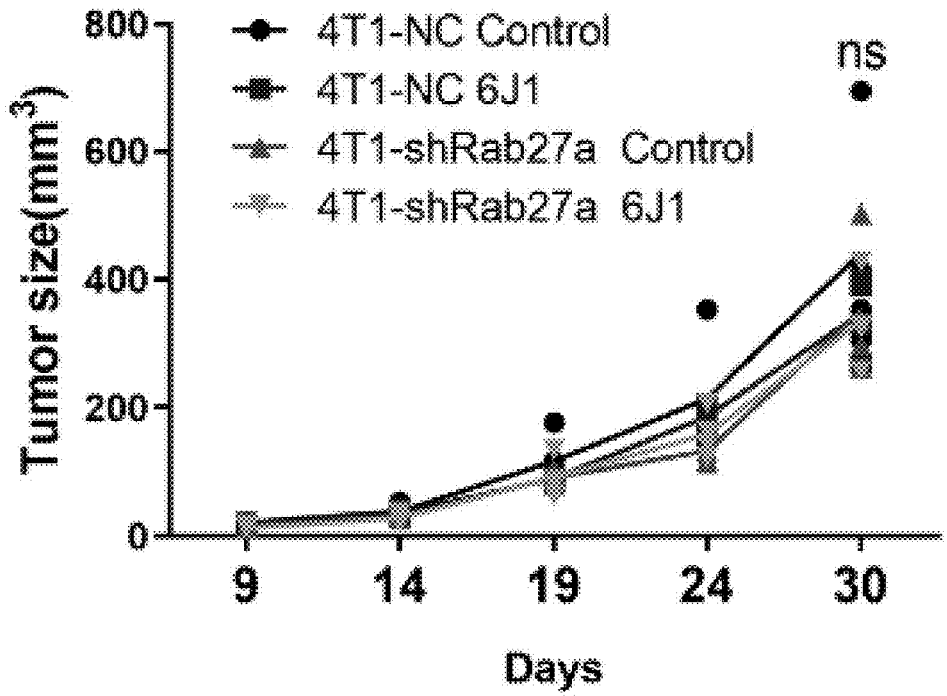
FIG. 12b is a graph showing the tumor volumes of 4 groups of 4T1-shNC or 4T1-shRab27A-cell-implanted female Balb/c nude mice treated with either buffer or 6J1 (30 mg/kg, daily) via oral gavage.
Figure 12C:
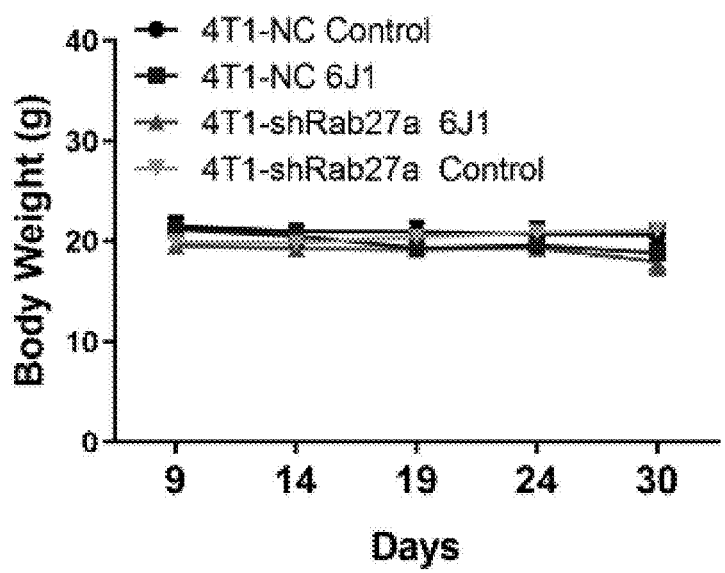
FIG. 12c is a graph showing the bodyweights of 4 groups of 4T1-shNC or 4T1-shRab27A-cell-implanted female Balb/c nude mice treated with either buffer or 6J1 (30 mg/kg, daily) via oral gavage.
Figure 12D:
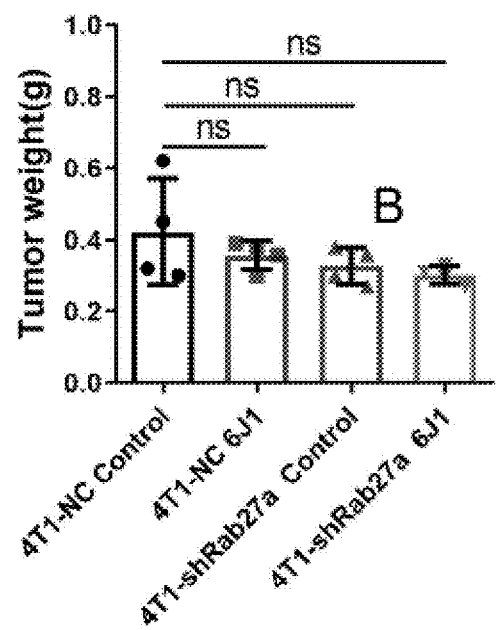
FIG. 12d is a graph showing the tumor weights at the end time point of 4 groups of 4T1-shNC or 4T1-shRab27A-cell-implanted female Balb/c nude mice treated with either buffer or 6J1 (30 mg/kg, daily) via oral gavage.
Figure 12E:
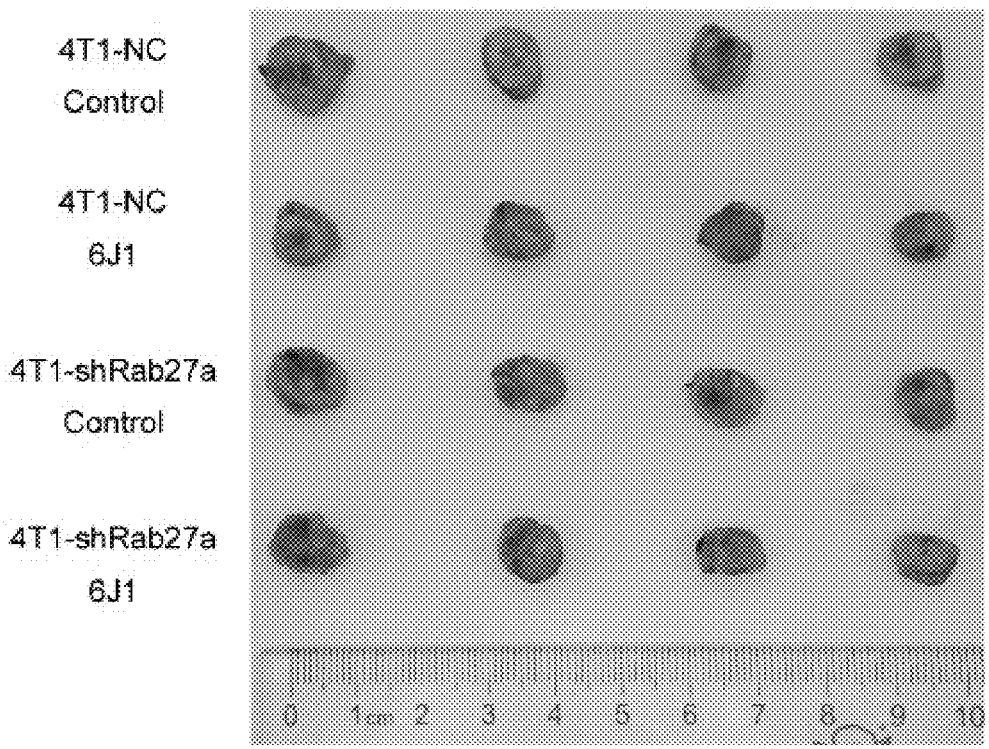
FIG. 12e is the representative images of mouse tumors of 4 groups of 4T1-shNC or 4T1-shRab27A-cell-implanted female Balb/c nude mice treated with either buffer or 6J1 (30 mg/kg, daily) via oral gavage.

FIG. 12*a* shows the cell proliferation of 4T1-shNC or 4T1-shRab27A cells. FIGS. 12*b*-12*e* show respectively the tumor volumes, body weights of mice, final tumor weights, and representative images of mouse tumors of 4 groups of 4T1-shNC or 4T1-shRab27A-cell-implanted female Balb/c nude mice treated with either buffer or 6J1c (30 mg/kg, daily) via oral gavage.

FIGS. 12*a*-12*e* show that Rab27a knockout has little effect on the tumor size and the bodyweight in these immunocompromised mice. The anti-cancer effect of 6J1 or the combination of 6J1 and Rab27a knockout is also dramatically abolished in the immunocompromised mouse model. Thus, anti-cancer effect of 6J1 requires an intact immune system.

Figure 13A:
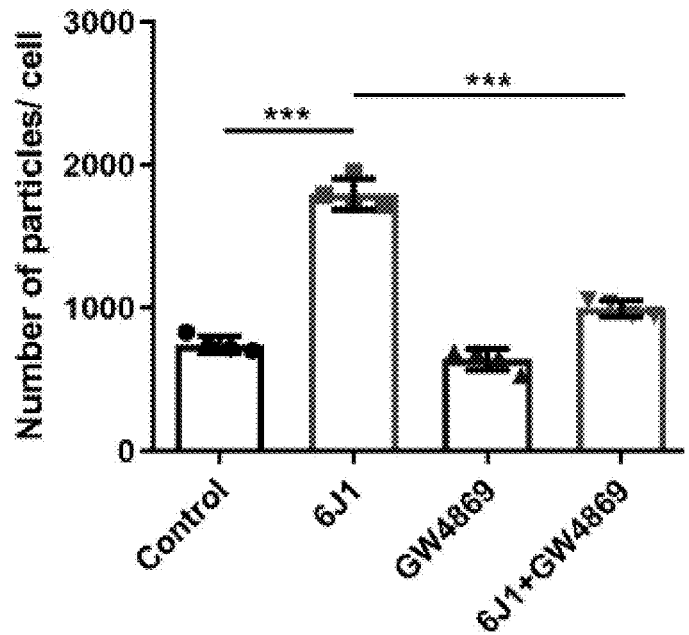
FIG. 13a is a graph showing the concentrations of extracellular vesicle collected from 4T1 cells treated with 6J1 (1 μM), GW4869 (10 μM), or 6J1 and GW4869, respectively. GW4869 inhibits exosome secretion of 4T1 cells induced by 6J1.

FIG. 13*a* shows the concentration of extracellular vesicle collected from 4T1 cells treated with 6J1 (1 μM), GW4869 (10 μM), or 6J1 and GW4869, respectively. GW4869 inhibits exosome secretion of 4T1 cells induced by 6J1.

Figure 13B:
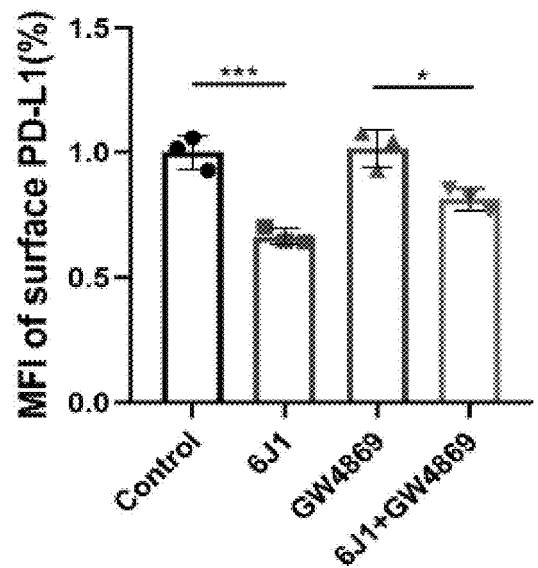
FIG. 13b is a graph showing a flow cytometry-based quantification of plasma membrane levels of PD-L1 in 4T1 cells treated 6J1 (1 μM), GW4869 (10 μM), or 6J1 and GW4869, respectively.
Figure 13C:
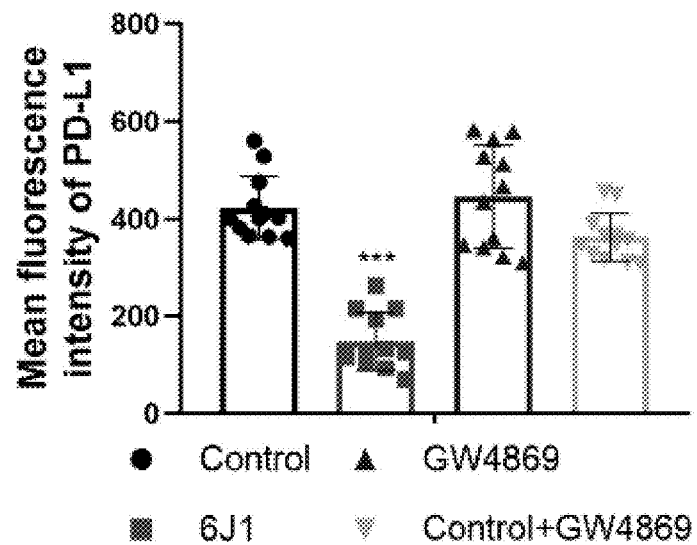
FIG. 13c is a graph showing the mean fluorescence intensities of PD-L1 in PD-L1 GFP-expressing 4T1 cells treated 6J1 (1 μM), GW4869 (10 μM), or 6J1 and GW4869, respectively.

FIG. 13*b* shows the flow cytometry-based quantification of plasma membrane levels of PD-L1 in 4T1 cells treated 6J1 (1 μM), GW4869 (10 μM), or 6J1 and GW4869, respectively. FIG. 13*c* illustrates the mean fluorescence intensity of PD-L1 in these cells. These results indicate that GW4869 does not impair 6J1-mediated reduction of cell surface PD-L1.

Figure 13D:
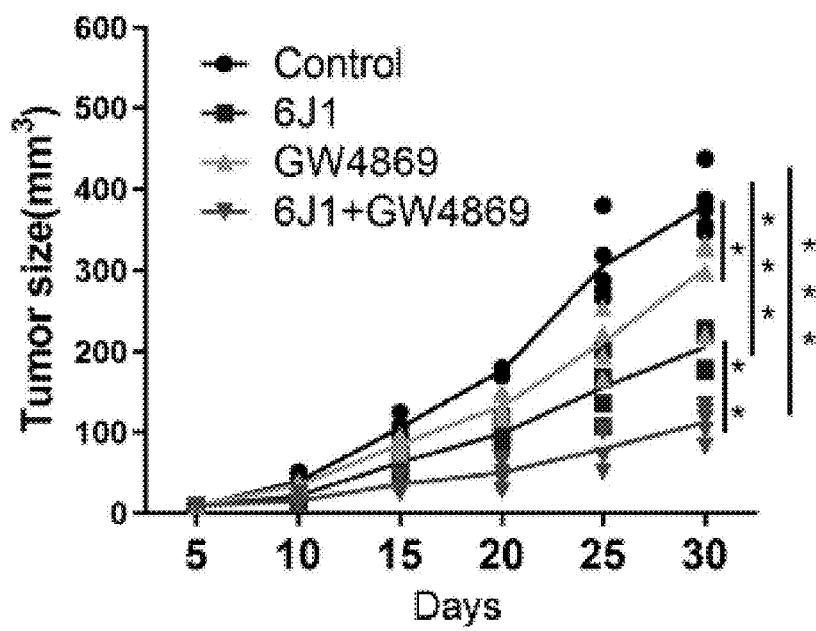
FIG. 13d is a graph showing the tumor volumes of 4T1-cell-implanted female Balb/c mice treated with buffer, 6J1 (30 mg/kg, oral, daily), GW4869 (2.5 mg/kg, IP, daily), or 6J1 and GW4869, respectively.
Figure 13E:
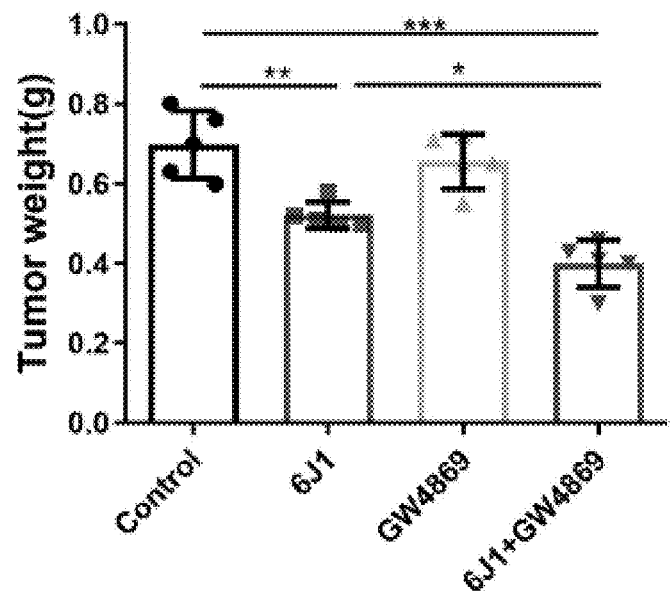
FIG. 13e is a graph showing the tumor weights of 4T1-cell-implanted female Balb/c mice treated with buffer, 6J1 (30 mg/kg, oral, daily), GW4869 (2.5 mg/kg, IP, daily), or 6J1 and GW4869, respectively.
Figure 13F:
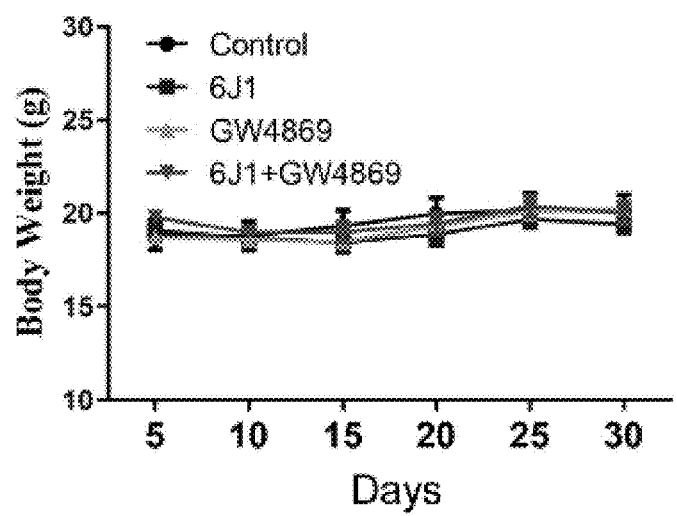
FIG. 13f is a graph showing the body weights of 4T1-cell-implanted female Balb/c mice treated with buffer, 6J1 (30 mg/kg, oral, daily), GW4869 (2.5 mg/kg, IP, daily), or 6J1 and GW4869, respectively.
Figure 13G:
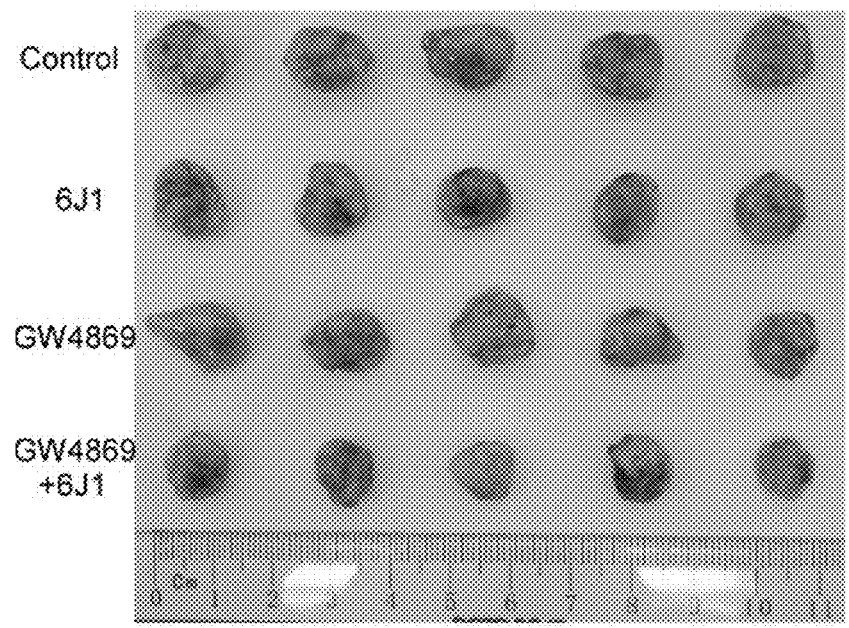
FIG. 13g is the representative images of mouse tumors of 4T1-cell-implanted female Balb/c mice treated with buffer, 6J1 (30 mg/kg, oral, daily), GW4869 (2.5 mg/kg, IP, daily), or 6J1 and GW4869, respectively.

FIGS. 13*de* and 13*f* show the tumor volume and body weight of 4T1-cell-implanted female Balb/c mice treated with buffer, 6J1 (30 mg/kg, oral, daily), GW4869 (2.5 mg/kg, IP, daily), or 6J1 and GW4869, respectively. FIG. 13*e* shows the tumor weight of these mice. FIG. 13*g* illustrates the representative images of mouse tumors. These results show that the combination of GW4869 and 6J1 suppresses tumor growth and decreases tumor burden more effectively than GW4869 or 6J1 alone. These data indicated that inhibiting exosome secretion by either pharmacological inhibitors or a genetic approach in tumor cells significantly augments the anti-cancer efficacy of 6J1 in vivo.

Figure 14A:
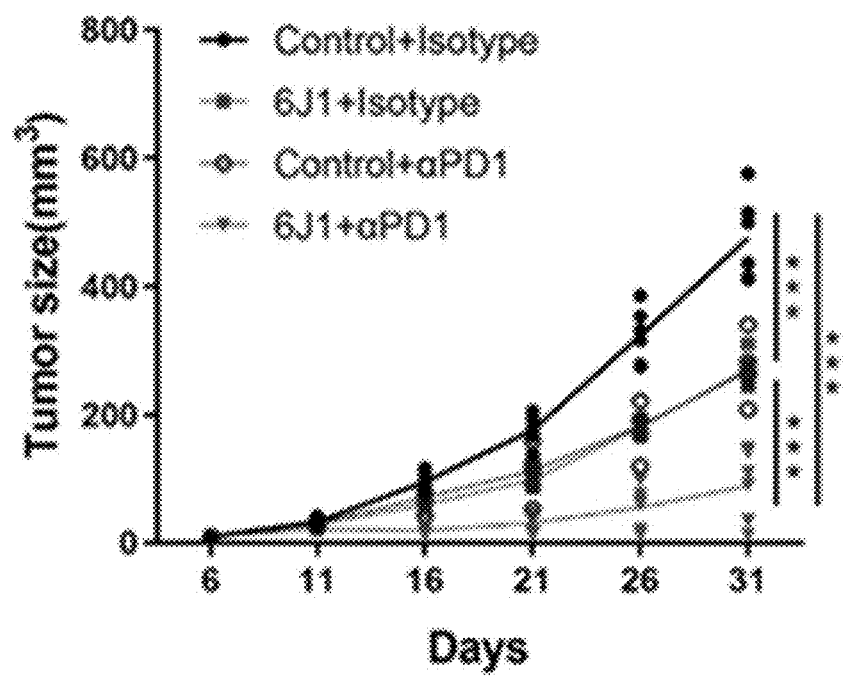
FIG. 14a is a graph showing the tumor sizes of 4T1-cell-implanted female Balb/c mice treated with buffer, 6J1 (30 mg/kg, oral, daily) and/or PD1 antibody (200 μg/per mouse, every 3 days, IP) for 4 weeks.
Figure 14B:
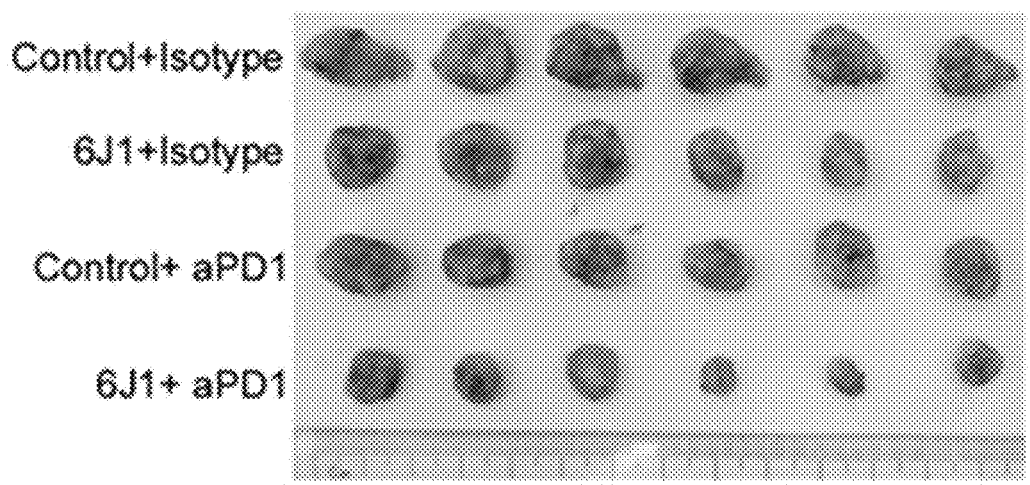
FIG. 14b is the representative images of mouse tumors of 4T1-cell-implanted female Balb/c mice treated with buffer, 6J1 (30 mg/kg, oral, daily) and/or PD1 antibody (200 μg/per mouse, every 3 days, IP) for 4 weeks.
Figure 14C:
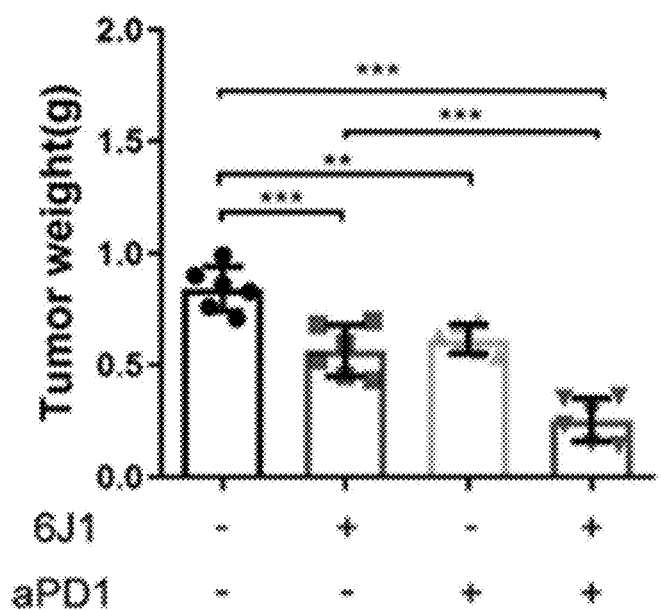
FIG. 14c is a graph showing the tumor weights at the end point of 4T1-cell-implanted female Balb/c mice treated with buffer, 6J1 (30 mg/kg, oral, daily) and/or PD1 antibody (200 g/per mouse, every 3 days, IP).
Figure 14D:
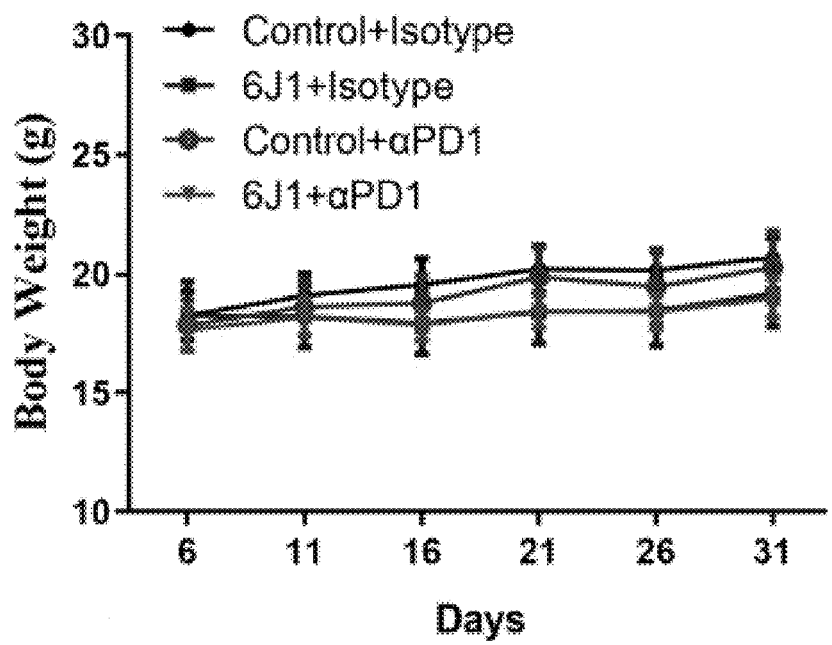
FIG. 14d is a graph showing the bodyweights of 4T1-cell-implanted female Balb/c mice treated with buffer, 6J1 (30 mg/kg, oral, daily) and/or PD1 antibody (200 μg/per mouse, every 3 days, IP) for 4 weeks.

FIGS. 14*a*, 14*b* and 14*d* show the change of tumor sizes and body weights of 4T1 cell-implanted mice treated with buffer, 6J1 and/or anti-PD-1 antibody. FIG. 14*d* illustrates the tumor weights at the end point. These results show that the tumor growth and tumor burden in 4T1 cell-implanted mice treated with both 6J1 and anti-PD-1 antibodies are significantly weaker compared with 4T1 cell-implanted mice treated with 6J1 or anti-PD-1 antibody alone.

Figure 14E:
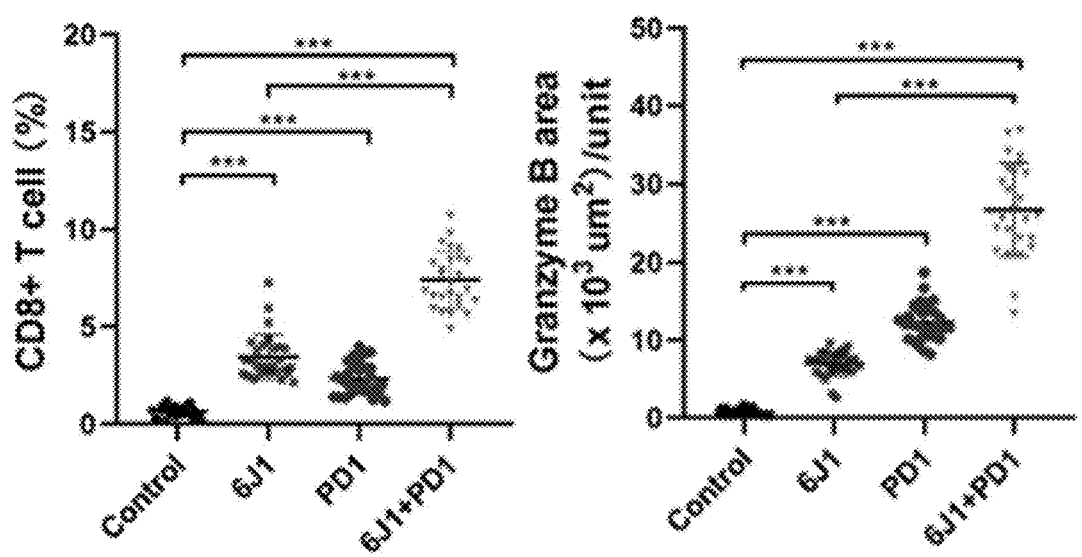
FIG. 14e is graphs showing the expression of CD8 and granzyme B in the 4T1 primary tumors determined by immune-staining.
Figure 14F:
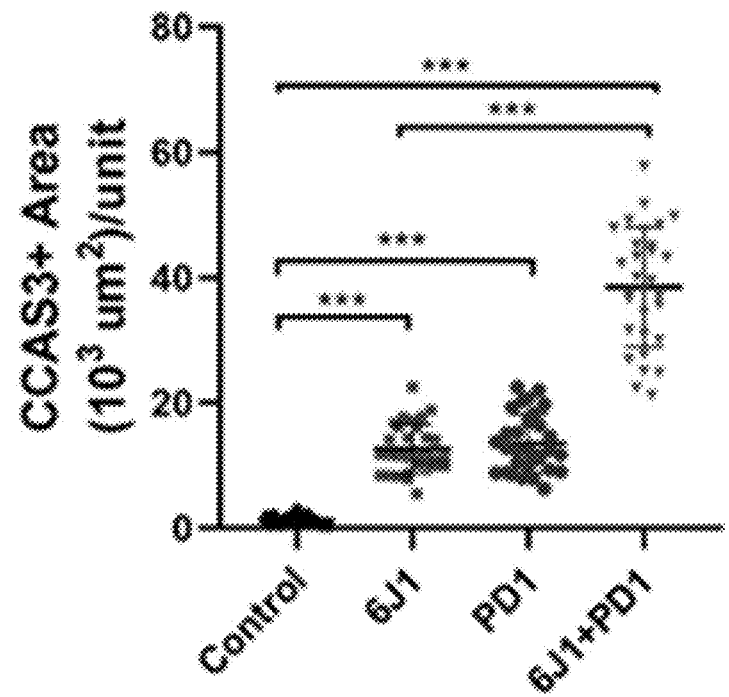
FIG. 14f is a graph showing the expression of cleaved Caspase3 in the primary 4T1 tumors determined by immune-staining.

FIGS. 14*e* and 14*f* illustrate the expressions of CD8 and granzyme B, and cleaved Caspase3 in the primary 4T1 tumors. An increasing number of infiltrated CD8+ T cells and stronger granzyme B signals are detected in tumor sections isolated from mice treated with both 6J1 and anti-PD-1 antibodies, compared to other groups. Larger areas of CCA3 signal are also detected in the group of both 6J1 and anti-PD-1 antibodies. These results demonstrate that 6J1 promotes the anti-cancer immunity of anti-PD-1 antibodies and vice versa.

Figure 15A:
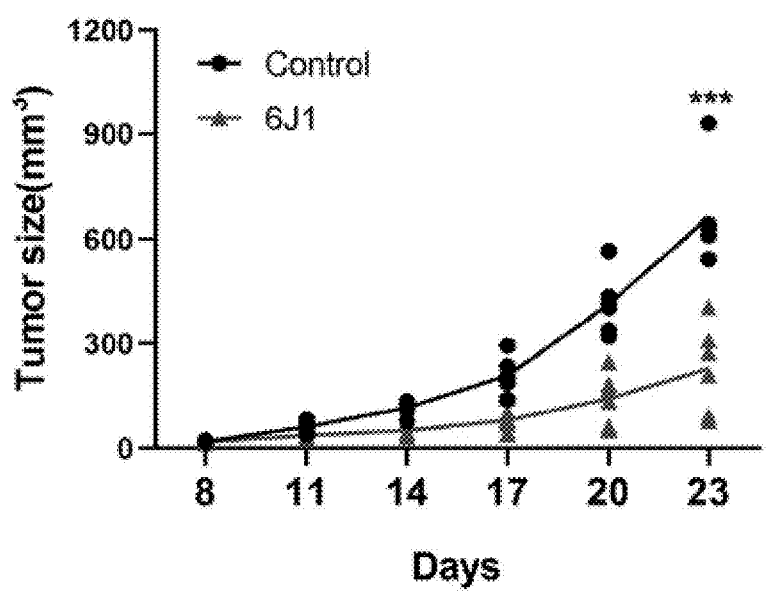
FIG. 15a is a graph showing the tumor size of B16-F10-cell-implanted C57BL/6J mice treated with buffer or 6J1 (30 mg/kg, daily, oral gavage).
Figure 15B:
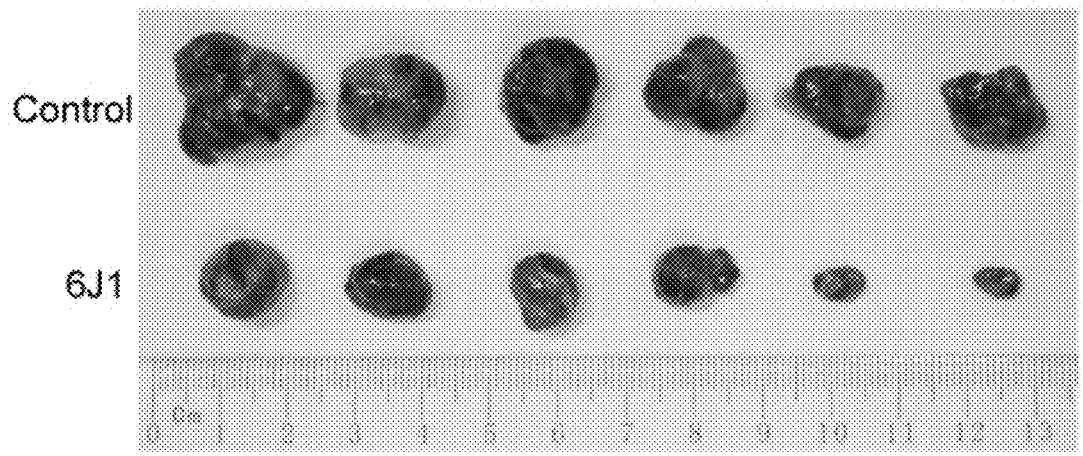
FIG. 15b is representative images of tumors at the last time point of B16-F10-cell-implanted C57BL/6J mice treated with buffer or 6J1 (30 mg/kg, daily, oral gavage).
Figure 15C:
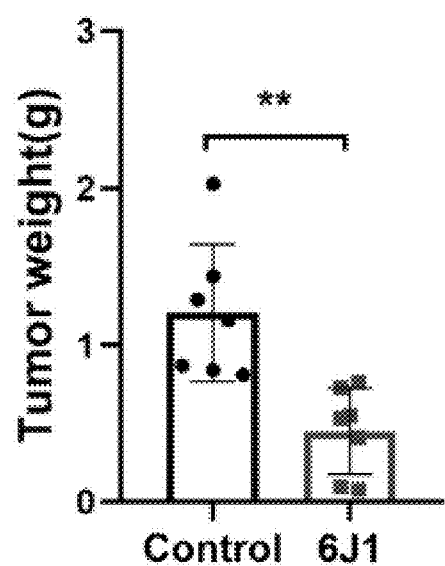
FIG. 15c is a graph showing weights of tumors at the last time point of B16-F10-cell-implanted C57BL/6J mice treated with buffer or 6J1 (30 mg/kg, daily, oral gavage).
Figure 15D:
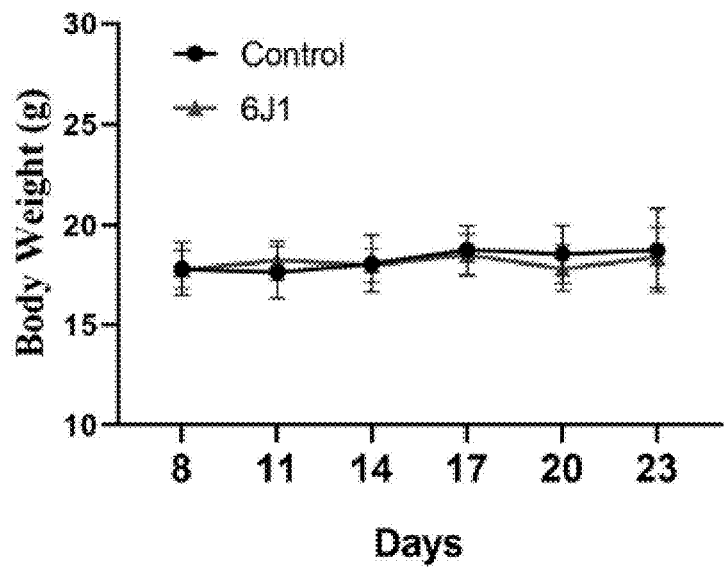
FIG. 15d is a graph showing body weights of mice of B16-F10-cell-implanted female C57BL/6J mice treated with buffer or 6J1 (30 mg/kg, daily, oral gavage).
Figure 15E:
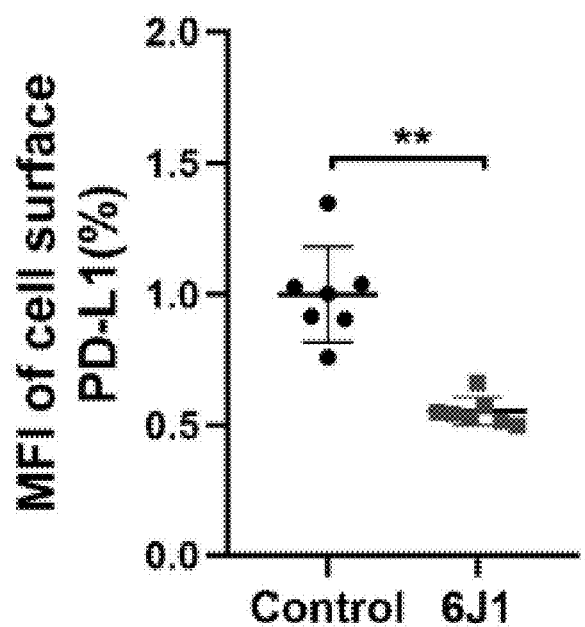
FIG. 15e is a graph showing a flow cytometry-based quantification of the levels of plasma membrane PD-L1 in the primary tumor.
Figure 15F:
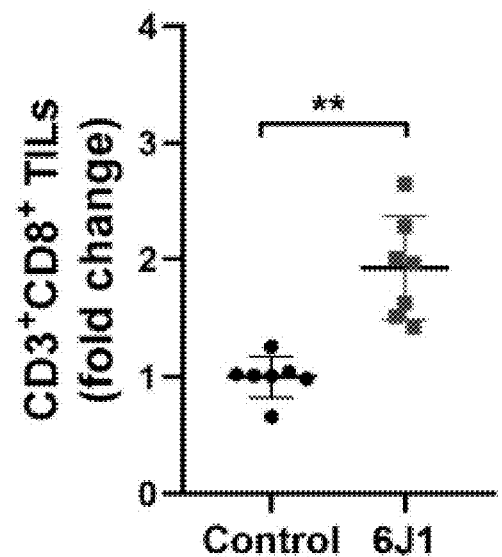
FIG. 15f is a graph showing fold change of CD3+CD8+ T-cell populations in the isolated tumors by flow cytometry analysis.
Figure 15G:
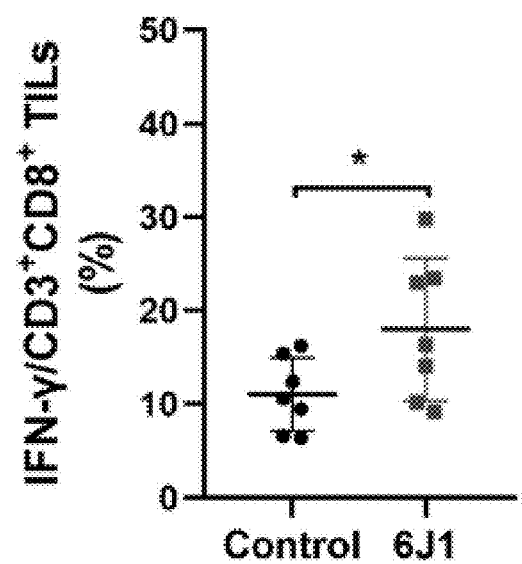
FIG. 15g is a graph showing the percentage of intracellular IFN-γ in the isolated tumor-infiltrating lymphocytes (TILs) by flow cytometry analysis.

FIG. 15*a*-15*c* shows the tumor growth of B16-F10 cell-implanted mice treated with buffer and 6J1. FIG. 15*d* illustrates the change of bodyweights. These results indicate that 6J1 markedly inhibits the growth of B16-F10 tumors without affecting the animal's body weight. FIG. 15*e* shows 6J1 significantly decreases the levels of PD-L1 at the cell surface of the primary tumors. FIG. 15*f* illustrates 6J1 markedly increases the percentage of tumor-infiltrating CD8+ T cell populations, while FIG. 15*g* shows it only subtly increases the expression of IFN-γ. These results demonstrate 6J1 also inhibits melanoma.

Figure 16A:
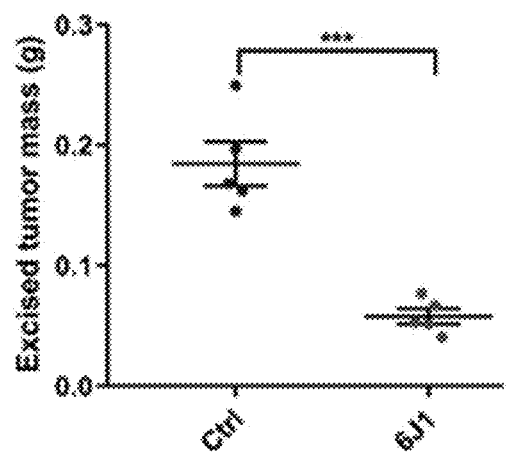
FIG. 16a is a graph showing the excised tumor masses of LL/2-cell-implanted C57BL mice treated with buffer or 6J1 (30 mg/kg, daily, oral gavage).
Figure 16B:
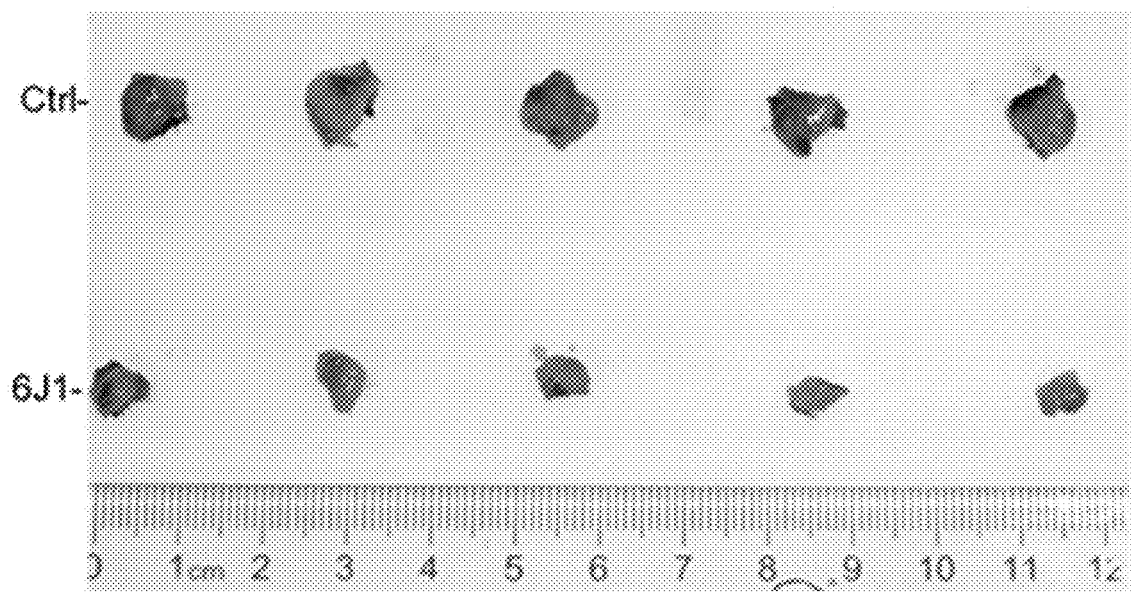
FIG. 16b is representative images of LL/2-cell-implanted C57BL mice treated with buffer or 6J1 (30 mg/kg, daily, oral gavage).
Figure 16C:
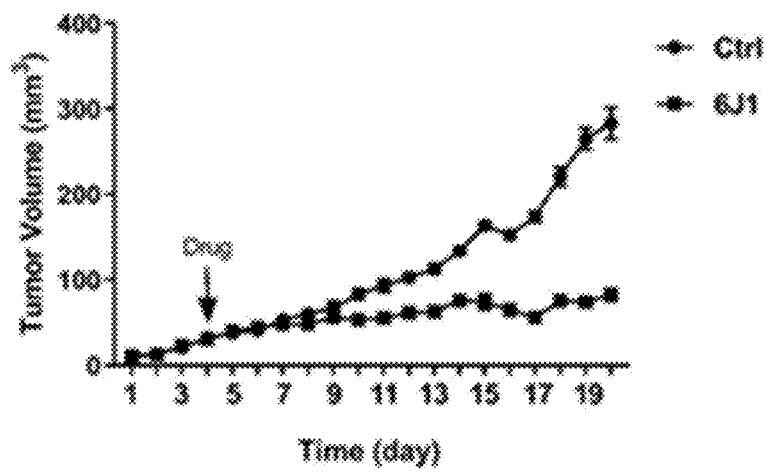
FIG. 16c is a graph showing daily tumor volumes of LL/2-cell-implanted C57BL mice treated with buffer or 6J1 (30 mg/kg, daily, oral gavage).

FIGS. 16*a*-16*c* show that 6J1 significantly inhibits the tumor growth in mouse lung cancer cells-implanted mice. FIGS. 16*a* and 16*b* show the lung tumor sizes at the end of the experiment. FIG. 16*c* shows the lung tumor growth on indicated days with or without 6J1.

FIG. 17*a* shows that 6J1 induces cell death in a concentration-dependent manner and 6J1 at its effective concentrations (i.e., ≤1 μM) hardly induces any cell death. FIG. 17*b* shows that 6J1 inhibits cell proliferation in a concentration-dependent manner and 6J1 at its effective concentrations (i.e., ≤1 μM) only subtly inhibits cell proliferation in several cell types. FIG. 17*c* shows that 6J1 exhibits little effect on the proliferation of or 4T1 cells at concentrations ≤1 μM.

FIGS. 18*a* and 18*b* show that 6J1 (30 mg/kg, oral, once per day) has no effects on mouse weight gain and weights of various organs. FIG. 18*c* shows that 6J1-treated mice show no apparent changes in liver function test. Also, FIG. 18*d* confirms that no signs of pathological changes in major organs of 6J1-treated mice are identified. These data indicate that the in vivo toxicity of 6J1 at therapeutic dose in mice is low. FIG. 18*e* shows that repeated daily dosing with 6J1 at dose levels ≥450 mg/kg is not tolerated as it is associated with mortality (1000 mg/kg) and severe clinical findings (450 and 1000 mg/kg) requiring moribund termination (450 and 1000 mg/kg) and interim termination (1000 mg/kg) of the treatment phase. Although repeated daily dosing (7 consecutive days) with 6J1 is considered tolerated up to 300 mg/kg, 6J1 (300 mg/kg)-related clinical signs are noted primarily towards the end of dosing (soft feces, hunched posture, and reduced feces) and baseline (Day-1) body-weight loss not exceeding 8% by Day 7. These results indicate that the therapeutic windows of 6J1 in experimental animals is at least 10 fold.

FIG. 19 shows the model of the anti-cancer effect of 6J1. 6J1 can reduce cell surface PD-L1 by inhibiting PD-L1's endosomal recycling process. In addition, the defect of endocytic trafficking caused by 6J1 facilitates exosomal PD-L1 secretion, which may suppress T cell activity in the tumor microenvironment. Inhibiting the exosomal PD-L1 secretion, in turn, enhances the antitumor immunity of 6J1.

Endosomal trafficking has been implicated in anti-cancer immunity, and here inventors explored the endosomal trafficking of PD-L1 in cancer cells. The plasma membrane PD-L1 is subjected to dynamic endosomal trafficking processes, from early endosomes to MVB/late endosomes, or to recycling endosomes, lysosomes, exosomes, or autophagosomes. Inventors synthesize a number of 6-morpholino-1,3, 5-triazine derivatives and identify a few of them as potent endosomal inhibitors, especially 6J1. Inventors find that treating cells with 6J1 inhibits the endosomal trafficking of PD-L1 and induces PD-L1 accumulated at endosomes. 6J1 also promotes PD-L1 secretion via exosomes, ultimately leading to the decrease of its level at the plasma membrane. In the orthotopic mouse model of 4T1 mouse mammary carcinoma, 6J1 subtly decreases tumor growth and increases cytotoxic T cells infiltration. RAB27 knockdown or GW4869 (an exosome secretion inhibitor) abolishes 6J1-induced PD-L1 exosomal secretion without changing its ability to lock PD-L1 at endocytic vesicles and decrease PD-L1 at the plasma membrane. The combination of 6J1 with RAB27 knockdown or GW4869 significantly promotes anti-cancer immunity, as manifested by the marked decrease in tumor growth accompanied by increased T cells and cytokine secretion in the primary tumors. Therefore, manipulation of PD-L1 endosomal trafficking by these 6-morpholino-1,3,5-triazine derivatives is a promising means to promote anti-cancer immunity in addition to the immune checkpoint antibody therapy.

The Endosomal Trafficking of Cell Surface PD-L1 is Clathrin- and RAB5-Dependent.

Without intending to be limited by theory, it is believed that the endosomal trafficking of PD-L1, a type I membrane protein, remains poorly studied thus far. In the fixed HeLa cells stained with anti-PD-L1 antibody, HeLa cells are plated on coverslips in 24-well plates and fixed after 24 h. Cells are then co-stained with antibodies against PD-L1 and Rab5, LAMP1, CD63, Rab27A, Rab11. It is believed that PD-L1 is expressed at both plasma membrane and cytoplasm, and the cytosol PD-L1 puncta exhibits colocalization with Rab5, CD63, LAMP1, Rab11, Rab27a, and LC3B (FIG. 1a). These data suggest that PD-L1 can colocalize with early endosomes, recycling endosomes, MVBs, Lysosomes, or/and autophagosomes. Thus, inventors speculate that PD-L1 at the cell surface may be subjected to an active endosomal trafficking process. To monitor the PD-L1's endosomal trafficking process, inventors label the PD-L1 at the cell surface in the live cells with an anti-PD-L1 antibody on ice for 1 h. They then incubate the cells with the warm medium at 37° C. for the indicated times to initiate the internalization of the PD-L1 antibody complex, followed by the immunostaining of RAB5, EEA1, LAMP1, or RAB11. The result shows that the internalized PD-L1 exhibits colocalization with these endosomes, lysosomes, or recycling endosomes markers (FIG. 1b). In addition, HeLa cells are pretreated with Fillilin III (5 mg/mL) or Pistop2 (30 uM) for 3 h, then stained with the anti-PD-L1 antibody on ice for 1 h. At the indicated times after being incubated with a warm medium at 37° C., the cells are fixed and stained with an anti-Rab5 antibody. Treatment of cells with Pitstop2, an inhibitor of clathrin-dependent endocytosis, blocks the internalization of PD-L1. However, Filipin III, an inhibitor of caveolae-mediated endocytosis, does not affect the internalization of PD-L1 (FIG. 1c). Furthermore, Rab5-knockout HeLa cells are transfected with CD63-mcherry and stained with the anti-PD-L1 antibody on ice for 1 h. After being incubated for 1.5 h in a warm medium at 37° C., the cells are fixed and imaged. As expected, RAB5 knockout significantly inhibits the internalization of PD-L1 and blocks its colocalization with CD63 (FIGS. 1d and 1e). These data suggest that the PD-L1 is subjected to clathrin-dependent endocytosis, and the PD-L1 endocytic vesicles then move from early endosomes (RAB5- or EEA1-positive) to either late endosomes (LAMP1-positive), or recycling endosomes (RAB11-positive).

HeLa cells are transfected with LC3B-RFP and stained with the anti-PD-L1 antibody on ice for 1 h. At the indicated times after being incubated at a warm medium at 37° C., the cells are fixed and imaged. Interestingly, internalized PD-L1 also exhibits strong colocalization with LC3B (FIGS. 1a and 2a). It has been previously shown that LC3 mediates the LC3-associated phagocytosis (LAP) to regulate vesicle trafficking from the cell membrane to the cytoplasm. To examine whether autophagy-related genes are involved in the endosomal trafficking of PD-L1, LC3B- or ATG5-knockout HeLa cells are transfected with CD63-mcherry and stained with the anti-PD-L1 antibody on ice for 1 h. After incubated for 1.5 h at a warm medium at 37° C., the cells are fixed and imaged. As shown in FIG. 2b, LC3B knockout does not affect the PD-L1's internalization and its association with CD63 (FIG. 2b). Similar results have also been observed in ATG5-knockout cells (FIGS. 2b and 2c). This data suggests that PD-L1's endosomal trafficking is independent of autophagy.

PD-L1 has been previously shown to be secreted outside the cell through exosomes. HeLa cells are plated on coverslips in 24-well plates and stained with the anti-PD-L1 antibody on ice for 1 h. At the indicated times after being incubated at a warm medium at 37° C., cells are fixed and stained with antibodies against CD63 or Rab27a. The result shows that the internalized PD-L1 exhibits strong colocalization with CD63, an MVB marker, and RAB27, an exosome secretion regulator (FIGS. 1a and 2d). Cells are treated with or without ionomycin (1 μM) for 48 h. The supernatant is collected and subjected to western blot analysis. Indeed, PD-L1 is detected in the exosomes, and ionomycin, a calcium ionophore that induces exosome secretion, markedly increased exosomal PD-L1 level (FIG. 2e). Since the amphisome, which is formed by the fusion of the autophagosome with the MVB/late endosome, has been implicated in extracellular vesicles secretion, and PD-L1 is found to be associated with LC3B during PD-L1 trafficking (FIG. 2a), inventors examine whether the autophagosome formation is involved in exosomal PD-L1 secretion. Thus, inventors knock out the expression of Rab27A, LC3B or ATG4B in HeLa cells and collect their supernatant respectively for western blot analysis. The result shows that LC3B or ATG4B knockout does not affect exosomal PD-L1 levels, whereas RAB27A knockout markedly reduces it (FIG. 2f).

Furthermore, HeLa cells are treated with or without Bafilomycin A1 (10 nM), or Torin 1 (100 nM) for 48 h. The cell lysates and supernatant are collected for western blot analysis. Interestingly, bafilomycin A1 (BafA1), a vacuolar H+ ATPase inhibitor that blocks the fusion between lysosomes and autophagosomes or late endosomes, markedly increases not only total PD-L1 levels in cells, but also exosomal PD-L1 levels. In contrast, Torin1, an autophagy activator, has little effect on total and exosomal PD-L1 levels (FIG. 2g). These results indicate that autophagy is not essential for PD-L1 exosomal secretion. On the other hand, blockage on the fusion between lysosomes and late endosomes or autophagosomes may induce PD-L1 secretion via exosomes.

Identification of 6J1, a 6-Morpholine-1,3,5-Triazine Derivative, as a Potent Modulator of PD-L1 Endosomal Trafficking.

When PD-L1 is subjected to dynamic endosomal trafficking, BafA1 markedly induces PD-L1 secretion via exosomes by blocking fusion between lysosomes and late endosomes (FIGS. 1a-1f and 2a-2e). Inventors reason that targeting the endocytic trafficking of PD-L1 may reduce cell surface PD-L1 level, thereby blocking the PD-L1/PD1 signaling to promote anti-cancer immunity. Therefore, a series of synthesized 6-morpholine-1,3,5-triazine derivatives aim to identify potent and less cytotoxic compounds to manipulate the endosomal trafficking of PD-L1 (FIGS. 3a and 3b).

A DQ-BSA endocytic trafficking assay screens these compounds. DQ-BSA, a self-quenching dye, is internalized into the cytoplasm by endocytosis, after which it is delivered to the lysosomes for degradation to relieve fluorescence-quenching, resulting in bright fluorescence in cells. HeLa cells are plated on 6-well plates and treated with the indicated compound for 3 h. Then, cells are replaced with Trafficking media containing 10 μg/ml DQ-green BSA with or without drugs (1 μM) and incubated at 37° C. in a 5% $CO_2$ humidified cell culture chamber another 6 h followed by Flow cytometry analysis. Interestingly, several 6-morpholine-1,3,5-triazine derivatives, including 6J1, C3, C4, D3, D4, H1, and P2, dramatically inhibit endocytic trafficking, manifested by their ability to inhibit fluorescence intensity of DQ-BSA-labeled cells (FIG. 4a). Inventors also test whether these hit compounds can inhibit the recycling endosomal pathway by performing the fluorescent transferrin conjugates recycling assay. Iron-bound transferrin interacts with its receptor (TfR) to trigger the internalization of the iron-transferrin-TfR complex via clathrin-mediated endocytosis. $Fe^{3+}$ irons are subsequently dissociated from their ligands in the acidic endosome environment and released into the cytoplasm. After that, the transferrin-TfR complex is recycled back to the plasma membrane, and transferrin is finally released from its receptor into the extracellular space. Thus, the fluorescence intensity of fluorescent transferrin conjugates-labeled cells can reflect the recycling endocytic trafficking process. HeLa cells are plated on 6-well plates and treated with the indicated compound for 3 h. Then, cells are incubated with Transferrin-488(25 μg/ml) on ice for 1 h followed by incubating in the complete medium at 37° C. in a $CO_2$ incubator for 3 h. Cells are collected for flow cytometry analysis, and the mean fluorescence intensity of transferrin is quantified. The result shows that these 6-morpholine-1,3,5-triazine derivatives, especially 6J1, effectively inhibit the recycling endosomal trafficking of transferrin (FIG. 4b).

Furthermore, HeLa cells are pretreated with DMSO or 6J1 (1 μM) for 3 h. Then, cells are incubated with EGF-488 (2 μg/ml) on ice for 1 h followed by incubating in the complete medium at 37° C. in a $CO_2$ incubator. Cells are fixed at the indicated times and imaged. The result shows that 6J1 blocks the EGFR degradation, manifested by locking the EGFR complex on the endosomes in 6J1-treated cells after 2 h of EGF treatment compared to the control cells in which the EGFR is completely degraded after 2 h of EGF treatment (FIG. 4c). Collectively, these results indicate that 6J1 is a potent endosomal trafficking inhibitor but does not impair the internalization of membrane proteins or extracellular ligands.

Next, inventors assess if 6J1 can compromise PD-L1 trafficking. PDL1-GFP stable expressing HeLa cells are treated with or without 6J1 (1 μM) for 24 h. Cells are fixed and stained with Rab5 or EEA1. Their quantifications of the colocalization are shown in FIGS. 4d and 4e, respectively. The results show that 6J1 treatment clearly induces the accumulation of PD-L1 within vesicle-like structures in the cytoplasm, and these vesicles colocalize with the early endosome markers, EEA1 and RAB5 (FIGS. 4d and 4e). Interestingly, following 6J1 treatment, the cell membrane PD-L1 level seems weaker than the control cells (FIG. 4g). Inventors thus further quantify cell membrane PD-L1 levels in live cells treated with or without 6J1 by flow cytometry or confocal imaging. Indeed, 6J1 significantly reduces the expression of PD-L1 on the surface of cells (FIGS. 4f-4g).

These data indicate 6J1 induces the accumulation of PD-L1 in the endosomal compartment and reduces the expression of PD-L1 at the cell surface.

6J1 Induces Exosomal PD-L1 Secretion.

It has previously been shown that interfering with endosomal trafficking promotes exosome secretion. Moreover, PD-L1 has been reported to be enriched in exosomes and secreted outside the cell. Thus, inventors speculate that 6J1 may induce the secretion of the PD-L1 trapped in the endosomal compartments via exosomes. To determine whether 6J1 may induce the secretion of PD-L1 via exosomes, HeLa cells are treated with or without 6J1 (1 μM) for 24 h. The supernatant is collected. Inventors purify the exosomes from the supernatant of HeLa cells by sequential centrifugation. The concentration of extracellular vesicle is determined using a Nanosight nanoparticle analyzer. And HeLa cells are treated with or without 6J1 (1 μM) for 48 h. The cell and supernatant are collected for Western Blot analysis. The result shows that 6J1 dramatically induces exosome secretion and increases PD-L1 level in exosomes (FIGS. 5a and 5b). Likewise, 6J1 significantly induces the colocalization of PD-L1 with the exosomal markers, e.g., TSG101, CD63, and Rab27A (FIGS. 5c-5e). Whereas 6J1 markedly decreases the colocalization between PD-L1 and RAB11 (the recycling endosome marker) (FIG. 5f). Moreover, the activity of Rab27a in HeLa cells treated with or without 6J1 (1 μM) is examined with a GST-SHD pulldown assay. Compound 6J1 significantly increases the activity of Rab27a-GTPase, which may contribute to the increased exosome secretion in 6J1-treated cells (FIG. 5g-5h). These data indicate that 6J1 can increase Rab27a-GTPase activity to promote exosomal PD-L1 secretion.

HeLa cells are treated with or without 6J1. After 6 h, cells are collected for western blot analysis of LC3 and p62. Interestingly, 6J1 also markedly induced an increase in the level of LC3B-II and P62 (FIG. 6a). Likewise, 6J1 significantly induces the formation of yellow LC3B puncta in GFP-RFP-LC3-expressing HeLa cells, and no red-only LC3B puncta are observed in 6J1-treated cells (FIG. 6b). These results suggest that 6J1 inhibits the autophagosome and lysosome fusion. In addition to its canonical degradative function, autophagy has been shown to participate in the secretion of cytosolic proteins and exosome biogenesis. In addition, ATG5-knockout HeLa cells are transfected with PD-L1-GFP and LC3-RFP, and then treated with or without 6J1 (1 μM) for 24 h. Cells are fixed and imaged. Inventors also find that PD-L1-containing vesicles are strongly colocalized with LC3B puncta in 6J1-treated cells. ATG5 knockout significantly reduces LC3B punta and abolishes this colocalization between PD-L1 and LC3B on the cells treated with 6J1 yet has no effect on 6J1-induced PD-L1 puncta (FIG. 6c). Furthermore, LC3B-knockout HeLa cells are transfected with PD-L1-GFP, and then treated with or without 6J1 (1 μM) for 24 h. Cells are fixed and stained with antibodies against Rab5 (FIG. 6d) or Rab27a (FIG. 6e). Likewise, LC3B knockout does not affect the 6J1-induced PD-L1 puncta and the colocalization between PD-L1 and RAB5 or RAB27A (FIGS. 6d and 6e).

Moreover, ATG5- or LC3-knockout HeLa cells are treated with or without 6J1 (1 μM) for 24 h. The supernatant is collected, and the concentration of the extracellular vesicle is determined using a Nanosight nanoparticle analyzer. The exosomes are also collected and subjected to western blot analysis of the EVs marker and PD-L1 in FIG. 7a. The live cells are also labeled with an anti-PD-L1 antibody in FIG. 7b and subjected to flow cytometry analysis in FIG. 7c. Neither ATG5 nor LC3B knockout impairs the 6J1-induced EVs secretion (FIG. 7a), exosomal PD-L1 secretion (FIG. 7b), and the decrease in the level of PD-L1 at the cell surface (FIG. 7c). In addition, inventors assess whether other autophagy-related genes, e.g., ATG4B, ATG7, Beclin1, and Vps34 are involved in 6J1-mediated exosomal PD-L1 secretion. ATG4B-, ATG7-, Beclin1-, or VPS34-knockout HeLa cells are treated with or without 6J1 (1 µM) for 24 h. The supernatant is collected, and the concentration of extracellular vesicle is determined using a Nanosight nanoparticle analyzer. The exosomes are also collected and subjected to western blot analysis of the EVs marker and PD-L1 in FIG. 7d. The live cells are also labeled with an anti-PD-L1 antibody and subjected to flow cytometry analysis in FIG. 7e. The results showed that the knockout of the aforementioned genes fails to abolish 6J1-induced EVs secretion and exosomal PD-L1 secretion (FIG. 7d). The flow cytometry data also confirms that knockout of these autophagy genes does not affect the 6J1-mediated decrease in the level PD-L1 at the cell surface (FIG. 7e-7f). Notably, knockout individual autophagy genes have differential effects on the basal levels of PD-L1 in exosomes and at the cell surface, again suggesting that these genes, not the canonical autophagy pathway, may participate in various aspects of PD-L1 endosomal trafficking individually. In summary, these data indicate that 6J1-induced exosomal PD-L1 secretion and a decrease in the amount of cell surface PD-L1 is dispensable of canonical autophagy.

6J1 Suppresses Breast Cancer Growth In Vivo.

The current PD-L1 and PD1 therapies apply PD-L1 or PD1 monoclonal antibodies to block the PD-L1/PD1 signaling, which results in cytotoxic T cells recognizing and killing the tumor cells. Since 6J1 significantly decreased the cell surface PD-L1 levels, inventors speculate that 6J1 may reduce the cell surface PD-L1 levels in tumors to mitigate the inhibition on T cells in vivo, thus showing a similar anti-cancer effect as PD-L1 or PD1 blockade therapy. First, flow cytometry-based quantification of plasma membrane levels of PD-L1 in 4T1 cells treated with or without 6J1 (1 µM) for 24 h. 4T1 cells are treated with or without 6J1 (1 µM) for 24 h. The supernatant is collected, and the concentration of extracellular vesicle is determined using a Nanosight nanoparticle analyzer in FIG. 8b. The exosomes are also collected and subjected to western blot analysis of the EVs marker and PD-L1 in FIG. 8c. The results confirm that in 4T1 mouse mammary carcinoma cells, 6J1 decreases the level of cell surface PD-L1 and induces the secretion of PD-L1 in exosomes (FIGS. 8a-8c). Then, an in vitro T cell-mediated tumor cell killing assay shows that 4T1 cells treated with 6J1 are more sensitive to pre-activated T cell-mediated cytolysis when compared to the control cells (FIG. 8d), suggesting that 6J1 may promote anti-cancer immunity.

Figure 8K:
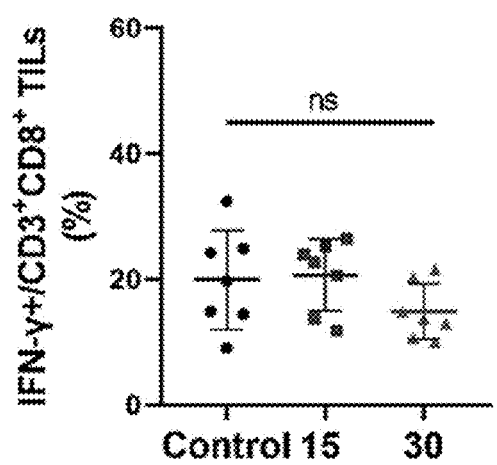
FIG. 8k is a graph showing the intracellular cytokine stains of IFN-γ from the isolated tumor-infiltrating lymphocytes.

To determine whether 6J1 can promote anti-cancer immunity in vivo, 4T1 cells are orthotopically transplanted into syngeneic Balb/c mice. The mice are randomly divided into three groups (n=7 per group) and treated with either buffer or 6J1 (15 or 30 mg/kg, daily) via oral gavage. Tumor volume and body weight of mice are measured at the indicated time point. After the tumor reaches the indicated size, the mice are treated with 6J1 (via oral gavage) at different doses (15 mg/kg or 30 mg/kg) daily for 4 weeks. It shows that 6J1 significantly decreases the tumor growth at the dose of 30 mg/kg but does not change the body weight of mice (FIGS. 8e-8h). Interesting, in mice treated with 6J1 (30 mg/kg), the cell surface expression of PD-L1 is downregulated in the primary tumors (FIG. 8i). 6J1 also significantly increases the tumor-infiltrating CD8+ T cell populations (FIG. 8j) but had little effect on the expression of IFN-γ in CD8+ T cells (FIG. 8k). The effective dosages of 6J1 in vivo can range from about 0.1 mg/kg to about 300 mg/kg; or from about 1 mg/kg to about 200 mg/kg; or from about 3 mg/kg to about 100 mg/kg, taking into account, for example, activity and toxicity 6J1 Induces Chemokine Secretion in the Tumor Microenvironment.

Inventors further measure the chemokines or cytokines in these primary tumor tissues. The tumors are isolated at the end of experiments, and the chemokine levels in the microenvironment of 4T1 primary tumors treated with the vehicle or 6J1 are determined by Flow cytometry-based quantification. In FIGS. 9a-9c, data are reported in µg/ml, standardized to the excised tumor weight (in grams); each dot represents one mouse. The result shows that in the tumor microenvironment of 4T1 tumors, 6J1 significantly increases the secretion of some chemokines (e.g., CCL2, CCL3, CCL4, and CXCL9) (FIG. 9a), but it has little or only subtly effects on others (e.g., CCL5, CCLII, CCL17, CCL22, CXCL1, CXCL5, CXCL10, and CXCL13) (FIG. 9a). In vitro, 6J1 also markedly induces the secretion of various chemokines from 4T1 cells and Raw246.7 cells (FIGS. 9b and 9c). These results suggest that the ability of 6J1 to induce the secretion of inflammatory cytokines might turn the immune-cold microenvironment of 4T1 tumors into immune-hot, thereby recruiting more cytotoxic T cells to it, but these T cells appear to be exhausted.

To assess whether the in vivo antitumor growth effect of 6J1 is related to its effect on PD-L1 in 4T1 cells, inventors knock out PD-L1 via CRISPR/Cas9 in 4T1 cells (FIG. 10a). 4T1-NC or 4T1-PD-L1 knockout cells are treated with or without 6J1 (1 µM) for 24 h. The supernatant is collected, and the concentration of extracellular vesicle is determined using a Nanosight nanoparticle analyzer. The exosomes are also collected and subjected to western blot analysis of the EVs marker and PD-L1. The result shows that PD-L1 knockout in 4T1 cells does not affect 6J1-induced EVs secretion in 4T1 cells (FIG. 10b), but dramatically decreases the expression of PD-L1 in exosomes isolated from cells treated with or without 6J1 (FIG. 10c). Inventors then transplant control or PD-L1-knockout 4T1 cells into the fat pad of syngeneic female Balb/c mice. The mice are randomly divided (n=5 per group) and treated with either buffer or 6J1 (30 mg/kg, daily) via oral gavage. The result shows that PD-L1 knockout significantly suppresses tumor growth than the control group, and 6J1 treatment fails to decrease further tumor growth in mice implanted with PD-L1-knockout 4T1 cells (FIGS. 10d-10g). These results indicate that the level of PD-L1 expression is an essential factor for tumor growth of 4T1 cells in vivo, and is, at least partially, involved in the anti-cancer effects of 6J1.

Blocking Exosome Secretion Significantly Enhances the 6J1's Anti-Cancer Effect

The exosomal PD-L1 has been shown to suppress the function of CD8 T cells, hence facilitating tumor growth. Therefore, it is possible that the increased exosomal PD-L1 secretion induced by 6J1 may still suppress the tumor-infiltrating T cell cytotoxicity in vivo, even though 6J1 reduces the cell surface expression level of PD-L1 on the tumor cells. To evaluate the role of exosomal PD-L1 in the tumor microenvironment and tumor progression in mice, inventors knock out Rab27a in 4T1 cells to inhibit the secretion of exosomes. 4T1-shNC or 4T1-shRab27A cells are treated with or without 6J1 (1 µM). The supernatant is collected, and the concentration of extracellular vesicle is determined using a Nanosight nanoparticle analyzer. As expected, the knockout of Rab27a significantly inhibits 6J1-induced EVs secretion (FIGS. 11a-11b) and exosomal PD-L1 levels (FIG. 11c). Inventors analyze the plasma membrane levels of PD-L1 in 4T1-shNC or 4T1-shRab27A cells treated with or without 6J1 (1 µM). However, the knockout of Rab27a does not influence the 6J1-induced decrease of cell surface PD-L1 levels (FIG. 11d). Next, control or Rab27a-knockout 4T1 cells are orthotopically transplanted into syngeneic fat pads of female Balb/c. The mice are randomly divided (n=5 per group) and treated with either buffer or 6J1 (30 mg/kg, daily) via oral gavage. The tumor growth and tumor burden in mice implanted with Rab27a-knockout 4T1 cells and treated with 6J1 are significantly smaller than those in mice implanted either with control 4T1 cells treated with or without 6J1, or with Rab27a-knockout 4T1 cells without 6J1 treatment (FIGS. 11e-11h). Consistently, the activated tumor-infiltrating CD8+ T cell population and expression of IFN-γ are significantly increased in the primary tumor isolated from mice implanted with Rab27a-knockout 4T1 cells and treated with 6J1, when compared to those in other groups (FIGS. 11i-11j). Inventors also perform the immunostaining of CD8 and Granzyme B in the tumor sections. As expected, more infiltrated CD8$^+$ T cells are detected in tumors isolated from mice implanted with RAB27a-knockout 4T1 cells and treated with 6J1 compared to samples from other groups (FIG. 11i). Since enhanced antitumor immunity leads to increased apoptosis in tumors, inventors assess the levels of cleaved caspase3 (CCA3), one of the markers of apoptosis, in tumor sections as well. Stronger clustered apoptotic signals are observed in the tumors from mice implanted with Rab27a-knockout 4T1 cells and treated with 6J1 compared to other groups (FIG. 11l-11m). Moreover, the combination of Rab27a knockout and 6J1 treatment substantially prolongs the overall survival of mice bearing orthotopic 4T1 tumors compared with other groups (FIG. 11k). Therefore, these results indicate that blocking exosomal PD-L1 secretion increases the antitumor immunity of 6J1.

Inventors also implant control or Rab27a-knockout 4T1 cells into the fat pads of female Balb/c nude mice. The mice are randomly divided (n=4 per group) and treated with either buffer or 6J1 (30 mg/kg, daily) via oral gavage. The result shows that Rab27a knockout has little effect on the tumor size and the bodyweight in these immunocompromised mice. The anti-cancer effect of 6J1 or the combination of 6J1 and Rab27a knockout is also dramatically abolished in the immunocompromised mouse model (FIGS. 12a-12e). These results again support that 6J1 may promote anti-cancer immunity in mice.

Finally, inventors assess the combinatory effects of 6J1 with GW4869, an exosome secretion inhibitor, in the aforementioned orthotopic mammary carcinoma mouse models. Inventors find that GW4869 inhibits exosome secretion of 4T1 cells induced by 6J1 (FIG. 13a), whereas it does not impair 6J1-mediated reduction of cell surface PD-L1 (FIGS. 13b-13c). Furthermore, 4T1 cells are injected into the fat pads of female Balb/c mice. The mice are randomly divided into four groups (n=5 per group) and treated with buffer, 6J1 (30 mg/kg, oral, daily), GW4869 (2.5 mg/kg, IP, daily), or 6J1 and GW4869, respectively. Similar to Rab27a knockout, the combination of GW4869 and 6J1 suppresses tumor growth and decreases tumor burden more effectively than GW4869 or 6J1 alone (FIGS. 13d-13g). These data indicate that the inhibition of exosome secretion by either pharmacological inhibitors or a genetic approach in tumor cells significantly augments the anti-cancer efficacy of 6J1 in vivo.

A Combination of 6J1 and Anti-PD-1 Antibodies Promotes Anticancer Immune Responses.

The above results suggest that 6J1 induces the secretion of exosomal PD-L1 into the tumor microenvironment, and this exosomal PD-L1 may bind to PD-1 on T cells and, in this way suppress their antitumor activity. Inventors hypothesize that a neutralizing anti-PD-1 antibody may be able to prevent such exosomal PD-L1/PD-1 binding. So, a combination of 6J1 and anti-PD-1 antibodies may exhibit better anti-cancer activity than either of these treatments alone.

Anti-PD-1 antibodies block the PD-1 receptor so the T cells are no longer inhibited and therefore activate the immune response against the tumor. Nivolumab (available from Ono Pharmaceuticals/Bristol-Meyers Squibb), Pembrolizumab (available form Merck), and Cemiplimab (available from Regeneraon Pharmaceuticals) are examples of approved antibodies. The in-vivo experiments use Anti-mouse PD-1, the 29F.1A12 monoclonal antibodies. 4T1 cells are injected into the mammary fat pad of syngeneic Balb/C mice. The mice are randomly divided (n=6 per group). After tumors reach around 5 mm, they are treated with either buffer or 6J1 (30 mg/kg, daily, oral gavage) and/or anti-PD1 antibody (200 µg/per mouse, every 3 days, IP) for 4 weeks. The tumor sizes are measured every week. After 4 weeks, the primary tumors and lungs are collected for analysis. The tumor growth and tumor burden in 4T1 cell-implanted mice treated with both 6J1 and anti-PD-1 antibodies are significantly weaker than 4T1 cell-implanted mice treated with 6J1 or anti-PD-1 antibody alone (FIGS. 14a-14d). Moreover, the expressions of CD8 and granzyme B, and cleaved Caspase3 in the primary tumors are determined by immune-labeling. An increasing number of infiltrated CD8+ T cells and stronger granzyme B signals are detected in tumor sections isolated from mice treated with both 6J1 and anti-PD-1 antibodies, compared to those treated with 6J1 or anti-PD-1 antibody (FIG. 14e). Likewise, the larger areas of CCA3 signal are detected in tumor sections from 4T1-implanted mice treated with both 6J1 and anti-PD-1 antibodies, compared with either treatment alone (FIG. 14f). These results demonstrate that 6J1 promotes the anti-cancer immunity of the anti-PD-1 antibody and vice versa. Therefore, manipulation of PD-L1 endosomal trafficking by small chemicals provides an effective strategy to promote anti-cancer immunity, in addition to the existing immune checkpoint inhibitors.

6J1 Suppresses the Growth of Primary Tumors in Syngeneic Mouse Models.

Inventors also examine the anti-cancer effect of 6J1 in a melanoma xenograft mouse model, by the subcutaneous injection of B16-F10 cells in syngeneic C57BL mice. B16-F10 cells are subcutaneously injected into the flank of female C57BL/6J mice. The mice are randomly divided (n=6 per group). They are treated with either buffer or 6J1 (30 mg/kg, daily, oral gavage) after tumors reach around 5 mm for 4 weeks. After 4 weeks, the primary tumors are collected for analysis. The result shows that 6J1 markedly inhibits the growth of B16-F10 tumors (FIGS. 15a-15c) without affecting the animal's body weight (FIG. 15d). In addition, a flow cytometry-based quantification of the levels of plasma membrane PD-L1 in the primary tumor is performed in FIG. 15e. 6J1 significantly decreases the levels of PD-L1 at the cell surface of the primary tumors (FIG. 15e). In B16-F10 tumors, fold change of CD3+CD8+ T-cell populations, and percentage of intracellular IFN-γ in the isolated tumor-infiltrating lymphocytes (TILs) are determined by flow cytometry analysis in FIGS. 15f and 15g. Similar to 4T1 tumors, 6J1 also markedly increases the percentage of tumor-infiltrating CD8+ T cell populations (FIG. 15f), but only subtly increases the expression of IFN-γ (FIG. 15g) when compared with the control groups.

Similarly, 6J1 significantly inhibits the tumor growth of mouse lung cancer (FIGS. 16a-16c). C57BL mice (n=5) are injected subcutaneously with LL/2 cells. After tumors reach around 5 mm in size, the mice are treated with either buffer (PBS) or 6J1 (30 mg/kg, daily, oral gavage) for 4 weeks. After 4 weeks, primary tumors and lungs are collected for analysis (FIGS. 16a and 16b). Tumor volumes are measured daily (p<0.001) in FIG. 16c.

The inventors also test the cytotoxicity of 6J1 in several cancer cell lines, HeLa, A549 and MDA-MB-231 cell lines. Cells are grown in 96-well plates in triplicate and treated with or without 6J1 at the concentrations of 0, 0.01, 0.1, 1, 10 and 100 μM indicated for 24 h or 48 h. They are then stained with propidium iodide (PI) or Hochest 33342 to measure the cell death ratio and cell number, respectively. The results show that 6J1 induces cell death and inhibits cell proliferation in a concentration-dependent manner (FIGS. 17a and 17b). Yet, 6J1 at its effective concentrations (i.e., ≤1 μM) hardly induces any cell death, and only subtly inhibits cell proliferation in several cell types (FIGS. 17a and 17b). Inventors also test the cytotoxicity of 6J1 in 4T1 cells. 4T1 cells are plated in 96-well plates in triplicate and treated with or without 6J1 at the concentrations of 0, 0.01, 0.1, 1, 5, 10, 20, 40, 80 and 100 μM indicated for 24 h or 48 h. The cell viability was then quantified via the MTT assay. The result shows that when used at concentrations ≤1 μM, 6J1 exhibits little effect on the proliferation of 4T1 cells (FIG. 17c). Therefore, these results suggest that cells tolerate the decreased endosomal trafficking processes.

The Subchronic Toxicity of 6J1 in Mice is Low

Last, inventors investigate the in vivo toxicity of 6J1 in mice. 6-week-old Balb/C mice are treated with vesicle control (PEG400/Ethanol/tween80, 1:1:1) or 6J1 (30 mg/kg, per day) via oral route for 4 weeks. Clinical observations, e.g., food consumption, body weight changes, and ophthalmic exams, are performed every three days. Tissue weight index (tissue weight/body weight×100%) are measured. The 6J1-treated mice show no signs of behavior abnormality. 6J1 has no effects on mouse weight gain and weights of various organs (FIGS. 18a and 18b). At the end of experiment, the blood is collected from mice in each group for AST, ALT, and ALP measurement. The mice are then sacrificed, and the major organs are isolated, examined, and subjected to H&E staining. 6J1-treated mice show no apparent changes in liver function test (FIG. 18c). Also, no signs of pathological changes in major organs of 6J1-treated mice are identified (FIG. 18d). In summary, these data indicate that the in vivo toxicity of 6J1 at therapeutic dose in mice is low.

Inventors also evaluate the toxicity profile following oral gavage administration of 6J1 at dose levels of 0 (vehicle), 150, 450, and 1000 mg/kg once daily for up to 7 consecutive days to rats. Rats of the 300 mg/kg group are tested separately from other groups (showing higher initial weight than other groups), and rats of 450 and 1000 mg/kg groups are terminated on day 4 due to several clinical findings. The result shows that repeated daily dosing with 6J1 at dose levels ≥450 mg/kg is not tolerated as it is associated with mortality (1000 mg/kg) and severe clinical findings (450 and 1000 mg/kg) requiring moribund termination (450 and 1000 mg/kg) and interim termination (1000 mg/kg) of the treatment phase. Although repeated daily dosing (7 consecutive days) with 6J1 is considered tolerated up to 300 mg/kg, 6J1 (300 mg/kg)-related clinical signs are noted primarily towards the end of dosing (soft feces, hunched posture, and reduced feces) and baseline (Day-1) bodyweight loss not exceeding 8% by Day 7 (FIG. 18e). Nevertheless, these results indicate that the therapeutic windows of 6J1 in experimental animals is at least 10 fold.

Taken together, these results indicate that 6J1 (a triazine compound with good oral bioavailability and subtle in vitro and in vivo toxicity), blocks the endosomal trafficking of PD-L1 and induces its exosomal secretion by activating Rab5 and Rab27, respectively. This ultimately leads to a decrease of PD-L1 at the plasma membrane. 6J1 also markedly increases the number of tumor-infiltrated cytotoxic T cells and promotes the secretion of various proinflammatory chemokines in the tumor microenvironment. In addition, a combination of 6J1 with the inhibition of exosomal PD-L1 secretion or with a PD-1 monoclonal antibody, both significantly promote the anticancer immune response (FIG. 19). Therefore, manipulation of PD-L1 endosomal trafficking by small chemicals provides an alternative strategy to promote anti-cancer immunity, in addition to existing antibody drugs to block the immune checkpoint.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

All references specifically cited herein are hereby incorporated by reference in their entireties. However, the citation or incorporation of such a reference is not necessarily an admission as to its appropriateness, citability, and/or availability as prior art to/against the present invention.

What is claimed is:

1. A method of inhibiting endosomal trafficking of PD-L1, comprising the step of administering a compound of Formula I to a cancer or tumor cell:

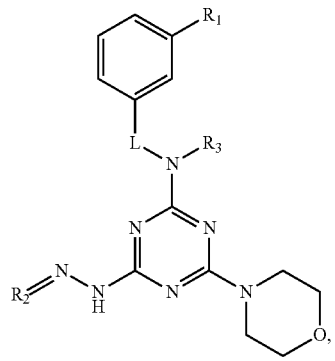

Formula I wherein R1 is selected from the group consisting of a hydrogen atom, a halogen atom and a halogenated group;

R2 is selected from the group consisting of

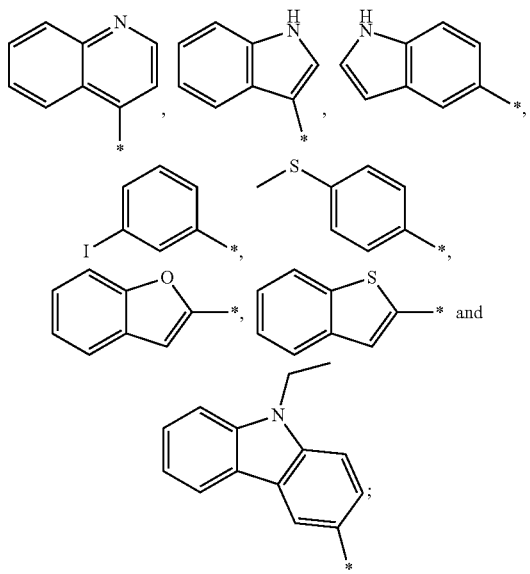

R3 is a hydrogen atom or

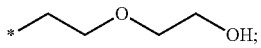

and

L is a linker group, —(CH$_2$)$_n$—, where n is an integer from 0-5.

2. The method of claim 1, wherein the inhibition of endosomal trafficking of PD-L1 comprises an inhibition of endocytic trafficking of PD-L1.

3. The method of claim 1, wherein the inhibition of endosomal trafficking of PD-L1 comprises an inhibition of recycling endosomal trafficking of PD-L1.

4. A method of inducing PD-L1 secretion via exosomes, comprising the step of administering a compound of Formula I to a cancer or tumor cell:

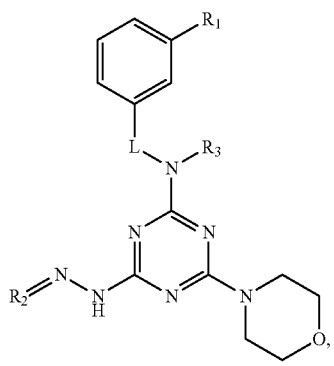

Formula I wherein R1 is selected from the group consisting of a hydrogen atom, a halogen atom and a halogenated group;

R2 is selected from the group consisting of

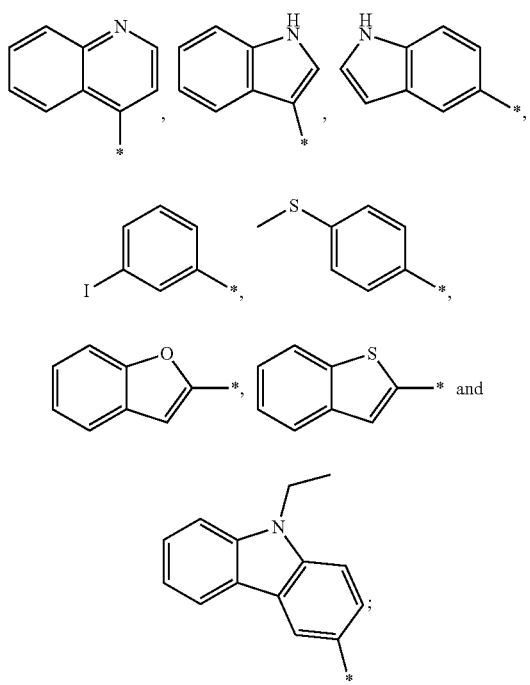

R3 is a hydrogen atom or

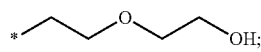 [SMILES: *CCOCCO]

and

L is a linker group, —(CH$_2$)$_n$—, where n is an integer from 0-5.

5. The method of claim 4, wherein the compound activates Rab27a to induce PD-L1 secretion via exosomes.

6. A method of decreasing PD-L1 level at a surface of a cancer or tumor cell, comprising the step of administering a compound of Formula I to a cancer or tumor cell:

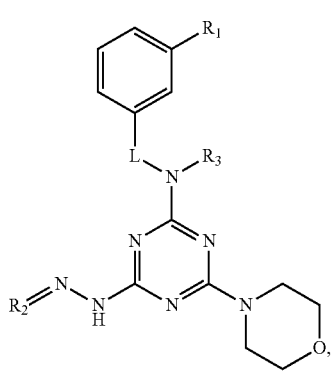

Formula I wherein R1 is selected from the group consisting of a hydrogen atom, a halogen atom and a halogenated group;

R2 is selected from the group consisting of

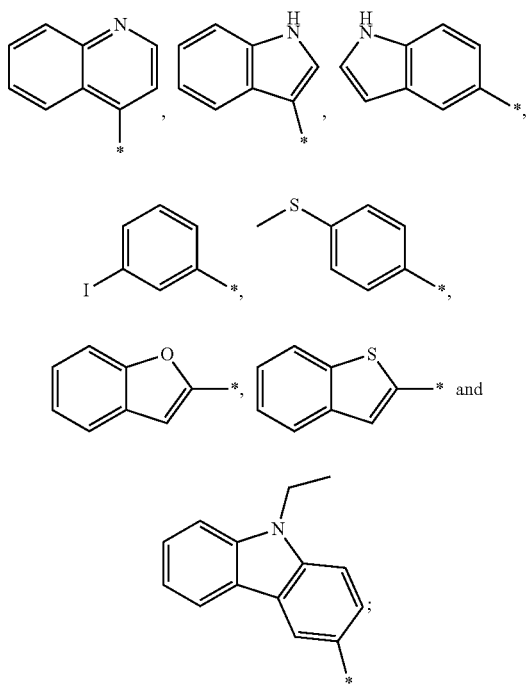

R3 is a hydrogen atom or

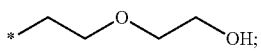

and

L is a linker group, —(CH$_2$)$_n$—, where n is an integer from 0-5.

7. A method of promoting T cell immune response in a subject suffering from a cancer or tumor, comprising the step of administering an effective amount of a compound of Formula I:

Formula I

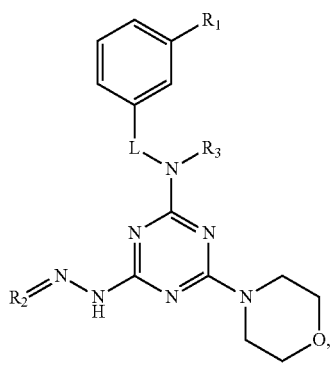

wherein R1 is selected from the group consisting of a hydrogen atom, a halogen atom and a halogenated group;

R2 is selected from the group consisting of

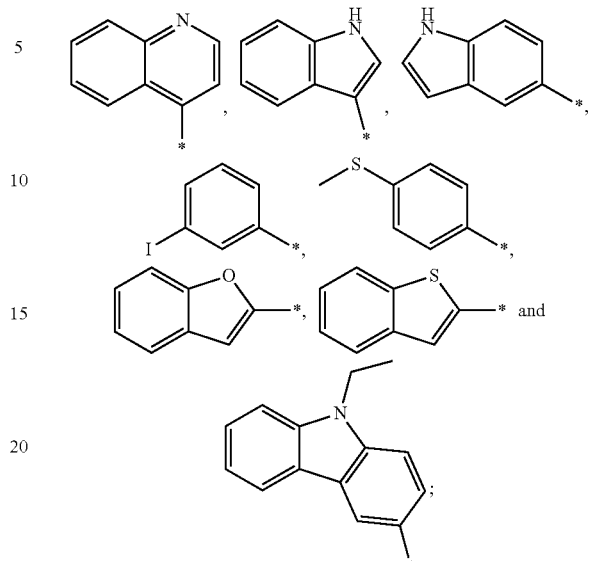

R3 is a hydrogen atom or

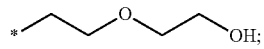

and

L is a linker group, —(CH$_2$)$_n$—, where n is an integer from 0-5, and wherein the cancer is selected from the group consisting of lung cancer, pancreatic cancer, breast cancer, colon cancer, colorectal cancer, melanoma, gastrointestinal cancer, gastric cancer, renal cancer, ovarian cancer, liver cancer, endometrial cancer, kidney cancer, prostate cancer, thyroid cancer, neuroblastoma, glioma, glioblastoma, cervical cancer, stomach cancer, bladder cancer, head and neck cancer, hepatoma and a combination thereof.

8. The method of claim 7, wherein the compound induces chemokine secretion in the tumor microenvironment to promote T cell immune response.

9. The method according to claim 1, wherein R1 is selected from the group consisting of a hydrogen atom, a fluorine atom and —CF3.

10. The method according to claim 1, wherein the compound is selected from the group consisting of

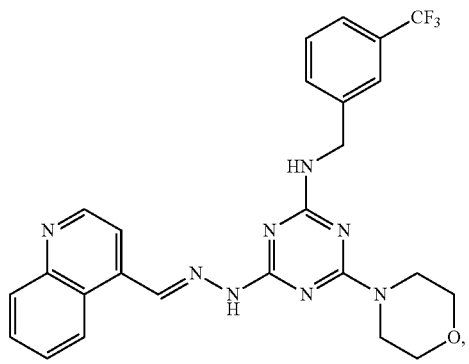

49
-continued
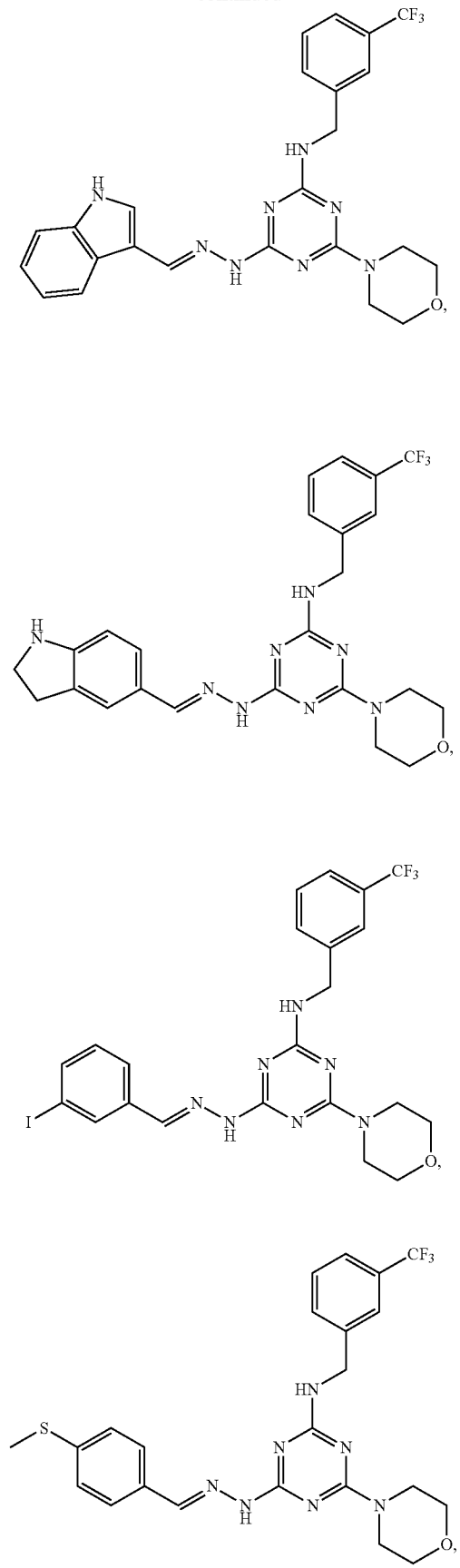
50
-continued
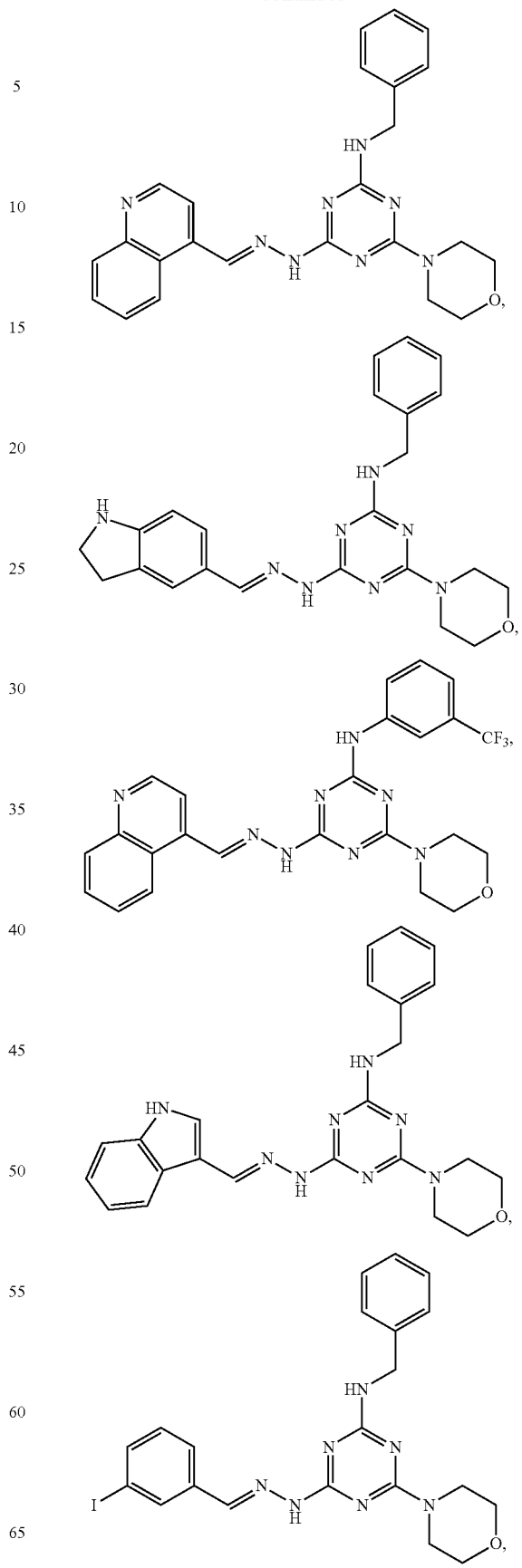

51
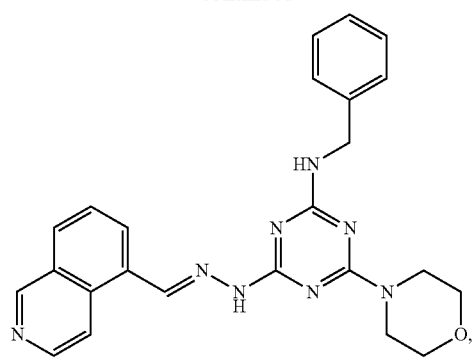
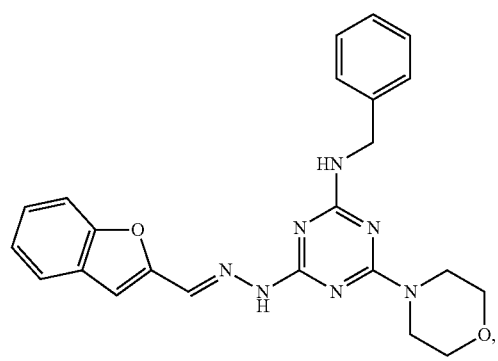
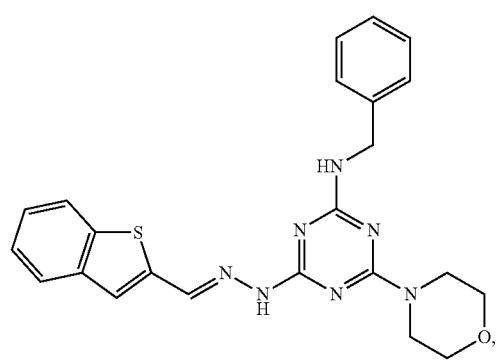
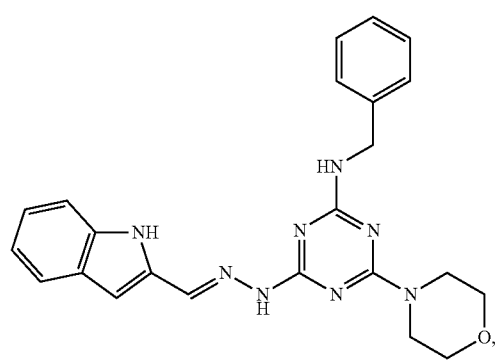
52
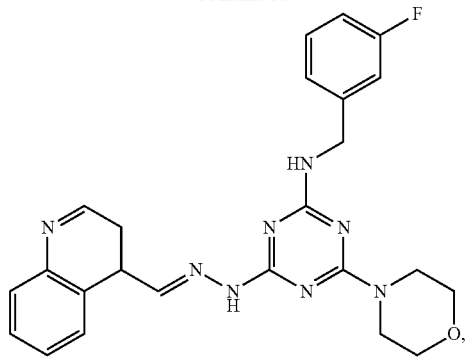
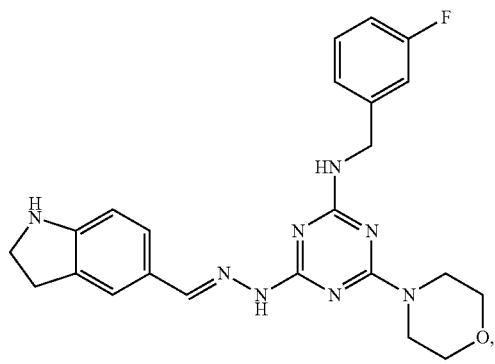
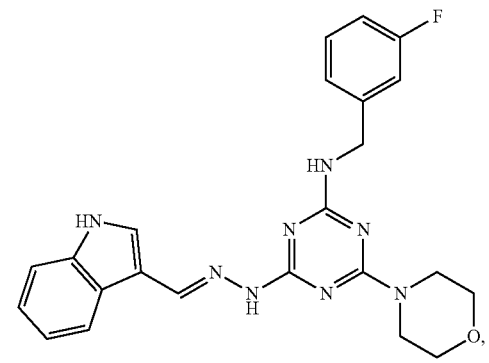
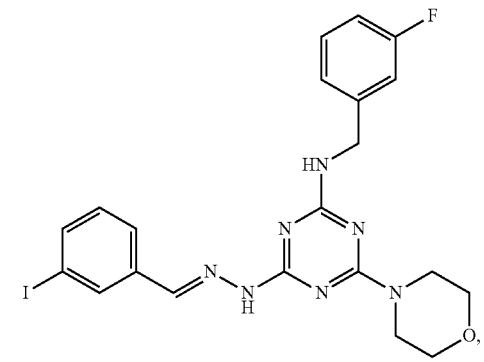

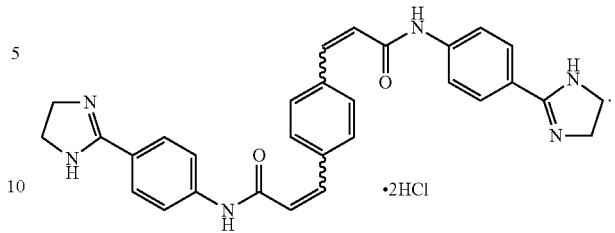

Formula III

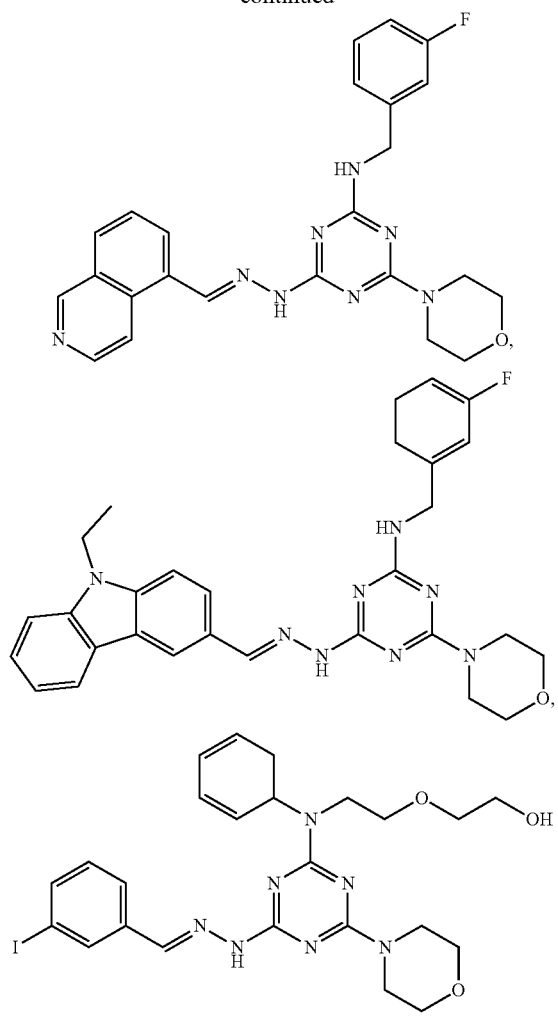

and a combination thereof.

11. The method according to claim 1, wherein the compound is the structure of Formula II

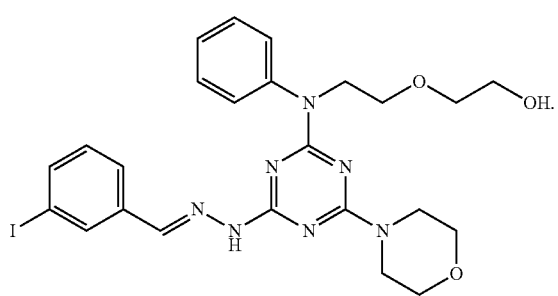

Formula II

12. The method according to claim 1, wherein the administering step further comprises an exosome secretion inhibitor administered in combination with the compound.

13. The method of claim 12, wherein the exosome secretion inhibitor comprises GW4869 having the structure of Formula III 14. The method according to claim 1, wherein the administering step further comprises an anti-PD-1 antibody administered in combination with the compound.

15. The method of claim 14, wherein the anti PD-1 antibody comprises the 29F.1A12 monoclonal antibody.

16. The method according to claim 1, wherein the cancer is selected from the group consisting of lung cancer, pancreatic cancer, breast cancer, colon cancer, colorectal cancer, melanoma, gastrointestinal cancer, gastric cancer, renal cancer, ovarian cancer, liver cancer, endometrial cancer, kidney cancer, prostate cancer, thyroid cancer, neuroblastoma, glioma, glioblastoma, cervical cancer, stomach cancer, bladder cancer, head and neck cancer, hepatoma and a combination thereof.

17. The method of claim 7, wherein the cancer is selected from the group consisting of cervical cancer, lung cancer, breast cancer, melanoma and a combination thereof.

18. A composition comprising a compound of Formula I and an anti-PD-1 antibody,

Formula I

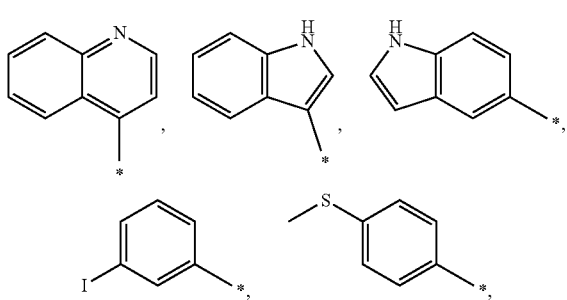

wherein R1 is selected from the group consisting of a hydrogen atom, a halogen atom and a halogenated group;

R2 is selected from the group consisting of

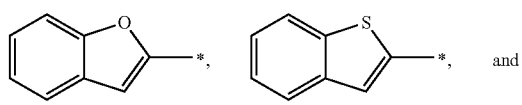
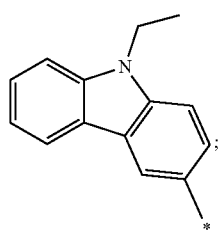
R3 is a hydrogen atom or
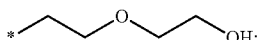
and
L is a linker group, —(CH$_2$)$_n$—, where n is an integer from 0-5;
wherein, when n=0, R1 is hydrogen, R2 is
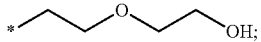
and R3 is
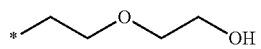 [SMILES: *CCOCCO]
19. The composition of claim 18, wherein the compound is selected the group consisting of
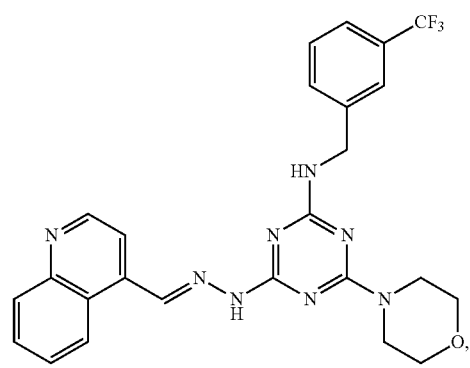
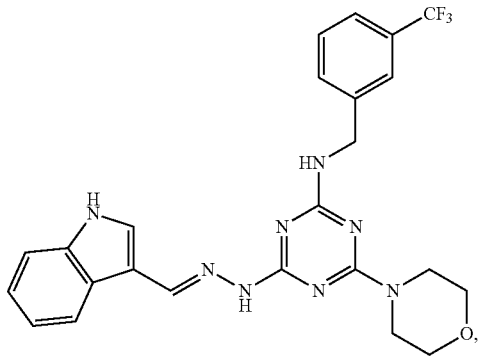
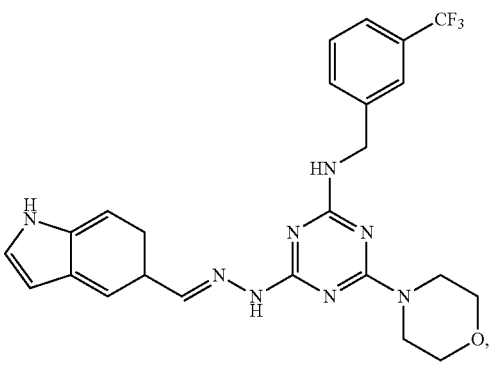
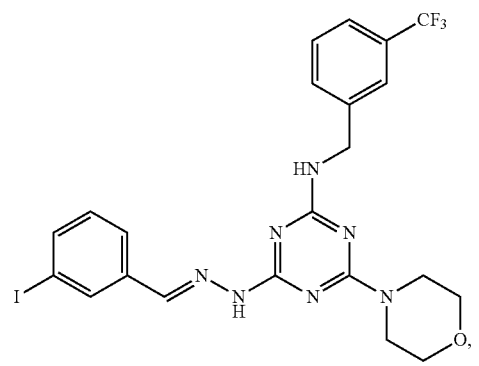
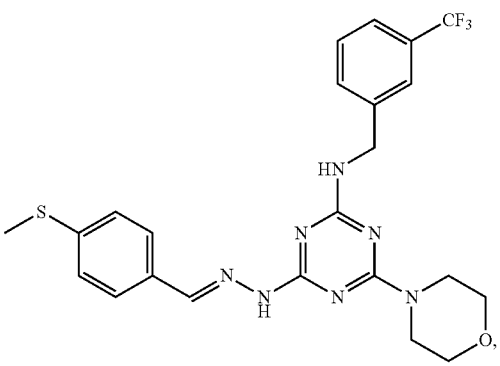

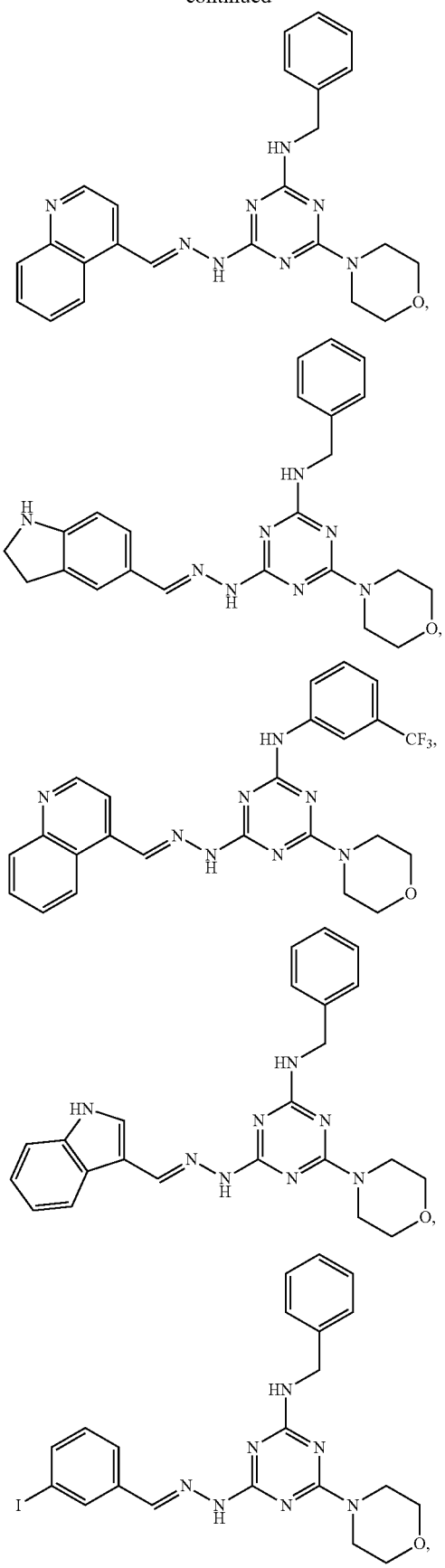
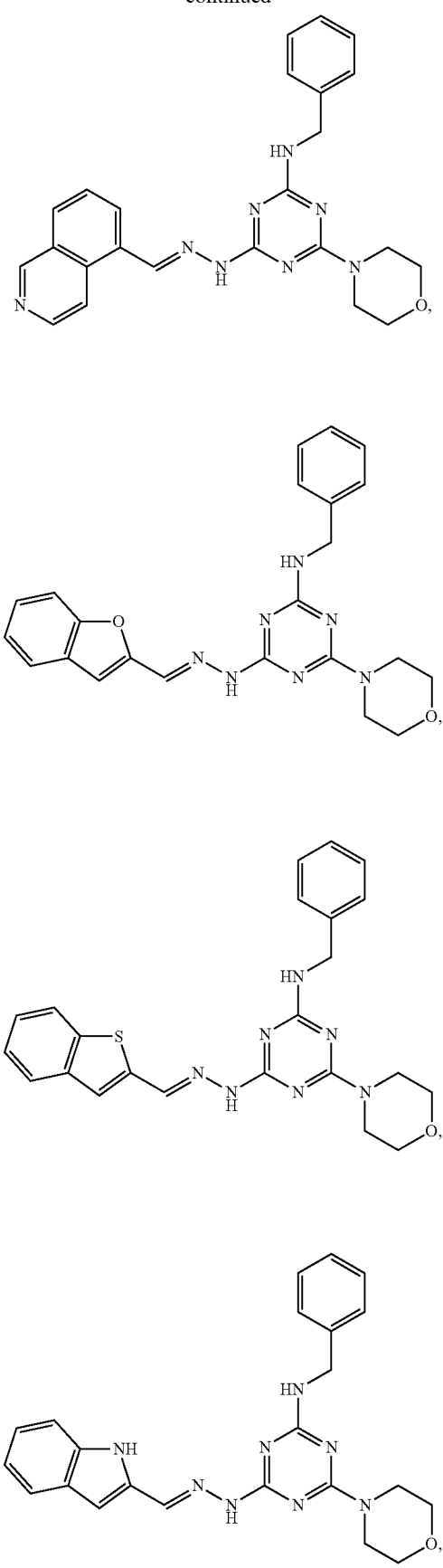

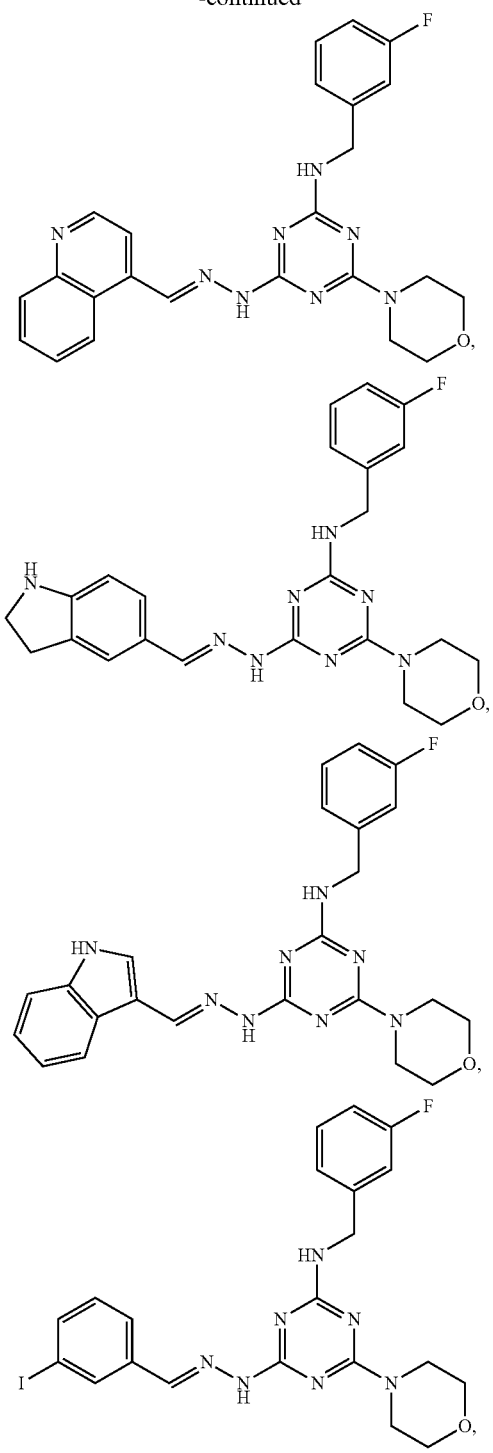

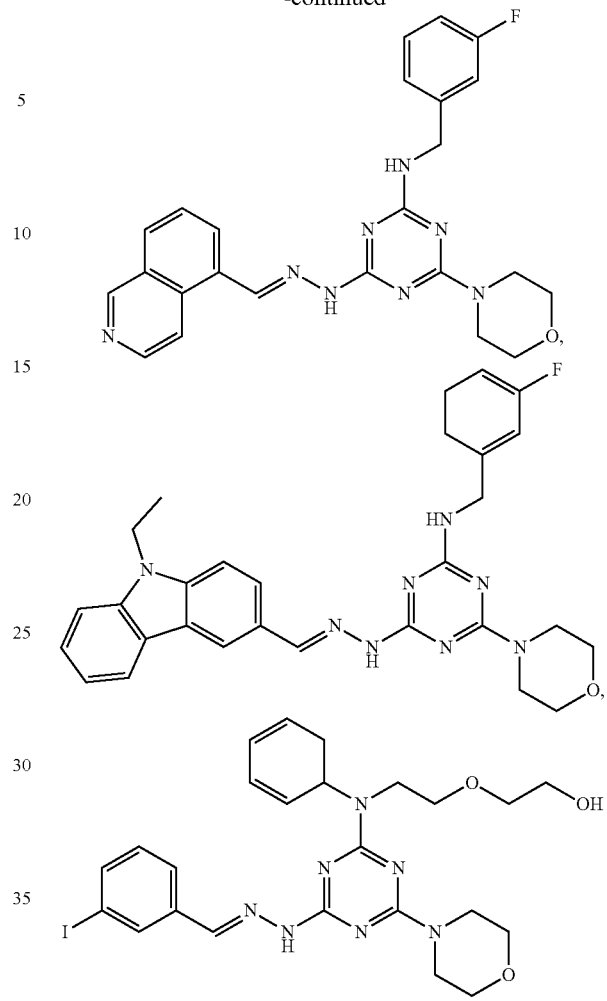

and a combination thereof.

20. The composition of claim 19, further comprises an exosome secretion inhibitor.

21. The composition according to claim 18, wherein anti PD-1 antibody comprises 29F.1A12 monoclonal antibody.

22. The composition according to claim 18, wherein the compound has an effective concentration of about 30 mg/kg.

23. The composition according to claim 18, wherein the anti-PD-1 antibody has an effective concentration of about 200 μg.

24. The composition according to claim 18, wherein the compound is administered in combination with the anti-PD-1 antibody.

25. The composition according to claim 24, wherein the compound is administered orally and the anti-PD-1 antibody is administered via intraperitoneal injection.

* * * * *